(12) United States Patent
Stürzebecher et al.

(10) Patent No.: US 9,090,658 B2
(45) Date of Patent: Jul. 28, 2015

(54) BASE-SUBSTITUTED BENZYLAMINE ANALOGS FOR USE AS COAGULATION FACTOR XA INHIBITORS, THE PRODUCTION AND USE THEREOF

(75) Inventors: Jörg Stürzebecher, Erfurt (DE); Torsten Steinmetzer, Jena (DE); Andrea Schweinitz, Jena (DE); Anne Stürzebecher, Weimar (DE); Daniel Dönnecke, Weimar (DE)

(73) Assignee: The Medicines Company (Leipzig) GmbH, Leipzig (DE)

( * ) Notice: Subject to any disclaimer, the term of this patent is extended or adjusted under 35 U.S.C. 154(b) by 387 days.

(21) Appl. No.: 10/571,026

(22) PCT Filed: Sep. 13, 2004

(86) PCT No.: PCT/EP2004/010225
§ 371 (c)(1),
(2), (4) Date: Sep. 28, 2006

(87) PCT Pub. No.: WO2005/026198
PCT Pub. Date: Mar. 24, 2005

(65) Prior Publication Data
US 2007/0066539 A1    Mar. 22, 2007

(30) Foreign Application Priority Data
Sep. 11, 2003 (DE) .................................. 103 42 108

(51) Int. Cl.
| | | |
|---|---|---|
| *A61K 38/05* | (2006.01) | |
| *C07K 5/04* | (2006.01) | |
| *C07K 5/078* | (2006.01) | |
| *C07K 5/065* | (2006.01) | |
| *C07K 5/087* | (2006.01) | |
| *C07K 5/097* | (2006.01) | |

(52) U.S. Cl.
CPC ......... *C07K 5/06139* (2013.01); *C07K 5/06078* (2013.01); *C07K 5/0812* (2013.01); *C07K 5/0821* (2013.01)

(58) Field of Classification Search
None
See application file for complete search history.

(56) References Cited

U.S. PATENT DOCUMENTS

| | | | |
|---|---|---|---|
| 5,518,735 A | 5/1996 | Stürzebecher et al. | |
| 5,602,253 A | 2/1997 | Antonsson et al. | |
| 5,705,487 A | 1/1998 | Schacht et al. | |
| 5,707,966 A | 1/1998 | Schacht et al. | |
| 5,710,130 A | 1/1998 | Schacht et al. | |
| 5,726,159 A | 3/1998 | Schacht et al. | |
| 5,863,929 A | 1/1999 | Klimkowski et al. | |
| 5,914,319 A | 6/1999 | Schacht et al. | |
| 6,030,972 A | 2/2000 | Böhm et al. | |
| 6,472,393 B1 | 10/2002 | Aliagas-Martin et al. | |
| 6,586,405 B2 | 7/2003 | Semple et al. | |
| 6,624,169 B1 | 9/2003 | Wilhelm et al. | |
| 6,680,320 B2 | 1/2004 | Wilhelm et al. | |
| 6,831,196 B2 | 12/2004 | Stürzebecher et al. | |
| 6,841,701 B2 * | 1/2005 | Sturzebecher et al. | ....... 564/157 |
| 6,841,702 B2 | 1/2005 | Magdolen et al. | |
| 7,038,074 B2 | 5/2006 | Moroder et al. | |
| 7,049,460 B1 | 5/2006 | Magdolen et al. | |
| 7,208,521 B2 | 4/2007 | Magdolen et al. | |
| 7,342,018 B2 | 3/2008 | Wilhelm et al. | |
| 7,407,982 B2 | 8/2008 | Steinmetzer et al. | |
| 7,538,216 B2 | 5/2009 | Sperl | |

(Continued)

FOREIGN PATENT DOCUMENTS

| | | |
|---|---|---|
| CH | 689 611 | 7/1999 |
| DE | 42 43 858 | 6/1994 |

(Continued)

OTHER PUBLICATIONS

Sturzebecher et al. WO 01/96366 A3, 1-12.*
Bauer, "Hilfsstoffe," in *Pharmazeutische Technologie*. Sucker et al. (eds.), Georg Thieme Verlag Stuttgart: New York, Chapter 5, pp. 174-216.
Choi-Sledeski et al., "Discovery of an Orally Efficacious Inhibitor of Coagulation Factor Xa Which Incorporates a Neutral $P_1$ Ligand," *J. Med. Chem.* 46:681-684 (2003).

(Continued)

*Primary Examiner* — Amber D Steele
*Assistant Examiner* — Schuyler Milton
(74) *Attorney, Agent, or Firm* — Clark & Elbing LLP

(57) ABSTRACT

The invention relates to the novel base-substituted benzylamine analogs of general formula (I), wherein A represents $P_2$-$P_1$ with $P_1$=(A) and $P_2$=(B), for use as coagulation factor Xa inhibitors. The invention also relates to the production and use of said analogs in the therapy and prophylaxis of cardiovascular diseases and thromboembolic events.

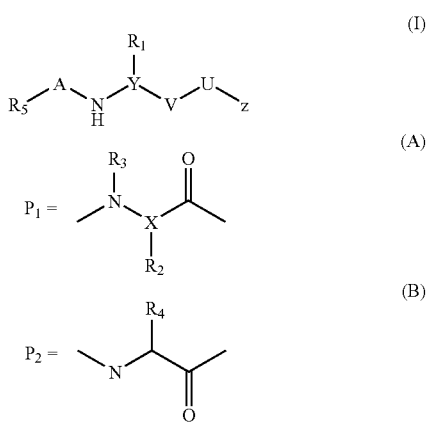

29 Claims, No Drawings

(56) References Cited

U.S. PATENT DOCUMENTS

| | | | |
|---|---|---|---|
| 7,608,623 | B2 | 10/2009 | Sperl et al. |
| 2004/0087511 | A1 | 5/2004 | Shiraishi et al. |
| 2004/0266766 | A1 | 12/2004 | Sperl |
| 2005/0119190 | A1 | 6/2005 | Stürzebecher et al. |
| 2005/0176993 | A1 | 8/2005 | Stürzebecher et al. |
| 2006/0068457 | A1 | 3/2006 | Ziegler et al. |
| 2006/0148901 | A1 | 7/2006 | Stürzebecher et al. |
| 2007/0055065 | A1 | 3/2007 | Stürzebecher et al. |
| 2008/0261998 | A1 | 10/2008 | Sperl et al. |
| 2009/0117185 | A1 | 5/2009 | Steinmetzer et al. |

FOREIGN PATENT DOCUMENTS

| | | | |
|---|---|---|---|
| DE | 100 29 014 | | 12/2001 |
| DE | 100 29 015 | A1 | 12/2001 |
| DE | 102 12 555 | | 9/2003 |
| DE | 10210590 | A1 | 10/2003 |
| DE | 103 01 300 | | 7/2004 |
| DE | 10301300 | A1 | 7/2004 |
| EP | 0 183 271 | | 6/1986 |
| EP | 0 669 317 | A1 | 8/1995 |
| EP | 0 672 658 | A1 | 9/1995 |
| EP | 1 364 960 | A1 | 11/2003 |
| WO | WO 92/08709 | | 5/1992 |
| WO | WO 94/18185 | | 8/1994 |
| WO | WO 94/29336 | | 12/1994 |
| WO | WO 95/17885 | | 7/1995 |
| WO | WO 95/29189 | | 11/1995 |
| WO | WO 96/25426 | | 8/1996 |
| WO | WO 97/23499 | | 7/1997 |
| WO | WO 99/05096 | | 2/1999 |
| WO | WO 00/04954 | | 2/2000 |
| WO | WO 00/05245 | | 2/2000 |
| WO | WO 00/14110 | | 3/2000 |
| WO | WO 00/17158 | | 3/2000 |
| WO | WO 00/58346 | | 10/2000 |
| WO | WO 00/58346 | A1 * | 10/2000 |
| WO | WO 00/64470 | | 11/2000 |
| WO | WO 01/81314 | | 11/2001 |
| WO | WO 01/96286 | A2 | 12/2001 |
| WO | WO 01/96366 | A2 | 12/2001 |
| WO | WO 01/96366 | A3 * | 12/2001 |
| WO | WO 01/97794 | | 12/2001 |
| WO | WO 02/06280 | | 1/2002 |
| WO | WO 02/14349 | | 2/2002 |
| WO | WO 02/20475 | | 3/2002 |
| WO | WO 02/50056 | | 6/2002 |
| WO | WO 03/070229 | | 8/2003 |
| WO | WO 2004/062657 | A1 | 7/2004 |

OTHER PUBLICATIONS

Gustafsson et al., "Effects of Melagatran, a New Low-Molecular-Weight Thrombin Inhibitor, on Thrombin and Fibrinolytic Enzymes," *Thromb. Haemost.* 79:110-118 (1998).

Gustafsson et al., "The Direct Thrombin Inhibitor Melagatran and Its Oral Prodrug H 376/95: Intestinal Absorption Properties, Biochemical and Pharmacodynamic Effects," *Thromb. Res.* 101:171-181 (2001).

Hera et al., "DX-9065a, a New Synthetic, Potent Anticoagulant and Selective Inhibitor for Factor Xa," *Thromb. Haemost.* 71:314-319(1994).

Herbert et al., "DX 9065A, a Novel, Synthetic, Selective and Orally Active Inhibitor of Factor Xa: In Vitro and In Vivo Studies," *J. Pharmacol. Exp. Ther.* 276:1030-1038 (1996).

Ho et al., "Exploratory Solid-Phase Synthesis of Factor Xa Inhibitors: Discovery and Application of $P_3$-Heterocyclic Amides as Novel Types of Non-Basic Arginine Surrogates," *Bioorg. Med. Chem. Lett.* 9:3459-3464 (1999).

Kettner and Shaw, "The Selective Affinity Labeling of Factor $X_a$ By Peptides of Arginine Chloromethyl Ketone," *Thromb. Res.* 22:645-652 (1981).

Künzel et al., "4-Amidinobenzylamine-Based Inhibitors of Urokinase," *Bioorg. Med. Chem. Lett.* 12:645-648 (2002).

Lee et al., "Noncovalent Tripeptidic Thrombin Inhibitors Incorporating Amidrazone, Amine and Amidine Functions at P1," *Bioorg. Med. Chem. Lett.* 12:1017-1022 (2002).

Maduskuie el al., "Rational Design and Synthesis of Novel, Potent Bis-Phenylamidine Carboxylate Factor Xa Inhibitors," *J. Med. Chem.* 41:53-62 (1998).

Mohan et al., "Solid-Phase Synthesis of N-Substituted Amidinophenoxy Pyridines as Factor Xa Inhibitors," *Bioorg. Med. Chem. Lett.* 8:1877-1882 (1998).

Ostrem et al., "Discovery of a Novel, Potent, and Specific Family of Factor Xa Inhibitors via Combinatorial Chemistry," *Biochemistry* 37:1053-1059 (1998).

Phillips et al., "Discovery of N-[2-[5-[Amino(imino)methyl]-2-hydroxyphenoxy]-3,5-difluoro-6-[3-(4,5-dihydro-1-methy1-1H-imidazol-2-yl)phenoxy]pyridin-4-yl]-N-methytglycine (ZK-807834): A Potent, Selective, and Orally Active Inhibitor of the Blood Coagulation Enzyme Factor Xa," *J. Med. Chem.* 41:3557-3562 (1998).

Quan et al., "Bisbenzamidine Isoxazoline Derivatives as Factor Xa Inhibitors," *Bioorg. Med. Chem. Lett.* 7:2813-2818 (1997).

Sato et al., "YM-60828, a Novel Factor Xa Inhibitor: Separation of Its Antithrombotic Effects from Its Prolongation of Bleeding Time," *Eur. J. Pharmacol.* 339:141-146 (1997).

Sato et al., "Antithrombotic Effects of YM-60828, a Newly Synthesized Factor Xa Inhibitor, in Rat Thrombosis Models and Its Effects on Bleeding Time," *Br. J. Pharmacol.* 123:92-96 (1998).

Schechter and Berger, "On the Size of the Active Site in Proteases. I. Papain," *Biochem. Biophys. Res. Commun.* 27:157-162 (1967).

Sperl et al., "Urethanyl-3-Amidinophenylalanine Derivatives as Inhibitors of Factor Xa. X-Ray Crystal Structure of a Trypsin/Inhibitor Complex and Modeling Studies," *Biol. Chem.* 381:321-329 (2000).

Stürzebecher et al., "Synthetic Inhibitors of Bovine Factor Xa and Thrombin Comparison of Their Anticoagulant Efficiency," *Thromb. Res.* 54:245-252 (1989).

Wikström and Owens, "Development and Validation of a Chiral Capillary Electrophoresis Method for Melagatran and Ximelagatran Drug Substances," *J. Sep. Sci.* 25:1167-1174 (2002).

Zhu and Scarborough, "Recent Advances in Inhibitors of Factor Xa in the Prothrombinase Complex," *Curr. Opin. Cardiovasc. Pulmon. Renal Invest. Drugs* 1:63-88 (1999).

U.S. Appl. No. 12/429,766, filed Apr. 24,2009, Steinmetzer et al.

Akers, "Excipient-Drug Interactions in Parenteral Formulations." *Journal of Pharmaceutical Sciences*, 91(11):2283-2300 (2002).

Asghar et al., "Human Plasma Kallikreins and their Inhibition by Amidino Compounds," *Biochim. Biophys. Acta* 438:250-264 (1976).

Baker et al., "Inhibition of Cancer Cell Urokinase Plasminogen Activator by its Specific Inhibitor PAI-2 and Subsequent Effects on Extracellular matrix Degradation," *Cancer Research* 50: 4676-4684 (1990).

Bookser et al., "Syntheses of Quadruply Two- and Three-Atom, Aza-Bridged, Cofacial Bis (5,10,15,20- Tetraphenylporphyrins)," *J. Am. Chem. Soc.* 113:4208-4218 (1991).

Cajot et al., "Plasminogen-Activator Inhibitor Type 1 is a Potent Natural Inhibitor of Extracellular Matrix Degradation by Fibrosarcoma and Colon Carcinoma Cells," *Proc. Natl. Acad. Sci. USA* 87:6939-6943 (1990).

Collen et al., "In Vivo Studies of a Synthetic Inhibitor of Thrombin," *J. Lab. Clin. Med.* 99:76-83 (1982).

Coussens et al., "Matrix Metalloproteinase Inhibitors and Cancer: Trials and Tribulations," *Science* 295:2387-2392 (2002).

Dexter et al., "N,N-Dimethylformamide-induced Alteration of Cell Culture Characteristics and Loss of Tumorigenicity in Cultured Human Colon Carcinoma Cells," *Cancer Res.* 39:1020-1025 (1979).

Dixon, "The Determination of Enzyme Inhibitor Constants," *Biochem. J.* 55:170-171 (1953).

Duggan et al., "Urokinase Plasminogen Activator and Urokinase Plasminogen Activator Receptor in Breast Cancer," *Int. J. Cancer* 61:597-600 (1995).

Enyedy et al., "Structure-Based Approach for the Discovery of Bis-benzamidines as Novel Inhibitors of Matriptase," *J. Med. Chem.* 44:1349-1355 (2001).

(56) References Cited

OTHER PUBLICATIONS

Frérot et al., "PyBOP® and PyBroP: Two reagents for the difficult coupling of the α,α-dialkyl amino acid, Aib," *Tetrahedron*, 47(2):259-270 (1991).
Friedrich et al., "Catalytic Domain Structures of MT-SP1/Matriptase, a Matrix-degrading Transmembrane Serine Proteinase," *J. Biol. Chem.* 277:2160-2168 (2002).
Fareed et al., "Inhibition of Serine Proteases by Low Molecular Weight Peptides and Their Derivatives," *Ann. N. York Acad. Sci.* 370, 765-784 (1981).
Garrett et al., "Peptide Aldehyde Inhibitors of the Kallikreins: An Investigation of Subsite Interactions with Tripeptides Containing Structural Variations at the Amino Terminus," *J. Pept. Res.* 52:60-71 (1998).
Garrett et al., "Synthesis of Potent and Selective Inhibitors of Human Plasma Kallikrein," *Bioorg. Med. Chem. Lett.* 9:301-306 (1999).
Gustafsson et al., "Effects of Inogatran, A New Low-Molecular-Weight Thrombin Inhibitor, in Rat Models of Venous and Arterial Thrombosis, Thrombolysis and Bleeding Time," Blood Coagulation and Fibrinolysis 7:69-79 (1996).
Hooper et al., "Type II Transmembrane Serine Proteases," *J. Biol. Chem.* 276:857-860 (2001).
Ihara et al., "Prometastatic Effect of $N$-Acetylglucosaminyltransferase V Is Due to Modification and Stabilization of Active Matriptase by Adding β1-6 GlcNAc Branching," *J. Biol. Chem.* 277:16960-16967 (2002).
Isobe, "Inhibitory Effect of Gabexate (FOY) on Contact System," *Blood & Vessel* 12:135-138 (1981).
Judkins et al., "A Versatile Synthesis of Amidines from Nitriles Via Amidoximes," *Synthetic Communications* 26: 4351-4367 (1996).
Kang et al., "Tissue Microarray Analysis of Hepatocyte Growth Factor/Met Pathway Components Reveals a Role for Met, Matriptase, and Hepatocyte Growth Factor Activator Inhibitor 1 in the Progression of Node-negative Breast Cancer," *Cancer Res.* 63:1101-1105 (2003).
Kettner et al., "Inactivation of Trypsin-Like Enzymes with Peptides of Arginine Chloromethyl Ketone," *Methods in Enzymology* 80:826-843 (1981).
Kettner et al., "The Selective Inhibition of Thrombin by Peptides of Boroarginine," *J. Biol. Chem.* 265, 18289-18297 (1990).
Kettner et al., "The Selective Affinity Labeling of Factor $X_a$ by Peptides of Arginine Chloromethyl Ketone," *Thromb. Res.* 22:645-652 (1981).
Kim et al., "Preparation of Argatroban Analog Thrombin Inhibitors with Reduced Basic Guanidine Moiety, and Studies of Their Cell Permeability and Antithrombotic Activities," *Med. Chem. Res.* 377-383 (1996).
Kirk, "4-Lithio-1-Tritylimidazole as a Synthetic Intermediate, Synthesis of Imidazole-4-Carboxaldehyde," *J. Heterocyclic Chem.* 22:57-59 (1985).
Kruger et al., "Host TIMP-1 Overexpression Confers Resistance to Experimental Brain Metastasis of a Fibrosarcoma Cell Line," *Oncogene* 16:2419-2423 (1998).
Kruger et al., "The Bacterial *LacZ* Gene: An Important Tool for Metastasis Research and Evaluation of New Cancer Therapies," *Cancer and Metastasis Reviews* 17:285-294 (1999).
Lawson et al., "Studies on the Inhibition of Human Thrombin: Effects of Plasma and Plasma Constituents Folia Haematol," *Leipzig* 109, 52-60 (1982).
Leadley, "Coagulation Factor Xa Inhibition: Biological Background and Rationale," *Curr. Topics in Med. Chem.*, 1:151-159 (2001).
Lee et al., "Noncovalent Thrombin Inhibitors Incorporating an Imidazolylethynyl P1," *Bioorganic & Medicinal Chemistry Letters*, 10:2775-2778 (2000).
Lee et al., "Activation of Hepatocyte Growth Factor and Urokinase/Plasminogen Activator by Matriptase, an Epithelial Membrane Serine Protease," *J. Biol. Chem.* 275:36720-36725 (2000).
Lin et al., "Characterization of a Novel, Membrane-bound, 80-kDa Matrix-degrading Protease from Human Breast Cancer Cells," *J. Biol. Chem.* 272:9147-9152 (1997).

Lin et al., "Molecular Cloning of cDNA for Matriptase, a Matrix-degrading Serine Protease with Trypsin-like Activity," *J. Biol. Chem.* 274:18231-18236 (1999).
Lin et al., "Purification and Characterization of a Complex Containing Matriptase and a Kunitz-type Serine Protease Inhibitor from Human Milk," *J. Biol. Chem.* 274:18237-18242 (1999).
Long et al., "Synthesis and Evaluation of the Sunflower Derived Trypsin Inhibitor as a Potent Inhibitor of the Type II Transmembrane Serine Protease, Matriptase," *Bioorg. Med. Chem. Lett.* 11:2515-2519 (2001).
Maignan et al., "The Use of 3D Structural Data in the Design of Specific Factor Xa Inhibitors," *Curr. Topics in Med. Chem.* 1:161-174 (2001).
Mignatti et al., "Biology and Biochemistry of Proteinases in Tumor Invasion," *Physiological Reviews* 73:161-195 (1993).
Morrissette et al., "Low Molecular Weight Thrombin Inhibitors With Excellent Potency, Metabolic Stability, and Oral Bioavailability," *Bioorganic & Med. Chem. Letters*, 14:4161-4164 (2004).
Muramatu and Fuji, "Inhibitory Effects of ω-Amino Acid Esters on Trypsin, Plasmin, Plasma Kallikrein and Thrombin," *Biochim. Biophys. Acta* 242:203-208 (1971).
Muramatu and Fuji, "Inhibitory Effects of ω-Guanidino Acid Esters on Trypsin, Plasmin, Plasma Kallikrein and Thrombin," *Biochim. Biophys. Acta* 268:221-224 (1972).
Muramatu et al., "Inhibitory Effects of Aryl trans-4 (Aminomethyl) Cyclohexanecarboxylate on Serine Proteases, and their Antiallergic Effects," *Hoppe-Seyler's Z. Physiol. Chem.* 363:203-211 (1982).
Nar et al., "Structural Basis for Inhibition Promiscuity of Dual Specific Thrombin and Factor Xa Blood Coagulation Inhibitors," *Structure*, 9:29-37 (2001).
Nelson et al., "Stereoselective Synthesis of a Potent Thrombin Inhibitor by a Novel P2-P3 Lactone Ring Opening," *J. Org. Chem.* 69:3620-3627 (2004).
Oberst et al., "Expression of the Serine Protease Matriptase and Its Inhibitor HAI-1 in Epithelial Ovarian Cancer: Correlation with Clinical Outcome and Tumor Clinicopathological Parameters," *Clin. Cancer Res.* 8:1101-1107 (2002).
Ohno et al., "FOY: [Ethyl-(6-Guanidinohexanoyloxy) Benzoate] Methanesulfonate as a Serine Proteinase Inhibitor. I. Inhibition of Thrombin and Factor Xa in Vitro," *Thromb. Res.* 19:579-588 (1980).
Okada et al., "Development of Plasmin and Plasma Kallikrein Selective Inhibitors and their Effect on M1 (Melanoma) and ht29 Cell Lines," *Bioorg. Med. Chem. Lett.* 10:2217-2221 (2000).
Okada et al., "Development of Plasma Kallikrein Selective Inhibitors," *Biopolymers* 51:41-50 (1999).
Okamoto et al., "Recent Studies of the Synthetic Selective Inhibitors; With Special Reference to Non-Plasmin Fibrinolytic Enzyme, Plasmin and Plasma-Kallikrein Thromb," *Res., Suppl. I*, 131-141 (1988).
Ossowski et al., "Antibodies to Plasminogen Activator Inhibit Human Tumor Metastasis," *Cell* 35:611-619 (1983).
Patani et al., "Bioisosterism: A Rational Approach in Drug Design." *Chem. Rev.* 96:3147-3176 (1996), pp. 3147-3148 and 3170.
Pauls et al., "The Design of Competitive, Small-Molecule Inhibitors of Coagulation Factor Xa," *Frontiers in Med. Chem.*, 1:129-152 (2004).
Pedersen et al., "Prognostic Impact of Urokinase, Urokinase Receptor, and Type 1 Plasminogen Activator Inhibitor in Squamous and Large Cell Lung Cancer Tissue" *Cancer Research* 54:4671-4675 (1994).
Perzborn et al., "In Vitro and In Vivo Studies of the Novel Antithrombotic Agent BAY 59-7939—an Oral, direct Factor Xa Inhibitor," *J. Thromb. & Haemost.* 3:514-521 (2005).
Quan et al., "Discovery of 1-(3'-Aminobenzisoxazol-5'-yl)-3-trifluormethyl-$N$-[2-fluoro-4-[(2'-dimethylaminomethyl)imidazol-1-yl]phenyl]-1$H$-pyrazole-5-carboxyamide Hydrochloride (Razaxaban), a Highly Potent, Selective, and Orally Bioavailable Factor Xa Inhibitor," *J. Med. Chem.* 48:1729-1744 (2005).
Quan et al., "The Race to Orally Active Factor Xa Inhibitor: Recent Advances," *Curr. Opin. In Drug Discovery & Development*, 7:460-469 (2004).

(56) References Cited

OTHER PUBLICATIONS

Ratnoff, "Studies on the Inhibition of Ellagic Acid-Activated Hageman factor (factor XII) and Hageman factor fragments," *Blood* 57:55-58 (1981).
Renatus et al., "Structural and Functional Analyses of Benzamidine-based Inhibitors in Complex with Trypsin: Implications for the Inhibition of Factor Xa, tPA, and Urokinase." *J. Med. Chem.* 41:5445-5456 (1998).
Reuning et al., "Multifunctional Potential of the Plasminogen Activation System in Tumor Invasion and Metastasis (Review)," *International Journal of Oncology* 13:893-906 (1998).
Rittle et al., "Unexpected Enhancement of Thrombin Inhibitor Potency with o-Aminoalkylbenzylamides in the P1 Position," *Bioorg. Med. Chem. Lett.* 13:3477-3482 (2003).
Rubini et al., "Synthesis of Isosteric Methylene-oxy Pseudopeptide Analogues as Novel Amide Bond Surrogate Units." *Tetrahedron* 43(21):6039-6045 (1986).
Satoh et al., "Medicinal Chemical Studies on Synthetic Protease Inhibitors, trans-4-Guanidinomethylcyclohexanecarboxylic Acid Aryl Esters," *Chem. Pharm. Bull.* 33:647-654 (1985).
Schmitt et al., "Clinical Impact of the Plasminogen Activation System in Tumor Invasion and Metastasis: Prognostic Relevance and Target for Therapy," *Thrombosis and Haemostasis* 78:285-296 (1997).
Shi et al., "Identification and Characterization of a Novel Matrix-degrading Protease from Hormone-dependent Human Breast Cancer Cells," *Cancer Res.* 53:1409-1415 (1993).
Silverberg et al., "Enzymatic activities of activated and zymogen forms of human Hageman factor (factor XII)," *Blood* 60:64-70 (1982).
Soll et al., "Amidinohydrazones as Guanidine Bioisosteres: Application to a New Class of Potent, Selective and Orally Bioavailable, Non-Amide-Based Small Molecule Thrombin Inhibitors," *Bioorganic & Medicinal Chemistry Letters* 10:1-4 (2000).
Sperl et al., "(4-Aminomethyl) Phenylguanidine Derivates as Nonpeptidic Highly Selective Inhibitors of Human Urokinase," *Proc. Natl. Acad. Sci. USA* 97:5113-5118 (2000).
Stauffer et al., "9-Hydroxyazafluorenes and their Use in Thrombin Inhibitors," *J. Med. Chem.*, 48: 2282-2293 (2005).
Stephens et al., "The Urokinase Plasminogen Activator System as a Target for Prognostic Studies in Breast Cancer," *Breast Cancer Research and Treatment*, 52:99-111 (1998).
Stürzebecher et al., "Novel Plasma Kallikrein Inhibitors of the Benzamidine Type," *Brazilian Journal Med. Biol. Res.* 27:1929-1934 (1994).
Stürzebecher et al., "3-Amidinophenylalanine-Based Inhibitors of Urokinase," *Bioorganic & Medicinal Chemistry Letters* 9:3147-3152 (1999).
Stürzebecher et al., "Synthesis and Structure—Activity Relationships of Potent Thrombin Inhibitors: Piperazides of 3-Amidinophenylalanine," *J. Med. Chem.* 40:3091-3099 (1997).
Takeuchi et al., "Reverse Biochemistry: Use of Macromolecular Protease Inhibitors to Dissect Complex Biological Processes and Identify a Membrane-type Serine Protease in Epithelial Cancer and Normal Tissue," *Proc. Natl. Acad. Sci. USA* 96:11054-11061 (1999).
Takeuchi et al., "Cellular Localization of Membrane-type Serine Protease 1 and Identification of Protease-activated Receptor-2 and Single-chain Urokinase-type Plasminogen Activator as Substrates," *J. Biol. Chem.* 275:26333-26342 (2000).
Tamura et al., "Synthesis and Biological Activity of Peptidyl Aldehyde Urokinase Inhibitors." *Bioorganic & Medicinal Chemistry Letters*, 10:983-987 (2000).
Teno et al., "Development of Selective Inhibitors against Plasma," Kallikrein *Chem. Pharm. Bull.* 39:2930-2936 (1991).
Towle et al., "Inhibition of Urokinase by 4-Substituted Benzo[b]thiophene-2-Carboxamidines: An Important New Class of Selective Synthetic Urokinase Inhibitor," *Cancer Research* 53:2553-2559 (1993).
Tucker et al., "Potent Noncovalent Thrombin Inhibitors That Utilize the Unique Amino Acid d-Dicyclohexylalanine in the P3 Position. Implications on Oral Bioavailability and Antithrombotic Efficacy," *J. Med. Chem.* 40:1565-1569 (1997).
Tucker et al., "Synthesis of a Series of Potent and Orally Bioavailable Thrombin Inhibitors That Utilize 3,3-Disubstituted Propionic Acid Derivatives in the P3 Position," *J. Med. Chem.* 40:3687-3693 (1997).
Tsuda et al., Structure-Inhibitory Activity Relationship of Plasmin and Plasma Kallikrein Inhibitors, *Chem. Pharm. Bull.* 49:1457-1463 (2001).
Vassalli et al., "Amiloride Selectively Inhibits the Urokinase-Type Plasminogen Activator," *FEB* 214:187-191 (1987).
von der Saal et al, "Derivatives of 4-Amino-Pyridine as Selective Thrombin Inhibitors," *Bioorganic & Medicinal Chemistry Letters* 7:1283-1288 (1997).
Zeslawska et al., "Crystals of the Urokinase Type Plasminogen Activator Variant βc-uPA in Complex with Small Molecule Inhibitors Open the Way towards Structure-based Drug Design," *J. Mol. Biol.* 301:465-475 (2000).
Zeslawska et al., "Crystals of Urokinase Type Plasminogen Activator Complexes Reveal the Binding Mode of Peptidomimetic Inhibitors," *J. Mol.Biol.* 328:109-118 (2003).
Zhang et al., "Assignment of Human Putative Tumor Suppressor Genes ST13 (alias SNC6) and ST14 (alias SNC19) to Human Chromosome Bands 22q13 and 11q24→q25 by in Situ Hybridization," *Cytogenet, Cell Genet.* 83:56-57 (1998).
Office Action pertaining to U.S. Appl. No. 10/297,557 mailed Nov. 4, 2003.
Office Action pertaining to U.S. Appl. No. 10/311,364 mailed Nov. 19, 2003.
Office Action pertaining to U.S. Appl. No. 10/311,364 mailed Apr. 1, 2004.
Office Action pertaining to U.S. Appl. No. 10/506,579 mailed Jan. 30, 2009.
Office Action pertaining to U.S. Appl. No. 10/506,579 mailed Jul. 17, 2008.
Office Action pertaining to U.S. Appl. No. 10/540,958, mailed Nov. 17, 2008.
Office Action pertaining to U.S. Appl. No. 10/540,958, mailed Jun. 11, 2009.
Office Action pertaining to U.S. Appl. No. 10/555,821, mailed Jan. 21, 2009.
Eriksson et al., "The Direct Thrombin Inhibitor Melagatran Followed by Oral Ximelagatran Compared with Enoxaparin for the Prevention of Venous Thromboembolism After Total Hip or Knee Replacement: The Express study," *Journal of Thrombosis and Haemostasis*, 1:2490-2496 (2003).
Fareed et al., "Inhibition of Serine Proteases by Low Molecular Weight Peptides and Their Derivatives", *Ann. N. Y. Acad. Sci.* 370:765-784 (1981).
Francis et al., "Comparison of Ximelagatran with Warfarin for the Prevention of Venous Thromboembolism After Total Knee Replacement," *N. Engl. J. Med.* 349:1703-1712 (2003).
Griffin, "Role of Surface in Surface-Dependent Activation of Hageman Factor (Blood Coagulation Factor XII)", *Proc. Natl. Acad. Sci. USA* 75:1998-2002 (1978).
Gustafsson et al., "A New Oral Anticoagulant: The 50-Year Challenge," *Nature Reviews Drug Discovery* 3:649-659 (2004).
Kaplan, "Initiation of the Intrinsic Coagulation and Fibrinolytic Pathways of Man: The Role of Surfaces, Hageman Factor, Prekallikrein, High Molecular Weight Kininogen, and Factor XI," *Prog. Hemostasis Thromb.* 4:127-175 (1978).
Robinson et al., "Chapter 9. Anticoagulants: Inhibitors of the Factor VIIa/Tissue Factor Pathway,"*Ann. Rep. Med. Chem.* 37:85-94 (2002).
Tada et al., "Isolation of Plasma Kallikrein by High Efficiency Affinity Chromatography and Its Characterization," *Biol. Pharm. Bull.* 24:520-524 (2001).
Weitz, "New Anticoagulants for Treatment of Venous Thromboembolism," *Circulation*, 110:I-19-I-26 (2004).
Office Action pertaining to U.S. Appl. No. 10/506,579 mailed Dec. 16, 2009.

* cited by examiner

BASE-SUBSTITUTED BENZYLAMINE ANALOGS FOR USE AS COAGULATION FACTOR XA INHIBITORS, THE PRODUCTION AND USE THEREOF

CROSS REFERENCE TO RELATED APPLICATIONS

This application is the U.S. National Stage of International Application No. PCT/EP2004/010255, filed Sep. 13, 2004, which claims benefit of German patent application no. 10342108.4, filed Sep. 11, 2003, hereby incorporated by reference.

The invention relates to novel base-substituted benzylamine analogs as coagulation factor Xa inhibitors, their preparation and use for the therapy and prophylaxis of cardiovascular disorders and thromboembolic events.

The heparin-type anticoagulants currently employed clinically, and the vitamin K antagonist do not comply with all the requirements for an "ideal" antithrombotic agent. For this reason, alternatives are sought with small-molecule inhibitors of coagulation enzymes, specifically of thrombin and factor Xa (F Xa). A particular advantage of F Xa inhibitors compared with thrombin inhibitors might be the smaller tendency to bleeding which has been found in various animal experiments. Thus, antithrombotically effective doses had only a minimal influence on the bleeding time (J. M. Herbert et al., J. Pharmacol. Exp. Ther. 276, 1030-1038, 1996; K. Sato et al., Br. J. Pharmacol. 123, 92-96, 1998).

The first non-peptide compounds having high affinity for F Xa were symmetrical bis-benzamidines ($K_i$=13 nM for the most effective compound BABCH) (J. Stürzebecher et al., Thromb. Res. 54, 245-252, 1998). The naphthamidine derivative DX-9065a also has two basic groups and is a selective F Xa inhibitor with $K_i$=24 nM (T. Hara et al., Thromb. Haemost. 71, 314-319, 1994). The inhibitor YM-60828 which is structurally related to DX-9065a (K. Sato et al. Eur. J. Pharmacol. 339, 141-146, 1997) is even more effective ($K_i$=1.3 nM). In the interim, a whole series of further bisbasic compounds has been described, in which, for example, two benzamidine residues are linked via an oxazoline ring ($K_i$=18 nM) (M. L. Quan et al., Bioorg. Med. Chem. Lett. 7, 2813-2818, 1997) or a carboxymethylalkyl chain ($K_i$=34 nM) (T. P. Maduskuie et al., J. Med. Chem. 41, 53-62, 1998). The particular disadvantage of the bisbasic compounds is the low bioavailability after oral administration.

F Xa inhibitors comprising only one basic group have also been described. N-Substituted amidinophenoxypyridines ($K_i$=0.11 nM for BX-807834) have been developed on the basis of BABCH (R. Mohan et al., Bioorg. Med. Chem. Lett. 8, 1877-1882, 1998; G. B. Phillips et al. J. Med. Chem. 41, 3557-3562, 1998). Amides of Nα-adamantyloxycarbonyl-3-amidinophenylalanine ($K_i$=74 nM for the most effective compound) are selective F Xa inhibitors (S. Sperl et al., Biol. Chem. 381, 321-329, 2000), whereas Nα-arylsulfonyl-aminoacylated esters of 3-amidinophenylalanine have a small inhibitory effect ($K_i$=840 nM for TAPAM) (J. Stürzebecher et al., Thromb. Res. 54, 245-252, 1998). WO 96/10022 discloses inhibitors which no longer have a strong charge ($K_i$=3.0 nM for the most effective compound). A further series of effective factor Xa inhibitors without basic substituents was recently described by Choi-Sledeski et al. (J. Med. Chem. 46, 681-684, 2003).

To date, only a few peptides derived from the substrate sequence Ile-Glu-Gly-Arg (SEQ ID NO: 1) have been described as F Xa inhibitors. The chloromethyl ketones described by Kettner and Shaw (Thromb. Res. 22, 645-652, 1981) are irreversible F Xa inhibitors and are unsuitable for in vivo applications. By contrast, the peptides SEL 2489 ($K_i$=25 nM) and SEL 2711 ($K_i$=3 nM) are extremely effective (J. A. Ostrem et al., Biochemistry 37, 1053-1059, 1998). There have also been descriptions of some peptidyl-arginine aldehydes and peptidyl-arginyl ketones which, besides argininal or an arginyl ketone derivative such as, for example, arginyl-ketothiazole in position P3, have a D-arginine or an unnatural basic amino acid such as, for example, 4-amidinophenylalanine, 3- or 4-amidinopiperidinylalanine and 4-guanidinophenylalanine in P3 (Z. H. Jonathan, Bioorg. Med. Lett. 9, 3459-3464, 1999 and review article: Zhu and Scarborough Current Opinion in Cardiovascular, Pulmonary & Renal Investigational Drugs 1999, 1, 63-88).) The application WO 01/96366 discloses inhibitors which are derived from acylated amidinobenzylamine and, besides a natural amino acid in P2, comprise a D-Ser ether or a comparable derivative of an unnatural amino acid. Compounds of this type inhibit both F Xa ($K_i$=30 nM for the most effective compound) and the coagulation of human blood plasma very effectively. However, compounds of this type have only inadequate pharmacokinetic properties for application in vivo; they are scarcely absorbed after oral administration and are very rapidly eliminated from the circulation after i.v. administration in experimental animals.

U.S. Pat. No. 5,914,319 describes thrombin inhibitors which have a d-homophenylalanine or d-homocyclohexylalanine in position P3 and also show a weak factor Xa inhibition with inhibitory constants in the micromolar range (for factor Xa: $K_{ass}$<5.5×10$^6$ l/mol, equivalent to about $K_i$>0.18 μM). However, these inhibitors have an obligatory imino acid in position P2, i.e. analogs of proline or N(alkyl)glycine derivatives. The thrombin affinity is also distinctly increased, and the selectivity ratio ($K_i$ for thrombin/$K_i$ for F Xa) is <0.08 for the indicated compounds.

The invention is therefore based on the object of indicating an active ingredient which is suitable for therapeutic applications and which inhibits coagulation factor Xa with high activity and specificity and which preferably circulates for as long as possible in the body after i.v., s.c. or oral administration.

It has surprisingly been found that acylated amidinobenzylamine of the general formula I indicated in claim 1

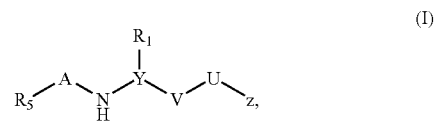

where
A is $P_2$-$P_1$ with

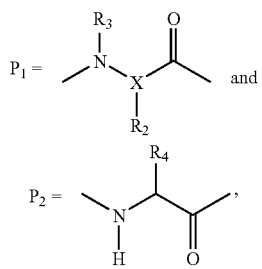

in particular compounds of 4-amidinobenzylamine both very effectively inactivate factor Xa and are also slowly eliminated from the circulation if, besides the amidino function, further charged or polar groups are introduced, it having emerged in particular that D-homophenylalanine, D-homotyrosine or D-homo-4-pyridylalanine and its derivatives at position $P_2$ of the general formula I are particularly effective. It was also possible through the use of selected α-amino acids in position P2 to decisively increase the selectivity as factor Xa inhibitors, which was particularly surprising.

For clarification, it is pointed out that the naming of the radicals $P_2$ and $P_1$ in the structural segment A of the general formula I does not refer to the otherwise normally used nomenclature of the amino acid residues in peptide substrates of serine proteases and inhibitors derived therefrom, as introduced by Schechter and Berger (Schechter and Berger, Biochem. Biophys. Res. Comm. 27, 157-162 (1967)). The definitions applying in all parts of the invention, i.e. both in the description and in the claims, are as follows:

The letter P in connection with a number from 1 to 3 in normal script, i.e. P1, P2 or P3, is used for amino acid residues and their derivatives in accordance with the Schechter and Berger nomenclature. By contrast, the letter P in connection with a subscript 1 or 2, i.e. $P_1$ or $P_2$, represents amino acid residues and their derivatives as constituents of structure A in formula I of the present invention. In this connection, substituted or unsubstituted natural or unnatural amino acid $P_1$ in the structure A corresponds to P2 according to Schechter and Berger and the substituted or unsubstituted natural or unnatural amino acid $P_2$ in the structure A corresponds to P3 according to Schechter and Berger.

One aspect of the present invention is therefore a compound of the general formula I

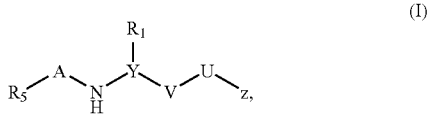

where
A is $P_2$-$P_1$ with

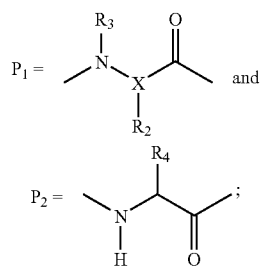

$R_1$ is an H or —$(CH_2)_a COOR_6$ with a=0, 1, 2, 3, 4 or 5, preferably with a=0, 1 or 2, where $R_6$ is a branched or unbranched alkyl radical having, preferably, 1 to 6 C atoms, in particular 1 to 3 C atoms, especially ethyl, and $R_1$ is in particular an H;

$R_2$ is an H, —$CH_2$—$OR_7$ or —$CH_2$—$OCOOR_7$, where $R_7$ is an H or a branched or unbranched alkyl radical having 1-5, in particular 1-3 C atoms, or $R_2$ is a —$CH_2$—$CH_2$—$COOR_{7*}$, where $R_{7*}$ is an H or a branched or unbranched alkyl radical having 1-5 C atoms, preferably ethyl;

$R_3$ is an H;

$R_4$ is —$(CH_2)_f$—$R_8$ with f=0 or 2, preferably with f=2, —$CH_2NHR_8$, —$(CH_2)_2NHR_8$ or —CH═CH—$R_8$, where $R_8$ is a mono- or polysubstituted or unsubstituted cycloalkyl, aryl or heteroaryl radical, where the cycloalkyl, aryl or heteroaryl radical preferably has 5 to 14, in particular 5 to 6 C atoms in the ring and, in the case of the heteroaryl radical, preferably 1 to 3 N as heteroatoms, or if $R_4$ is equal to —$(CH_2)_f$—$R_8$ with $R_8$ equal to a hydroxycycloalkyl radical with 4 to 14, in particular 6 to 10, especially 6 C atoms, then f is 1, and where $P_2$ in the structure A of the general formula I is in the D or L configuration, preferably in the D configuration;

$R_5$ is —$(CH_2)_i$—$COOR_9$ with i=1, 2 or 3, preferably with i=1, and $R_9$ is equal to a branched or unbranched alkyl radical having 1-5 C atoms, preferably ethyl, or $R_5$ is —$SO_2R_{9*}$, —$SO_2$—NH—$R_{9*}$, where $R_{9*}$ is an H, a branched or unbranched alkyl having 1-10, preferably 1 to 6, in particular 1 to 4, especially 1 to 2 C atoms, a mono- or polysubstituted or unsubstituted aryl, heteroaryl, aralkyl, preferably benzyl, heteroaralkyl radical or a cyclohexylalkyl radical, preferably a cyclohexylmethyl radical, where the substituent may be an —OH, —O—$COOR_7$, —$CH_2$—$OCOOR_7$, with $R_7$ as defined above, —$NH_2$, —$NO_2$, —$COOR_{10}$, —$CH_2$—$COOR_{10}$ group or a Cl, F or Br atom, and where $R_{10}$ is an H or an alkyl radical having 1 to 6, in particular having 1 to 4 C atoms, especially ethyl;

U is a phenyl or cyclohexyl radical;
is an aromatic or nonaromatic heterocyclic radical having 1-10, preferably 6 ring atoms having at least one N, S or O as heteroatom, in particular pyridine, piperidine or pyrimidine, or is a thienyl radical;

V is $(CH_2)_n$ with n=0 or 1, preferably 0;
X is N or CH, preferably CH;
Y is N or CH, preferably CH;
Z occurs in position 2, 3 or 4, preferably in position 4, and is an aminomethyl, a guanidino function or an amidino group

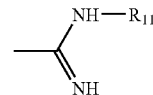

where $R_{11}$ is H, OH, $NH_2$, —$COR_{12}$ or —$COOR_{12}$, where $R_{12}$ is a branched or unbranched alkyl radical having 1 to 8, preferably 1 to 6 C atoms or a mono- or polysubstituted or unsubstituted aryl or heteroaryl, aralkyl or heteroaralkyl radical, where the alkyl radical preferably has 1 to 16, in particular 1 to 8, especially 1 to 4 and particularly preferably 1 to 2 C atoms and the aryl or heteroaryl radical preferably has 4 to 14, in particular 6 to 10, especially 6 C atoms and preferably 1 to 3 N as heteroatoms;

or a compound of the general formula I in the form of a prodrug or in the form of its salt.

Further particularly suitable compounds are compounds of the general formula I where U is substituted at 1, 2 or 3 positions preferably by a halogen, in particular fluorine or chlorine, or a methyl, ethyl, propyl, methoxy, ethoxy or propoxy radical.

Likewise particularly suitable compounds are compounds of the general formula I where at least one carboxyl group is in protected form as ester, preferably as ethyl ester, and is, in the manner of a prodrug, converted into a carboxyl group only after uptake in the body.

Very generally, a prodrug is a pharmaceutically inactive derivative of the appropriate pharmaceutically active substance and, after oral administration, is biotransformed spontaneously or enzymatically to liberate the pharmaceutically active substance.

Consequently, prodrug means for example compounds of the general formula I in which additionally or exclusively one or more carboxyl groups may be present in the form of their alkyl esters with a branched or unbranched alkyl having 1-5 C atoms, preferably ethyl, and/or in which one or more hydroxyl groups may be present in the form of carbonates in which the terminal radical is equal to $R_7$ as defined above. A prodrug within the meaning of the present invention is for example also an amidino- or guanidinobenzylamine derivative of the general formula I in which the amidino- or guanidinobenzylamine residue is in the form of hydroxyamidine or hydroxyguanidine or of alkyloxycarbonyl derivative preferably having a branched or unbranched alkyl radical having 1-5 C atoms, preferably ethyl.

Further particularly suitable compound are compounds in which the structural element

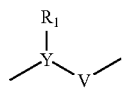

of the formula I is a —$CH_2$— or —NH— group, preferably a —$CH_2$— group.

Also particularly preferred are compounds in which
$R_1$ is an H;
$R_2$ is an H, —$CH_2$—$CH_2$—COOH, —$CH_2$—$CH_2$—COOCH$_2$CH$_3$ or —$CH_2$OH;
$R_3$ is an H;
$R_4$ is a —$(CH_2)_2$—$R_8$, —$CH_2NHR_8$, —$(CH_2)_2NHR_8$ or a —$CH_2$-4-hydroxycyclohexyl radical, where $R_8$ is a mono- or polysubstituted or unsubstituted cycloalkyl, aryl or heteroaryl radical, where the cycloalkyl, aryl or heteroaryl radical has 5 or 6 C atoms and, in the case of a heteroaryl radical, 1 or 2 N as heteroatoms, and $R_8$ is preferably a phenyl, hydroxyphenyl, pyridyl or aminopyridyl radical;
$R_5$ is a methylsulfonyl, ethylsulfonyl, n-propylsulfonyl, isopropylsulfonyl, butylsulfonyl, benzylsulfonyl, n-butylsulfonyl, aminobenzylsulfonyl, hydroxybenzylsulfonyl, chlorobenzylsulfonyl, fluorobenzylsulfonyl, carboxybenzylsulfonyl, ethyloxycarbonylbenzylsulfonyl, carboxymethylbenzylsulfonyl, ethyloxycarbonylmethylbenzylsulfonyl, pyridylmethylsulfonyl, N-(oxide)-pyridylmethylsulfonyl, —$CH_2$—COOH or a —$CH_2COOCH_2CH_3$ radical;
U is a phenyl radical;
V is $(CH_2)_n$ with n=0;
X is CH;
Y is CH;
Z is present in position 4 and is an amidino group

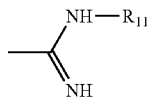

where $R_{11}$ is H, OH or —COOR$_{12}$ with $R_{12}$ a branched or unbranched alkyl radical having 2, 4 or 6 C atoms.

Other particularly suitable compounds are compounds in which $R_4$ is a —$CH_2$—$CH_2$—$R_8$ radical, where $R_8$ is an aryl or heteroaryl radical having 4-6 ring atoms, which has 1 or 2 heteroatoms, preferably N, and may be substituted by one or more —$NH_2$ and/or —OH groups, and preferably $P_2$ in the structure A of the general formula I is derived from a homophenylalanine, homotyrosine, indanylglycine or 4-pyridylhomoalanine, and the $P_2$ amino acid is in particular in the D configuration.

Unless defined otherwise, the term "substituent" or "substituted" according to the present invention preferably means —OH, —$NH_2$, —$NO_2$, —COOH, —COOCH$_2$CH$_3$ or a halogen, where the term "halogen" generally means fluorine, chlorine or bromine, in particular fluorine or chlorine.

An alkyl radical generally designates, unless defined otherwise, a radical preferably having 1-5 C atoms, in particular ethyl, and cycloalkyl, aryl, aralkyl radical generally designates, unless defined otherwise, a radical preferably having 4 to 14, in particular 6 to 10, especially 6 C atoms as ring atoms. The term "hetero" generally means, unless defined otherwise, preferably N, S or O, in particular N, where at least one C atom of the ring in the heteroaryl radical is replaced by a heteroatom, and preferably 1, 2 or 3 C atoms of the ring are replaced in particular by N.

In detail, particularly preferred compounds of the present invention are compounds according to the claims, or compounds 11 to 20 and 22 to 65 in Table 1.

However, the individual particularly preferred compounds also include compounds in which, in the structures mentioned, the glycine residue with the structural element

is in each case replaced by a serine residue with the structural element

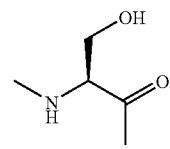

or by a glutamic acid residue with the structural element

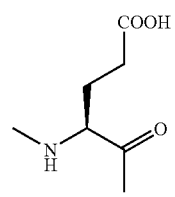

or by a glutamine γ-ethyl ester with the structural element

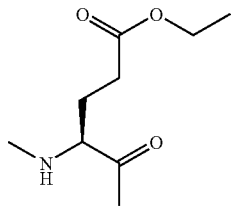

These are for example the following structures having a serine residue:

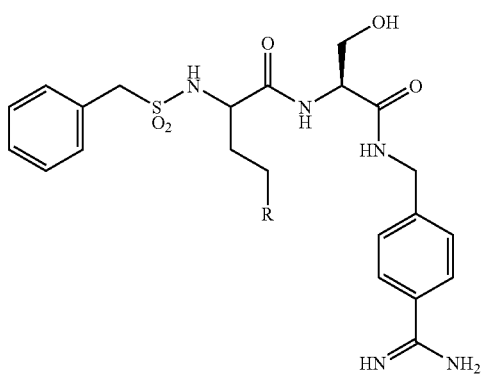

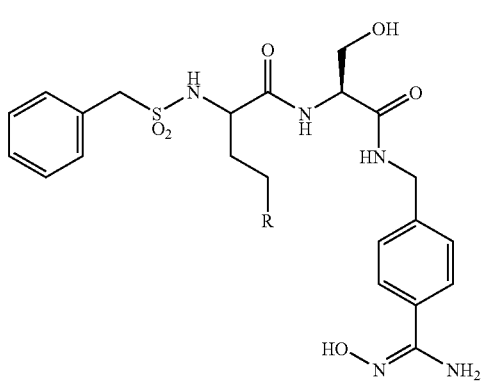

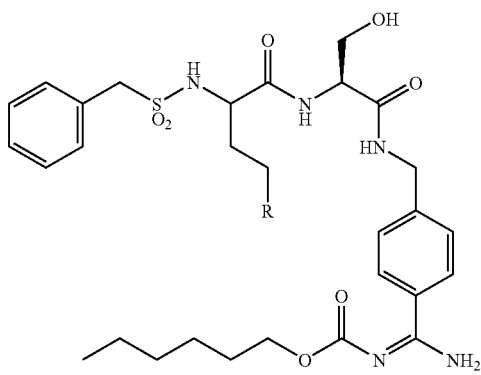

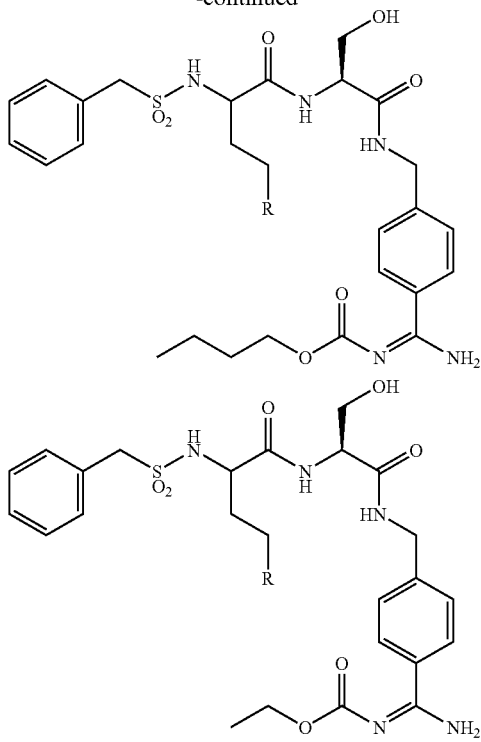

Further suitable compounds of the present invention:

A further aspect of the present invention are compounds as mentioned above where Z is an amino group. U in such compounds is preferably a phenyl radical, a cyclohexyl radical or an N-atom-heteroaryl radical, preferably a pyridyl radical.

A further aspect of the present invention are compounds as mentioned above with the exception that $R_2$ is —$(CH_2)_a$CONHR$_{7*}$ or —$(CH_2)_a$CONHR$_{7}$ with a=1, 2 or 3, where $R_{7}$ is an aryl radical, preferably a phenyl radical or an aralkyl, preferably a benzyl radical, or a heteroaryl radical having one to two N, S or O heteroatoms, preferably N heteroatoms. A further aspect of the present invention are compounds as mentioned above, where $R_2$ is —$(CH_2)_a$CONHR$_{7*}$ or —$(CH_2)_a$CONHR$_{7}$ with a=1, 2, or 3, and where $R_{7}$ is substituted by at least one halogen, one methyl, one ethyl, one amino, one hydroxy, one nitro, one —COOH, one —$CH_2$COOH or one —$CH_2NH_2$— group.

A further aspect of the present invention are compounds as mentioned above, where $R_2$ is a —$(CH_2)_n$—$NH_2$ with n=1, 2, 3, 4 or 5, preferably 1 or 4.

A further aspect of the present invention are compounds as mentioned above, where $R_5R_9$ is H.

A further aspect of the present invention are compounds as mentioned above, where $R_4$ is a —$CH_2$—$SR_8$ or —$CH_2CH_2$—$SR_8$ group. Examples of such compounds are in particular those in which $R_5$ is an —$SO_2R_{9*}$ or an —$SO_2CH_2R_{9*}$ group or in which $R_5$ is an —$SO_2R_{9*}$ or an —$SO_2CH_2R_{9*}$ group and v is $(CH_2)_n$ with n=0 or in which $R_5$ is an —$SO_2R_{9*}$ or an —$SO_2CH_2R_{9*}$ group and v is $(CH_2)_n$ with n=0 and with U=a phenyl radical, a cyclohexyl radical, an N-heteroaryl, preferably pyridyl radical.

Likewise an aspect of the invention are compounds in which $R_5$ is an —$SO_2R_{9*}$ or an —$SO_2CH_2R_{9*}$ group or in which $R_5$ is an —$SO_2R_{9*}$ or an —$SO_2CH_2R_{9*}$ group and v is $(CH_2)_n$ with n=0 or in which $R_5$ is an —$SO_2R_{9*}$ or an —$SO_2CH_2R_{9*}$ group and v is $(CH_2)_n$ with n=0 and U=a phenyl radical, a cyclohexyl radical, an N-heteroaryl, preferably a pyridyl radical, and in which $R_{9*}$ is a phenyl radical, a cyclohexyl radical, a pyridyl radical or a pyridyl N-oxide radical.

Likewise an aspect of the invention are compounds in which $R_5$ is an —$SO_2R_{9*}$ or an —$SO_2CH_2R_{9*}$ group or in which $R_5$ is an —$SO_2R_{9*}$ or —$SO_2CH_2R_{9*}$ group and v is $(CH_2)_n$ with n=0 or in which $R_5$ is an —$SO_2R_{9*}$ or —$SO_2CH_2R_{9*}$ group and v is $(CH_2)_n$ with n=0 and U=a phenyl radical, a cyclohexyl radical, an N-heteroaryl, preferably a pyridyl, radical and in which $R_{9*}$ is a substituted phenyl or cyclohexyl or pyridyl or pyridyl N-oxide radical, where the substituent may be an —OH, —O—$COOR_7$, —$CH_2OCOOR_7$, with $R_7$ as defined above, $NH_2$, $NO_2$, —$COOR_{10}$, —$CH_2COOR_{10}$ group or a Cl or F or Br atom.

Likewise an aspect of the invention are compounds in which $R_5$ is an —$SO_2R_{9*}$ or —$SO_2CH_2R_{9*}$ group or in which $R_5$ is an —$SO_2R_{9*}$ or —$SO_2CH_2R_{9*}$ group and v is $(CH_2)_n$ with n=0 or in which $R_5$ is an —$SO_2R_{9*}$ or —$SO_2CH_2R_{9*}$ group and v is $(CH_2)_n$ with n=0 and U=a phenyl radical, a cyclohexyl radical or an N-heteroaryl, preferably a pyridyl, radical and in which $R_{9*}$ is a substituted phenyl or cyclohexyl or pyridyl or pyridyl N-oxide radical, where the substituent may be an —OH, —O—$COOR_7$, —$CH_2OCOOR_7$, with $R_7$ as defined above, $NH_2$, $NO_2$, —$COOR_{10}$, —$CH_2COOR_{10}$ group or a Cl or F or Br atom, and in which $R_1$ is —$(CH_{-2})_a CONHR_6$ or —$(CH_2)_a CONHR_{6*}$ with a=0, 1, 2, 3, 4 or 5, preferably 0, 1 or 2, where $R_{6*}$ is an aryl radical, preferably a phenyl radical.

Likewise an aspect of the invention are compounds in which $R_5$ is an —$SO_2R_{9*}$ or an —$SO_2CH_2R_{9*}$ group or in which $R_5$ is an —$SO_2R_{9*}$ or —$SO_2CH_2R_{9*}$ group and v is $(CH_2)_n$ with n=0 or in which $R_5$ is an —$SO_2R_{9*}$ or an —$SO_2CH_2R_{9*}$ group and v is $(CH_2)_n$ with n=0 and U=a phenyl radical, a cyclohexyl radical or an N-heteroaryl, preferably a pyridyl, radical and in which $R_{9*}$ is a substituted phenyl or cyclohexyl or pyridyl or pyridyl N-oxide radical, where the substituent may be an —OH, —O—$COOR_7$, —$CH_2OCOOR_7$, with $R_7$ as defined above, an $NH_2$, $NO_2$, —$COOR_{10}$, —$CH_2COOR_{10}$ group or a Cl or F or Br atom, and in which $R_2$ is —$CH_2$—$CH_2$—$CONHR_{7*}$ or —$CH_2CH_2CONHR_{7}$ or —$CH_2CH_2COOR_{7}$, where $R_{7**}$ is an aryl radical, preferably a benzyl or phenyl radical.

Likewise an aspect of the invention are compounds in which $R_5$ is an —$SO_2R_{9*}$ or an —$SO_2CH_2R_{9*}$ group or in which $R_5$ is an —$SO_2R_{9*}$ or an —$SO_2CH_2R_{9*}$ group and v is $(CH_2)_n$ with n=0 or in which $R_5$ is an —$SO_2R_{9*}$ or —$SO_2CH_2R_{9*}$ group and v is $(CH_2)_n$ with n=0 and U=a phenyl radical, a cyclohexyl radical or a pyridyl radical and in which $R_{9*}$ is a substituted phenyl or cyclohexyl or pyridyl radical, where the substituent may be an —OH, —O—$COOR_7$, —$CH_2OCOOR_7$, with $R_7$ as defined above, an $NH_2$, $NO_2$, —$COOR_{10}$, —$CH_2COOR_{10}$ group or a Cl or F or Br atom, and in which $R_4$ is a —$CH_2$—$SR_8$ or —$CH_2CH_2$—$SR_8$ group.

Likewise an aspect of the invention are compounds as mentioned above, where $R_8$ is a pyridyl N-oxide radical.

Also an aspect of the invention are compounds in which $P_1$ is a prolyl radical or an azetidinecarboxylic acid residue.

Likewise an aspect of the invention are compounds in which $P_2$ is a 4-N-oxide-pyridylhomoalanine residue. Also an aspect of the invention are compounds in which $P_2$ is a lysyl or an a,β-diaminopropionic acid residue.

Likewise an aspect of the invention are the compounds one or more or all of the compounds 22 to 65 in table 1.

Besides the inactivation of factor Xa, the additionally charged 4-amidinobenzylamine derivatives of the present invention are, as mentioned above, eliminated very slowly in an advantageous and surprising manner, so that the compounds of the invention represent a novel group of highly active F Xa inhibitors.

The compounds are usually in the form of salts, preferably with mineral acids or suitable organic acids, preferably with hydrochloric acid, sulfuric acid, acetic acid, formic acid, methylsulfonic acid, succinic acid, malic acid or trifluoroacetic acid, especially in the form of their hydrochlorides, sulfates or acetates.

The compounds of the general formula I can be prepared in a manner known in principle as described below, for example as follows, with in general the appropriate amino acids being coupled sequentially onto an amidinobenzylamine which is protected on the amidino group, with the N-terminal amino acid either already carrying the $R_5$ radical or the latter subsequently being linked thereto.

From the commercially available 4-cyanobenzylamine (Showa Denko, Japan), the Boc-protected 4-acetyloxamidinobenzylamine is obtained by methods known to the skilled worker. Elimination of the Boc-protective group is followed by coupling on the further amino acids and the protective group $R_5$ by means of standard coupling methods with Boc as N-terminal protective group. The second amino acid can also be coupled directly as N-arylsulfonyl- or N-aralkylsulfonyl-protected amino acid. The peptide analogs are assembled sequentially starting from acetyloxaminobenzylamine. Most of the intermediates crystallize well and can thus be purified easily. Final purification of the inhibitors takes place at the last stage, preferably by preparative reversed phase HPLC.

The invention therefore further relates to a method for preparing a compound of the general formula I, where the appropriate amino acids are coupled sequentially onto an amidinobenzylamine which is protected on the amidino group, for example onto a 4-acetyloxamidinobenzylamine or onto a 4-(benzyloxycarbonylamidino)benzylamine, with the N-terminal amino acid either already carrying the $R_5$ radical or the latter subsequently being linked thereto.

The invention further relates to a medicament comprising a compound of the invention, and further pharmaceutically suitable excipients and/or additives. Suitable excipients and/or additives, which serve for example to stabilize and/or preserve the medicament, are generally familiar to the skilled worker (e.g. Sucker H. et al., (1991) Pharmazeutische Technologie, 2nd edition, Georg Thieme Verlag, Stuttgart). These include, for example, physiological saline solutions, ringer dextrose, ringer lactate, demineralized water, stabilizers, antioxidants, complexing agents, antimicrobial compounds, proteinase inhibitors and/or inert gases.

The medicament could for example be used in parenteral form, in particular in intraarterial, intravenous, intramuscular or subcutaneous form, in an enteral use form, in particular for oral or rectal use, or in a topical use form, in particular as dermatologic agent. Intravenous or subcutaneous uses are preferred.

In one embodiment of the invention, the medicament is employed for example in the form of a tablet, of a coated tablet, of a capsule, of a pellet, suppository, of a solution, in particular of a solution for injection or infusion, of eyedrops, nose and eardrops, of a syrup, of a capsule, of an emulsion or suspension, of a pessary, stick, aerosol, dusting powder, of a paste, cream or ointment.

The factor Xa inhibitors of the invention or the medicaments mentioned are preferably used for the therapy or prophylaxis of a cardiovascular disorder or of a thromboembolic event, in particular in oral, subcutaneous, intravenous or transdermal form.

The invention is to be explained in more detail below by means of several exemplary embodiments without restricting it.

Methods

Analytical HPLC: Shimadzu LC-10A system, column: Phenomenex-Luna $C_{18}$, 5 μm (250×4 mm) solvents A: 0.1% TFA in water, B: 0.1% TFA in ACN, gradient: 10% B to 70% B in 60 min, 1 ml/min flow rate, detection at 220 or 215 nm.

Preparative HPLC: Shimadzu LC-8A System, column: Phenomenex-Luna $C_{18}$, 5 μm (250×30 mm) solvents A: 0.1% TFA in water, B: 0.1% TFA in ACN, gradient: 5% B to 50% B in 120 min, 10 ml/min flow rate, detection at 220 nm.

Mass spectroscopy: The mass spectra were recorded on an ESI-MS LCQ from Finnigan (Bremen, Germany).

| Abbreviations used | |
|---|---|
| Ac | Acetyl |
| AcOxam | N-(Acetyloxy)amidine |
| Amb | Amidomethylbenzene |
| 4-Amba | 4-Amidinobenzylamide |
| Boc | tert.-Butyloxycarbonyl |
| Bzl | Benzyl |
| Bzls | Benzylsulfonyl |
| dCha | d-βCyclohexylalanine |
| DIEA | Diisopropylethylamine |
| DCM | Dichloromethane |
| DMF | N,N-Dimethylformamide |
| IBCC | Isobutyl chlorocarbonate |
| i.v. | in vacuo |
| MS | Mass spectroscopy |
| NMM | N-Methylmorpholine |
| PyBOP | Benzotriazol-1-yl-N-oxytris(pyrrolidino)phosphonium hexafluorophosphate |
| TEA | Triethylamine |
| TFA | Trifluoroacetic acid |
| THF | Tetrahydrofuran |
| TMS-Cl | Trimethylsilyl chloride |
| tBu | tert.-Butyl |

Example 1

Bzls-D,L-homoAla(4-Pyr)-Gly-4Amba×2 TFA

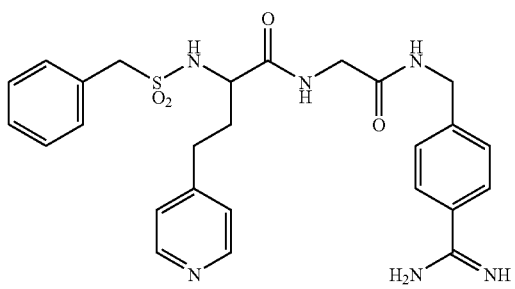 [SMILES: N=C(N)c1ccc(CNC(=O)CNC(=O)C(CCc2ccncc2)NS(=O)(=O)Cc2ccccc2)cc1]

1a) H-Gly-4-(Acetyloxamidino)benzylamide×HCl (H-Gly-Amb(4AcOxam))

2 g (5.49 mmol) of Boc-Gly-4-(acetyloxamidino)benzylamide (prepared as described in WO 01/96286 A2) were mixed with 30 ml of 1 N HCl in glacial acetic acid. The mixture was occasionally shaken. After 45 min, the solvent was concentrated somewhat, and the product was precipitated by adding diethyl ether, filtered off on a frit with suction, washed with ether and dried in vacuo.

Yield: 1.55 g (5.15 mmol), white solid

1b) Boc-D,L-homoAla(4-Pyr)-Gly-Amb(4AcOxam)

250 mg (0.89 mmol) of Boc-D,L-homoAla(4-Pyr)-OH [RSP Amino Acids DBA, Shirley Mass., USA] and 308 mg (1.02 mmol) of product 1a were dissolved in 20 ml of DMF and, at 0° C., 531 mg (1.02 mmol) of PyBop and 533 μl (3.06 mmol) of DIEA were added. The mixture was stirred at 0° C. for 20 min and at room temperature for a further 2 h. The solvent was then removed in vacuo, and the residue was taken up in ethyl acetate, washed 1× with NaCl-saturated water, 2× with saturated NaHCO$_3$ solution and 2× with NaCl-saturated water and dried over Na$_2$SO$_4$. The solvent was removed in vacuo (yellowish oil).

Yield: about 600 mg (crude product), HPLC: 27.89% B

1c) H-D,L-homoAla(4-Pyr)-Gly-Amb(4AcOxam)×HCl 600 mg of crude product 1 b were mixed with 10 ml of 1 N HCl in glacial acetic acid. The mixture was occasionally shaken. After 1 h, the solvent was concentrated somewhat, and the product was precipitated by adding diethyl ether, filtered off on a frit with suction, washed with ether and dried in vacuo.

Yield: 320 mg (0.69 mmol) of pale yellow solid, HPLC: 16.83% B

1d) Bzls-D,L-homoAla(4-Pyr)-Gly-Amb(4AcOxam)

75 mg (0.16 mmol) of crude product 1c and 37 mg (0.19 mmol) of phenylmethanesulfonyl chloride (Bzls-Cl) [Fluka] were dissolved in 10 ml of DMF and, at 0° C., 68 μl (0.39 mmol) of DIEA were added. The mixture was stirred at 0° C. for 20 min and at room temperature for a further 2 h. The solvent was then removed in vacuo, and the residue was taken up in ethyl acetate, washed 1× with NaCl-saturated water, 2× with saturated NaHCO$_3$ solution and 2× with NaCl-saturated water und dried over Na$_2$SO$_4$. The solvent was removed in vacuo (pale oil).

Yield: about 280 mg (crude product), HPLC: 29.27% B

1e) Bzls-D,L-homoAla(4-Pyr)-Gly-4Amba

The crude product 1d was dissolved in 50 ml of 90% acetic acid, and 20 mg of catalyst (10% Pd/C) were added. The mixture was hydrogenated with hydrogen under atmospheric pressure and at room temperature for 5 h. The catalyst was then filtered off, and the solvent was concentrated in vacuo. The remaining residue was dried in vacuo and purified by preparative reversed-phase HPLC and lyophilized.

Yield: 34.6 mg (0.054 mmol) of lyophilized powder, HPLC: 22.97% B

MS: calculated 522.20 (monoisotopic), found 523.4 [M+H]$^+$

Example 2

4-PMs-D,L-homoAla(4-Pyr)-Gly-4Amba×3 Acetate

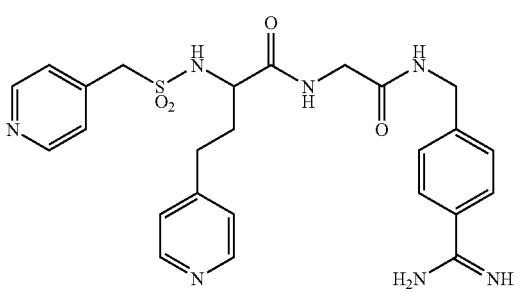 [SMILES: N=C(N)c1ccc(CNC(=O)CNC(=O)C(CCc2ccncc2)NS(=O)(=O)Cc2ccncc2)cc1]

2a) 4-PMs-D,L-homoAla(4-Pyr)-Gly-Amb(4AcOxam)

50 mg (0.11 mmol) of product 1c were suspended in 10 ml of DCM, and 34 µl (0.28 mmol) of chlorotrimethylsilane (=TMS-Cl) [Merck] and 69 µl (0.4 mmol) of DIEA were added, and the mixture was stirred at room temperature for 15 min. Then 41 mg (0.12 mmol) of 4-pyridylmethylsulfonyl chloride×triflate (=4-PMs-Cl) [Array Biopharma, Boulder, Colo., USA] and a further 20 µl (0.11 mmol) of DIEA were added, and stirring was continued at room temperature overnight. The solvent was then removed in vacuo. The residue was employed directly, without further purification, for the next step in the synthesis.

2b) 4-PMs-D,L-homoAla(4-Pyr)-Gly-4Amba

The crude product 2a was dissolved in 50 ml of 90% acetic acid and mixed with 20 mg of catalyst (10% Pd/C). The mixture was hydrogenated with hydrogen under atmospheric pressure and at room temperature overnight. The catalyst was then filtered off, and the solvent was concentrated in vacuo. The remaining residue was dissolved in 5 ml of water and put onto an ion exchange column (Fractogel-EMD COO-column, dimension 16×125 mm, equilibrated with water). The column was washed with 85 ml of water, and then the product was eluted with an ammonium acetate gradient. The product-containing fractions (HPLC monitoring) were combined and lyophilized.

Yield: 20 mg (0.034 mmol) of lyophilized powder, HPLC: 13.14% B

MS: calculated 523.20 (monoisotopic), found 524.3 [M+H]$^+$

Example 3

Bzls-D,L-homoAla(4-Pyr)-Ser-4Amba×2 TFA

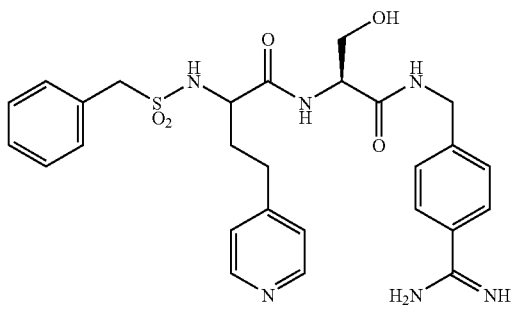 [SMILES: N=C(N)c1ccc(CNC(=O)[C@H](CO)NC(=O)C(CCc2ccncc2)NS(=O)(=O)Cc2ccccc2)cc1]

3a) Boc-4-Cyanobenzylamide 100 g (0.593 mol) of 4-cyanobenzylamine×HCl were dissolved in 1.2 l of dioxane and 600 ml of 2 N NaOH. 142.3 g (0.652 mol) of di(tert-butyl)pyrocarbonates were added in two portions over 10 min at 0° C. The pH was adjusted to 9-10 by adding 2 N NaOH, and the mixture was stirred for a further 4 h. The solvent was removed in vacuo, and the residue was taken up with ethyl acetate, washed 3× each with 5% KHSO$_4$ and NaCl-saturated water and then dried over Na$_2$SO$_4$. The solvent was removed in vacuo (white solid).

Yield: 132.6 g (0.57 mol) of white solid, HPLC: 51.6% B

3b) Boc-4-Acetyloxamidinobenzylamide 130 g (0.56 mol) of product 3a, 58.4 g (0.84 mol) of hydroxylamine×HCl and 146 ml of DIEA were dissolved in 1.5 l of methanol. The mixture was boiled under reflux for 6 h and then stirred at room temperature overnight. The solvent was removed in vacuo, and the oily residue was dissolved in 1.5 l of acetic acid, mixed with 160 ml (1.68 mol) of acetic anhydride and stirred for 30 min. The solvent was removed in vacuo, and the residue was taken up with ethyl acetate and washed 3× with NaCl-saturated water and then dried over Na$_2$SO$_4$. The solvent was removed as far as possible in vacuo, and the product was crystallized from ethyl acetate.

Yield: 110.6 g (0.36 mol) of crystalline solid, HPLC: 39.76% B

3c) H-4-Acetyloxamidinobenzylamine×HCl 50 g (163 mmol) of product 3b were dissolved in 1 l of acetic acid, and 800 ml of 1 N HCl in glacial acetic acid were added. The mixture was shaken and, after a few minutes, the product started to precipitate. After 75 min, the product was filtered off with suction, washed with diethyl ether and dried in vacuo.

Yield: 36 g (147.7 mmol) of white solid, HPLC: 18.97% B

3d) Boc-Ser-4-Acetyloxamidinobenzylamide 25 g (122 mmol) of Boc-Ser-OH were dissolved in 750 ml of DMF and cooled to −15° C. 13.42 ml (122 mmol) of N-methylmorpholine and 15.86 ml (122 ml) of isobutyl chlorocarbonate were added, and the mixture was stirred for 10 min. Then 29.74 g (122 mmol) of product 3c and 13.42 ml (122 mmol) of N-methylmorpholine were added, and the mixture was stirred at −15° C. for 1 h and at room temperature overnight. The DMF was then removed in vacuo, and the residue was dissolved in 2 l of ethyl acetate and washed 2× with 300 ml of saturated NaHCO$_3$ solution and 300 ml of NaCl-saturated water and dried over Na$_2$SO$_4$, and the solvent was removed in vacuo (oil).

Yield: 43 g of crude product oil, HPLC: 29.87% B

3e) H-Ser-4-Acetyloxamidinobenzylamide×TFA 40 g of the oily crude product 3d were mixed with 200 ml of trifluoroacetic acid and stirred for 1 h. The product was precipitated by adding diethyl ether, filtered off with suction, washed with diethyl ether and dried in vacuo.

Yield: 27 g (66 mmol) of white solid, HPLC: 20.22% B

3f) Boc-D,L-homoAla(4-Pyr)-Ser-Amb(4AcOxam)

100 mg (0.36 mmol) of Boc-D,L-homoAla(4-Pyr)-OH [RSP Amino Acids DBA, Shirley Mass., USA] and 161 mg (0.4 mmol) of crude product 3e were dissolved in 15 ml of DMF and, at 0° C., 206 mg (0.4 mmol) of PyBop and 207 µl (1.2 mmol) of DIEA were added. The mixture was stirred at 0° C. for 20 min and at room temperature for a further 2 h. The solvent was then removed in vacuo, and the residue was taken up in ethyl acetate, washed 1× with NaCl-saturated water, 2× with saturated NaHCO$_3$ solution and 2× with NaCl-saturated water and dried over Na$_2$SO$_4$. The solvent was removed in vacuo (pale oil).

Yield: about 300 mg (crude product), HPLC: 26.8% B and 27.4% B (double peak, racemate)

3g) H-D,L-homoAla(4-Pyr)-Ser-Amb(4AcOxam)×TFA 300 mg of crude product from 3f were mixed with 5 ml of 50% TFA in dichloromethane. The mixture was shaken occasionally. After 45 min, the solvent was concentrated, the residue was solubilized in methanol, and the product was precipitated by adding diethyl ether, filtered off with suction on a frit, washed with ether and dried in vacuo.

Yield: 186 mg (0.33 mmol) of white solid, HPLC: 21.6% B and 22.7% B (double peak, racemate)

3h) Bzls-D,L-homoAla(4-Pyr)-Ser-Amb(4AcOxam)

75 mg (0.13 mmol) of product 3g and 38 mg (0.2 mmol) of phenylmethanesulfonyl chloride (=Bzls-Cl) [Fluka] were dissolved in 10 ml of DMF and, at 0° C., 68 µl (0.39 mmol) of DIEA were added. The mixture was stirred at 0° C. for 20 min and at room temperature overnight. The solvent was removed in vacuo (oil).

Yield: about 120 mg (crude product), HPLC: 28.1% B and 28.6% B (double peak)

3i) Bzls-D,L-homoAla(4-Pyr)-Ser-4Amba×2 TFA

The crude product from 3h was dissolved in 50 ml of 90% acetic acid, and 20 mg of catalyst (10% Pd/C) were added. The mixture was hydrogenated with hydrogen under atmospheric pressure and at room temperature overnight. The catalyst was then filtered off, and the solvent was concentrated in vacuo. The remaining residue was dried in vacuo and purified by preparative reversed phase HPLC and lyophilized. It was possible to separate the diastereomers thereby.

HPLC: 22.01% B (compound 3a) and 22.6% B (compound 3b).

MS: calculated 552.22 (monoisotopic), found 553.5 [M+H]$^+$

Example 4

4-PMs-D,L-homoAla(4-Pyr)-Ser-4Amba×3 acetate

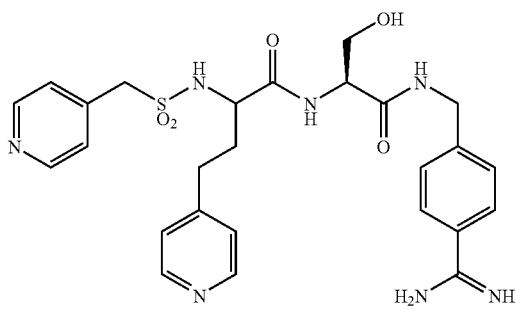 [SMILES: N=C(N)c1ccc(CNC(=O)[C@H](CO)NC(=O)C(CCc2ccncc2)NS(=O)(=O)Cc2ccncc2)cc1]

4a) 4-PMs-D,L-homoAla(4-Pyr)-Ser-Amb(4AcOxam)

55 mg (0.1 mmol) of product 3g was suspended in 10 ml of DCM, and 31 µl (0.25 mmol) of chlorotrimethylsilane (=TMS-Cl) [Merck] and 61 µl (0.36 mmol) of DIEA were added, and the mixture was stirred at room temperature for 15 min. Then 36 mg (0.105 mmol) of 4-pyridylmethylsulfonyl chloride×triflate (=4-PMs-Cl) [Array Biopharma, Boulder, Colo., USA] and a further 17.5 µl (0.1 mmol) of DIEA were added, and stirring was continued at room temperature overnight. The solvent was then removed in vacuo. The residue was employed directly, without further purification, for the next step in the synthesis.

4b) 4-PMs-D,L-homoAla(4-Pyr-Ser-4Amba×3 acetate

The crude product from 4a was dissolved in 50 ml of 90% acetic acid, and 20 mg of catalyst (10% Pd/C) were added. The mixture was hydrogenated with hydrogen under atmospheric pressure and at room temperature overnight. The catalyst was then filtered off, and the solvent was concentrated in vacuo. The remaining residue was dissolved in 5 ml of water and put onto an ion exchange column (Fractogel-EMD COO column, dimension 16×125 mm, equilibrated with water). The column was washed with 85 ml of water and then the product was eluted with an ammonium acetate gradient. The product-containing fractions were combined and lyophilized.

Yield: 17.2 mg (0.028 mmol) of lyophilized powder, HPLC: 12.1 and 12.3% B (double peak, racemate)

MS: calculated 553.21 (monoisotopic), found 554.5 [M+H]$^+$

Example 5

Bzls-d-homoTyr-Gly-4Amba×TFA

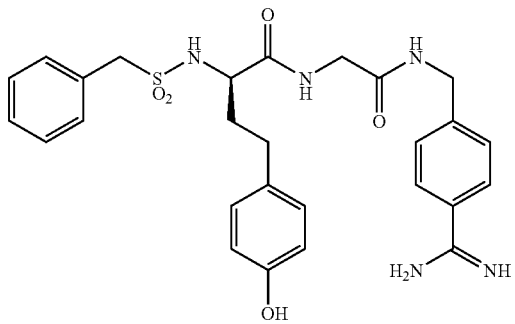 [SMILES: N=C(N)c1ccc(CNC(=O)CNC(=O)[C@@H](CCc2ccc(O)cc2)NS(=O)(=O)Cc2ccccc2)cc1]

5a) Bzls-d-homoTyr-OH 300 mg (1.09 mmol) of H-d-homoTyr-OH×HBr [ChemImpex International, Wood Dale, Ill., USA] were suspended in 20 ml of DCM, and 425 µl (3.37 mmol) of chlorotrimethylsilane (=TMS-Cl) [Merck] and 586 µl (3.37 mmol) of DIEA were added, and the mixture was stirred under reflux at 60° C. for 1 h and then cooled again to room temperature. Subsequently, 229 mg (1.2 mmol) of phenylmethanesulfonyl chloride (=Bzls-Cl) [Fluka] and a further 190 µl (1.09 mmol) of DIEA were added, and the mixture was stirred at room temperature for 2 h. The solvent was removed in vacuo, and the residue was taken up in ethyl acetate, washed 1× with 5% KHSO$_4$ solution and 2× with NaCl-saturated water and dried over Na$_2$SO$_4$. After removal of the solvent, the product was crystallized from ethyl acetate.

Yield: 353 mg (1.01 mmol) of pale yellow solid, HPLC: 40.9% B

5b) Bzls-d-homoTyr-Gly-Amb(4AcOxam)

50 mg (0.14 mmol) of product 5a and 43 mg (0.14 mmol) of H-Gly-Amb(4AcOxam) (=product 1a) were dissolved in 15 ml of DMF and, at 0° C., 74.4 mg (0.14 mmol) of PyBop and 74.6 µl (0.43 mmol) of DIEA were added. The mixture was stirred at 0° C. for 20 min and at room temperature for a further 2 h. The solvent was then removed in vacuo, and the residue was taken up in ethyl acetate, washed 1× with 5% KHSO$_4$ solution and 2× with NaCl-saturated water and dried over Na$_2$SO$_4$. A pale oil remained as residue.

Yield: about 200 mg (crude product), HPLC: 39.84% B

5c) Bzls-d-homoTyr-Gly-4Amba

The crude product from 5b was dissolved in 50 ml of 90% acetic acid, and 20 mg of catalyst (10% Pd/C) were added. The mixture was hydrogenated with hydrogen under atmospheric pressure and at room temperature for 6 h. The catalyst was then filtered off, and the solvent was concentrated in vacuo. The remaining residue was dried in vacuo and, without further prepurification, purified by preparative reversed phase HPLC and lyophilized.

Yield: 37.5 mg (0.058 mmol) of lyophilized powder, HPLC: 32.37% B

MS: calculated 537.20 (monoisotopic), found 538.4 [M+H]$^+$

Example 6

Bzls-d-homoTyr-Ser-4Amba×TFA

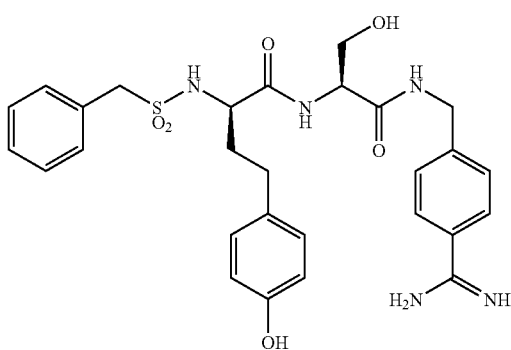 [SMILES: N=C(N)c1ccc(CNC(=O)[C@H](CO)NC(=O)[C@@H](CCc2ccc(O)cc2)NS(=O)(=O)Cc2ccccc2)cc1]

6a) Bzls-d-homoTyr-Ser-Amb(4AcOxam)

50 mg (0.14 mmol) of product 5a and 58.4 mg (0.14 mmol) of H-Ser-Amb(4AcOxam) (=product 3e) were dissolved in 15 ml of DMF and, at 0° C., 74.4 mg (0.14 mmol) of PyBop and 74.6 µl (0.43 mmol) of DIEA were added. The mixture was stirred at 0° C. for 20 min and at room temperature overnight. The solvent was then removed in vacuo, and the residue was taken up in ethyl acetate, washed 1× with 5% KHSO$_4$ solution and 2× with NaCl-saturated water and dried over Na$_2$SO$_4$ (pale oil).

Yield: about 165 mg (crude product), HPLC: 38.49% B

6b) Bzls-d-homoTyr-Ser-4Amba×TFA

The crude product from 6a was dissolved in 50 ml of 90% acetic acid, and 20 mg of catalyst (10% Pd/C) were added. The mixture was hydrogenated with hydrogen under atmospheric pressure and at room temperature for 6 h. The catalyst was then filtered off, and the solvent was concentrated in vacuo. The remaining residue was dried in vacuo and, without further prepurification, purified by preparative reversed phase HPLC and lyophilized.

Yield: 38 mg (0.056 mmol) of lyophilized powder, HPLC: 31.74% B

MS: calculated 567.22 (monoisotopic), found 568.5 [M+H]$^+$

Example 7

4-PMs-dhomoPhe-Gly-4Amba×2 TFA

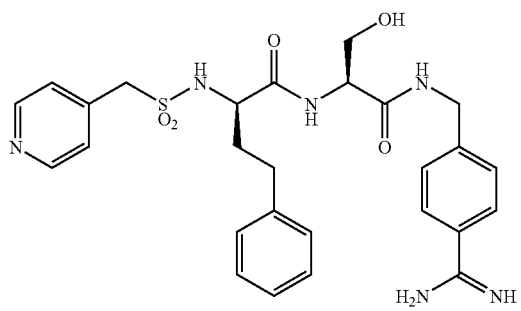 [SMILES: N=C(N)c1ccc(CNC(=O)[C@H](CO)NC(=O)[C@@H](CCc2ccccc2)NS(=O)(=O)Cc2ccncc2)cc1]

7a) Boc-d-homoPhe-Gly-Amb(4AcOxam)

732 mg (2.62 mmol) of Boc-d-homoPhe-OH [Bachem] and 788 mg (2.62 mmol) of H-Gly-Amb(4AcOxam) (=product 1a) were dissolved in 50 ml of DMF and, at 0° C., 1.36 g (2.62 mmol) of PyBop and 1.37 ml (7.86 mmol) of DIEA were added. The mixture was stirred at 0° C. for 20 min and at room temperature for 2 h. The solvent was then removed in vacuo, and the residue was taken up in ethyl acetate, washed 2× each with 5% KHSO$_4$, saturated NaHCO$_3$ solution and NaCl-saturated water and then dried over Na$_2$SO$_4$. The solvent was removed in vacuo (pale brown oil).

Yield: about 1.8 g (crude product), HPLC: 47.87% B

7b) H-d-homoPhe-Gly-Amb(4AcOxam)×HCl 600 mg of crude product from 7a were mixed with 15 ml of 1 N HNC in glacial acetic acid. The mixture was shaken occasionally. After 1 h, the solvent was concentrated somewhat and the product was precipitated by adding diethyl ether, filtered off with suction on a frit, washed with ether and dried in vacuo.

Yield: 1.02 g (2.2 mmol) of pale yellow solid, HPLC: 28.11% B 7c) 4-PMs-dhomoPhe-Gly-Amb(4AcOxam)

50 mg (0.11 mmol) of product 7b were suspended in 10 ml of DCM, and 20.5 µl (0.16 mmol) of chlorotrimethylsilane (=TMS-Cl) [Merck] and 49 µl (0.28 mmol) of DIEA were added, and the mixture was stirred at room temperature for 15 min. Then 41 mg (0.12 mmol) of 4-pyridylmethylsulfonyl chloride×triflate (=4-PMs-Cl) [Array Biopharma, Boulder, Colo., USA] and a further 20 µl (0.11 mmol) of DIEA were added, and stirring was continued at room temperature for 2 h. The solvent was then removed in vacuo. The residue was employed directly, without further purification, for the next step in the synthesis.

7d) 4-PMs-dhomoPhe-Gly-4Amba×2 TFA

The crude product from 7c was dissolved in 50 ml of 90% acetic acid, and 20 mg of catalyst (10% Pd/C) were added. The mixture was hydrogenated with hydrogen under atmospheric pressure and at room temperature overnight. The catalyst was then filtered off, and the solvent was concentrated in vacuo. The remaining residue was dried in vacuo and, without further prepurification, purified by preparative reversed phase HPLC and lyophilized.

Yield: 30 mg (0.047 mmol) of lyophilized powder, HPLC: 26.01% B

MS: calculated 522.20 (monoisotopic), found 523.3 [M+H]$^+$

Example 8

2-PMs-d-homoPhe-Gly-4Amba×2 TFA

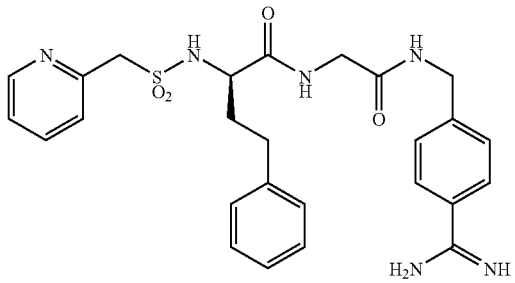 [SMILES: N=C(N)c1ccc(CNC(=O)CNC(=O)[C@@H](CCc2ccccc2)NS(=O)(=O)Cc2ccccn2)cc1]

8a) 2-PMs-dhomoPhe-OH 75 mg (0.42 mmol) of H-d-homoPhe-OH [Bachem] were suspended in 10 ml of DCM, and 116 µl (0.92 mmol) of chlorotrimethylsilane (=TMS-Cl) [Merck] and 160 µl (0.92 mmol) of DIEA were added, and the mixture was stirred under reflux at 60° C. for 1 h and then cooled again to room temperature. Then 150 mg (0.44 mmol) of 2-pyridylmethylsulfonyl chloride×triflate (=2-PMs-Cl) [Array Biopharma, Boulder, Colo., USA] and a further 77 µl (0.44 mmol) of DIEA were added, and stirring was continued at room temperature overnight. The solvent was then removed. The residue was employed directly, without further purification, for the next step in the synthesis.

Yield: about 300 mg crude product, HPLC: 32.86% B

8b) 2-PMs-dhomoPhe-Gly-Amb(4AcOxam)

150 mg (about 0.2 mmol) of crude product 8a and 60.2 mg (0.2 mmol) of H-Gly-Amb(4AcOxam) (=product 1a) were dissolved in 10 ml of DMF and, at 0° C., 104 mg (0.2 mmol) of PyBop and 104.5 µl (0.6 mmol) of DIEA were added. The mixture was stirred at 0° C. for 20 min and at room temperature for a further 2 h. The solvent was then removed in vacuo, and the residue was taken up in ethyl acetate, washed 2× with saturated $NaHCO_3$ solution and 2× with NaCl-saturated water and dried over $Na_2SO_4$. The solvent was removed in vacuo (pale brown oil).

HPLC: 35.28% B

8c) 2-PMs-dhomoPhe-Gly-4Amba

The crude product from 8b was dissolved in 50 ml of 90% acetic acid, and 20 mg of catalyst (10% Pd/C) were added. The mixture was hydrogenated with hydrogen under atmospheric pressure and at room temperature for 5 h. The catalyst was then filtered off, and the solvent was concentrated in vacuo. The remaining residue was dried in vacuo and, without further prepurification, purified by preparative reversed phase HPLC, and the product was lyophilized.

Yield: 69 mg (0.11 mmol) of lyophilized powder, HPLC: 31.18% B

MS: calculated 522.20 (monoisotopic), found 523.4 $[M+H]^+$

Example 9

3-PMs-dhomoPhe-Gly-4Amba×2 TFA

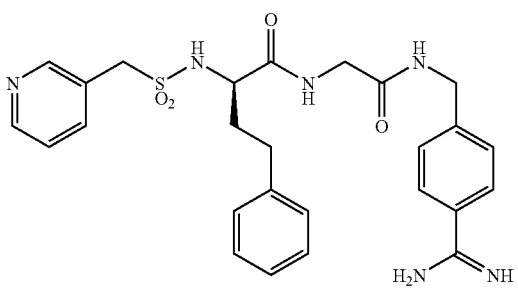

9) 3-PMs-dhomoPhe-Gly-4Amba

Example 9 was synthesized in analogy to example 8 but using 3-pyridylmethylsulfonyl chloride×triflate (=3-PMs-Cl) [Array Biopharma, Boulder, Colo., USA]. The final product was purified by preparative reversed phase HPLC and lyophilized.

Yield: 62 mg (0.097 mmol) of lyophilized powder, HPLC: 29.08% B

MS: calculated 522.20 (monoisotopic), found 523.4 $[M+H]^+$

TABLE 1

Determination of the inhibitory constants for factor Ca and thrombin. Also indicated is the selectivity ratio SR (SR = $K_{i\ thrombin}/K_{i\ factor\ Xa}$).

| | | $K_i$ (µM) | | |
| --- | --- | --- | --- | --- |
| No. | Structure | Factor Xa | Thrombin | SR |
| 10 | | 0.026 | 0.068 | 2.6 |

TABLE 1-continued

Determination of the inhibitory constants for factor Ca and thrombin. Also indicated is the selectivity ratio SR (SR = $K_{i\ thrombin}/K_{i\ factor\ Xa}$).

| No. | Structure | $K_i$ (μM) Factor Xa | Thrombin | SR |
|---|---|---|---|---|
| 11 | 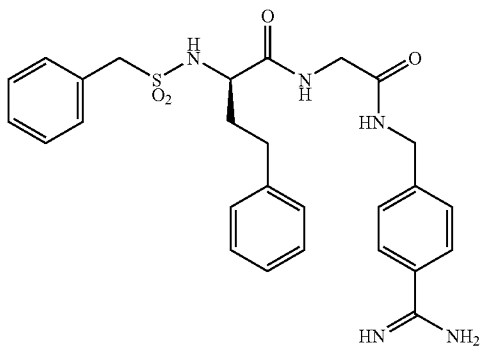 [SMILES: N=C(N)c1ccc(CNC(=O)CNC(=O)[C@@H](CCc2ccccc2)NS(=O)(=O)Cc2ccccc2)cc1] | 0.0065 | 0.047 | 7.2 |
| 12 | 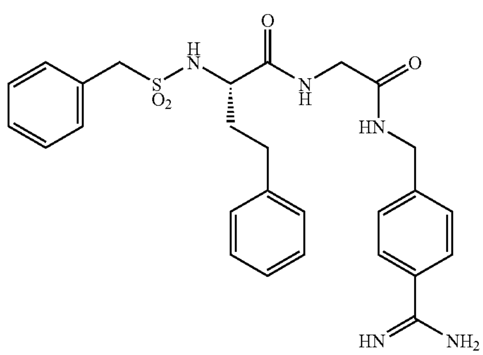 [SMILES: N=C(N)c1ccc(CNC(=O)CNC(=O)[C@H](CCc2ccccc2)NS(=O)(=O)Cc2ccccc2)cc1] | 0.36 | 11 | 31 |
| 13 | 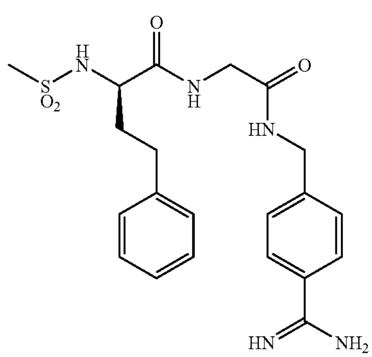 [SMILES: CS(=O)(=O)N[C@H](CCc1ccccc1)C(=O)NCC(=O)NCc1ccc(C(=N)N)cc1] | 1.1 | 1.3 | 1.2 |
| 8 | 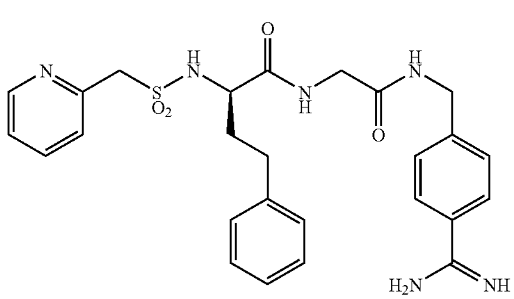 [SMILES: N=C(N)c1ccc(CNC(=O)CNC(=O)[C@@H](CCc2ccccc2)NS(=O)(=O)Cc2ccccn2)cc1] | 0.051 | 4.9 | 96 |

TABLE 1-continued
Determination of the inhibitory constants for factor Ca and thrombin. Also indicated is the selectivity ratio SR (SR = $K_{i\ thrombin}/K_{i\ factor\ Xa}$).
| No. | Structure | $K_i$ (μM) Factor Xa | Thrombin | SR |
|---|---|---|---|---|
| 9 | 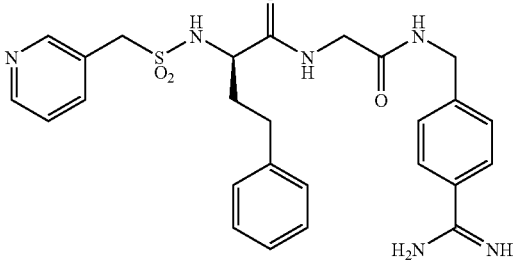 | 0.062 | 5.9 | 95 |
| 14 | 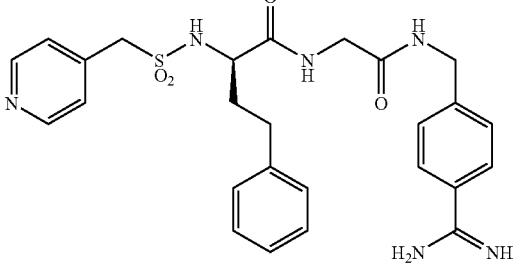 | 0.08 | 3.6 | 45 |
| 15 | 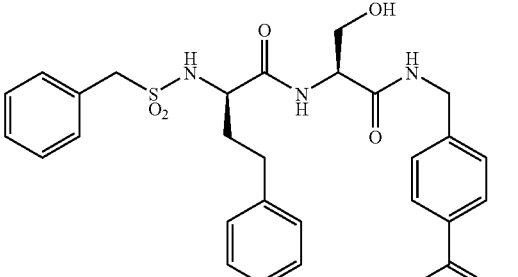 | 0.04 | 0.6 | 15 |
| 7 | 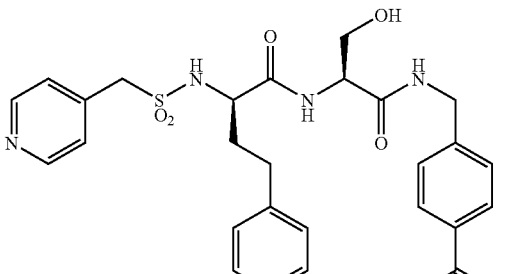 | 0.46 | 3.3 | 7.2 |
| 16 | 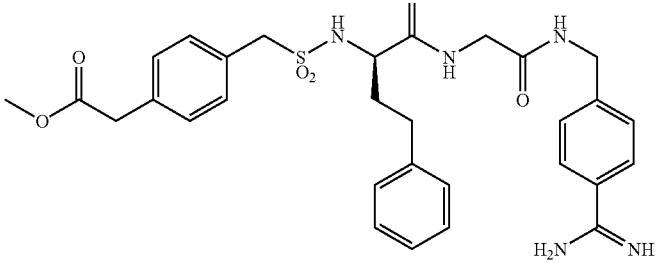 | 0.038 | 1.8 | 47 |

TABLE 1-continued

Determination of the inhibitory constants for factor Ca and thrombin. Also indicated is the selectivity ratio SR (SR = $K_{i\ thrombin}/K_{i\ factor\ Xa}$).

| No. | Structure | $K_i$ (μM) Factor Xa | Thrombin | SR |
|---|---|---|---|---|
| 17 | 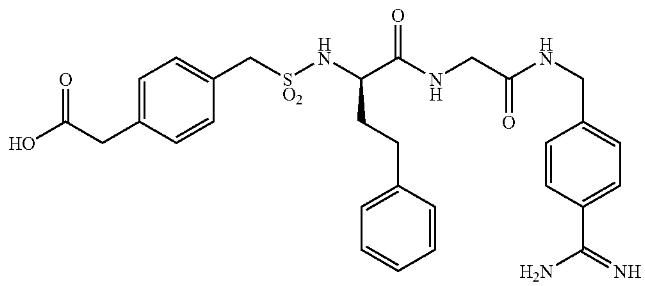 [SMILES: N=C(N)c1ccc(CNC(=O)CNC(=O)[C@@H](CCc2ccccc2)NS(=O)(=O)Cc2ccc(CC(=O)O)cc2)cc1] | 0.054 | 14 | 259 |
| 18 | 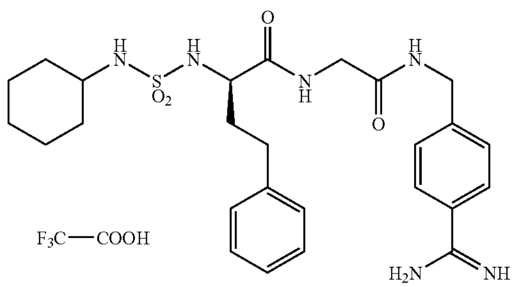 [SMILES: N=C(N)c1ccc(CNC(=O)CNC(=O)[C@@H](CCc2ccccc2)NS(=O)(=O)NC2CCCCC2)cc1 ; O=C(O)C(F)(F)F] | 0.11 | 5.4 | 49 |
| 19 | 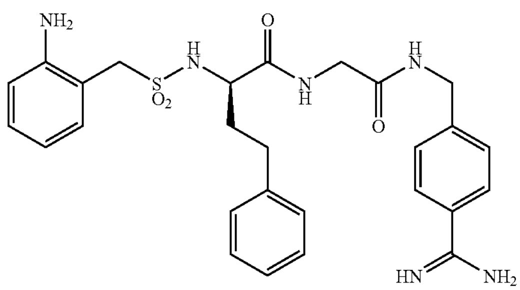 [SMILES: N=C(N)c1ccc(CNC(=O)CNC(=O)[C@@H](CCc2ccccc2)NS(=O)(=O)Cc2ccccc2[N+](=O)[O-])cc1] | 0.0067 | 0.92 | 137 |
| 20 | 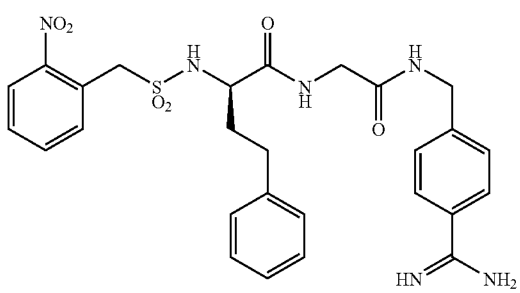 | 0.026 | 1.2 | 46 |
| 5 | 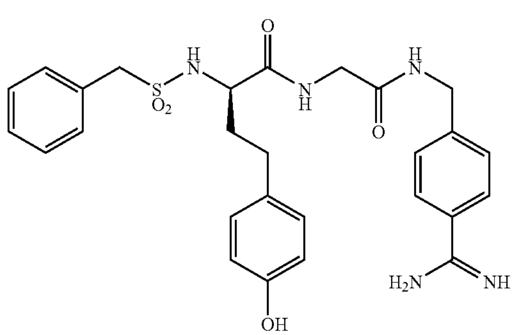 [SMILES: N=C(N)c1ccc(CNC(=O)CNC(=O)[C@@H](CCc2ccc(O)cc2)NS(=O)(=O)Cc2ccccc2)cc1] | 0.0027 | 1.5 | 556 |

TABLE 1-continued
Determination of the inhibitory constants for factor Ca and thrombin. Also indicated is the selectivity ratio SR (SR = $K_{i\,thrombin}/K_{i\,factor\,Xa}$).
| No. | Structure | $K_i$ (μM) Factor Xa | Thrombin | SR |
|---|---|---|---|---|
| 6 | 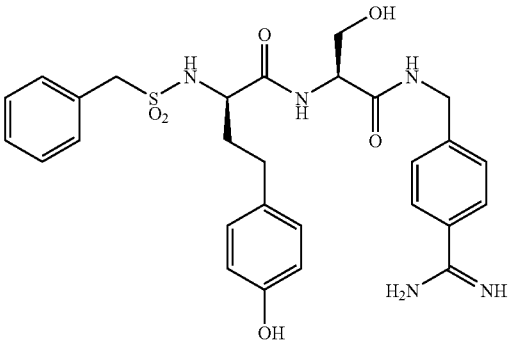 [SMILES: N=C(N)c1ccc(CNC(=O)[C@H](CO)NC(=O)[C@@H](CCc2ccc(O)cc2)NS(=O)(=O)Cc2ccccc2)cc1] | 0.019 | 1.4 | 74 |
| 1 | 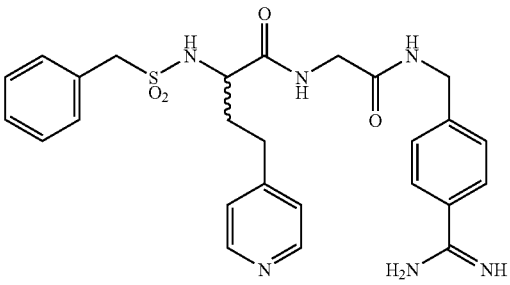 [SMILES: N=C(N)c1ccc(CNC(=O)CNC(=O)C(CCc2ccncc2)NS(=O)(=O)Cc2ccccc2)cc1] | 0.0029 | 2 | 690 |
| 2 | 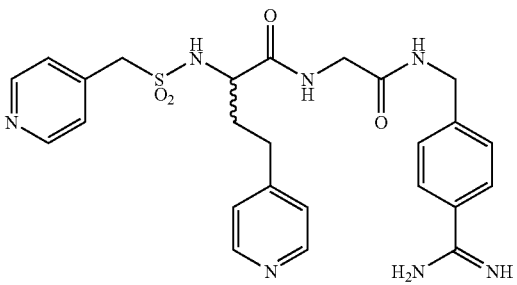 [SMILES: N=C(N)c1ccc(CNC(=O)CNC(=O)C(CCc2ccncc2)NS(=O)(=O)Cc2ccncc2)cc1] | 0.013 | 3.2 | 246 |
| 3a | 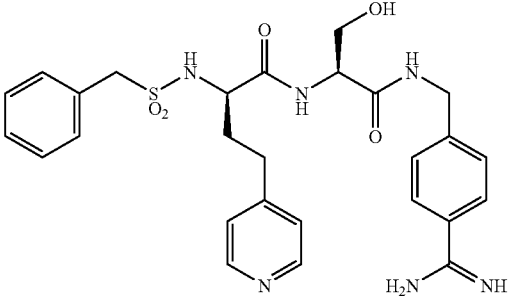 [SMILES: N=C(N)c1ccc(CNC(=O)[C@H](CO)NC(=O)[C@@H](CCc2ccncc2)NS(=O)(=O)Cc2ccccc2)cc1] | 0.0094 | 0.91 | 97 |

TABLE 1-continued
Determination of the inhibitory constants for factor Ca and thrombin. Also indicated is the selectivity ratio SR (SR = $K_{i\ thrombin}/K_{i\ factor\ Xa}$).
| No. | Structure | $K_i$ (μM) Factor Xa | Thrombin | SR |
|---|---|---|---|---|
| 3b | 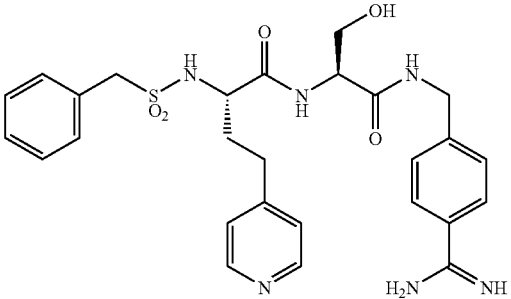 | 0.095 | 4.6 | 48.4 |
| 4 | 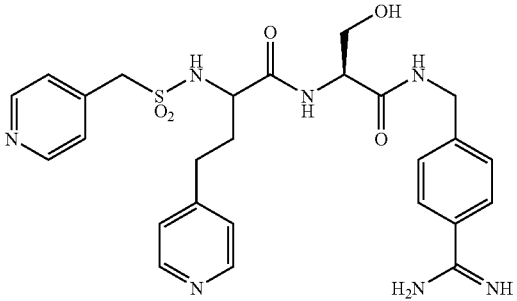 [SMILES: N=C(N)c1ccc(CNC(=O)[C@H](CO)NC(=O)C(CCc2ccncc2)NS(=O)(=O)Cc2ccncc2)cc1] | 0.097 | 6.3 | 65 |
| 21 | 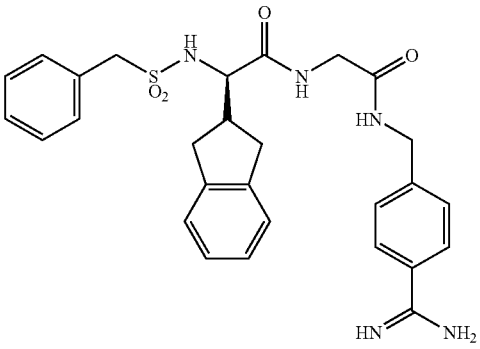 [SMILES: N=C(N)c1ccc(CNC(=O)CNC(=O)[C@H](NS(=O)(=O)Cc2ccccc2)C2Cc3ccccc3C2)cc1] | 0.029 | 0.15 | 5.2 |
| 22 | 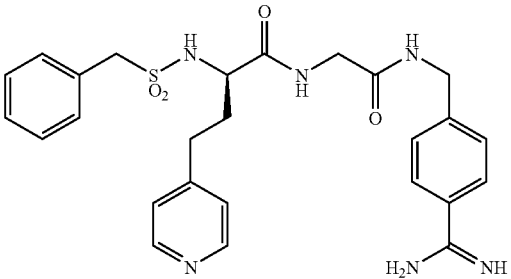 [SMILES: N=C(N)c1ccc(CNC(=O)CNC(=O)[C@@H](CCc2ccncc2)NS(=O)(=O)Cc2ccccc2)cc1] | 0.0027 | 0.7 | 259 |

TABLE 1-continued
Determination of the inhibitory constants for factor Ca and thrombin. Also indicated is the selectivity ratio SR (SR = $K_{i\ thrombin}/K_{i\ factor\ Xa}$).
| No. | Structure | $K_i$ (μM) Factor Xa | Thrombin | SR |
|---|---|---|---|---|
| 23 | 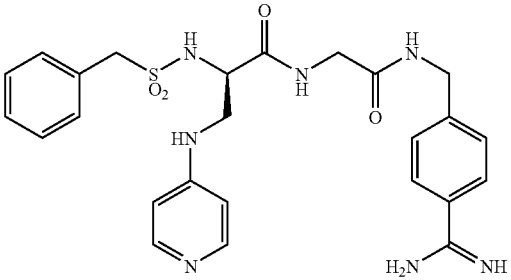 [SMILES: N=C(N)c1ccc(CNC(=O)CNC(=O)[C@@H](CNc2ccncc2)NS(=O)(=O)Cc2ccccc2)cc1] | 0.022 | 2.8 | 127 |
| 24 | 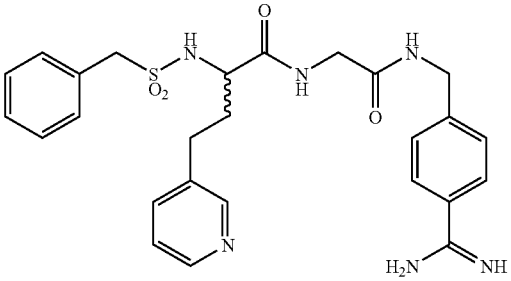 [SMILES: N=C(N)c1ccc(CNC(=O)CNC(=O)C(CCc2cccnc2)NS(=O)(=O)Cc2ccccc2)cc1] | 0.005 | 2.0 | 400 |
| 25 | 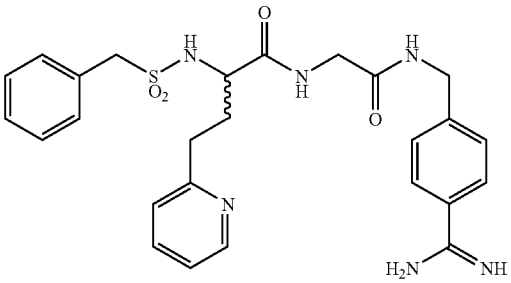 [SMILES: N=C(N)c1ccc(CNC(=O)CNC(=O)C(CCc2ccccn2)NS(=O)(=O)Cc2ccccc2)cc1] | 0.0021 | 2.0 | 952 |
| 26 | 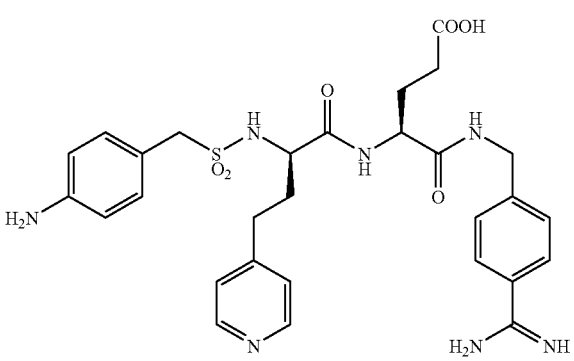 | 0.0017 | 25 | 14705 |

TABLE 1-continued

*Determination of the inhibitory constants for factor Ca and thrombin. Also indicated is the selectivity ratio SR (SR = $K_{i\ thrombin}/K_{i\ factor\ Xa}$).*

| No. | Structure | $K_i$ (μM) Factor Xa | Thrombin | SR |
|-----|-----------|----------------------|----------|-----|
| 27  | 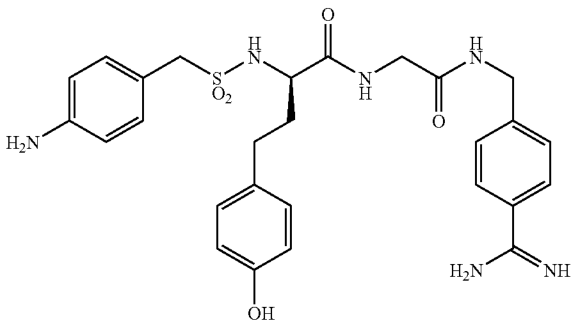          | 0.0019 | 0.56 | 295 |
| 28  | 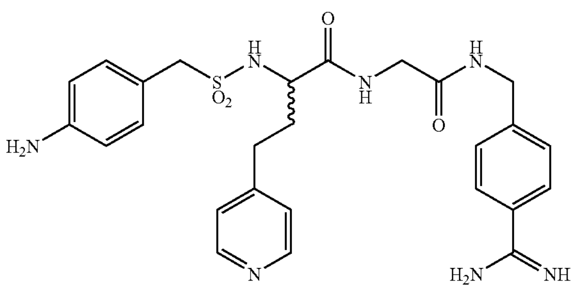          | 0.0022 | 1    | 454 |
| 29  | 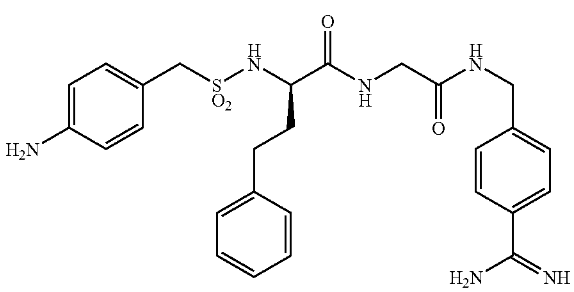 [SMILES: N=C(N)c1ccc(CNC(=O)CNC(=O)[C@@H](CCc2ccccc2)NS(=O)(=O)Cc2ccc(N)cc2)cc1]          | 0.0026 | 0.26 | 100 |
| 30  | 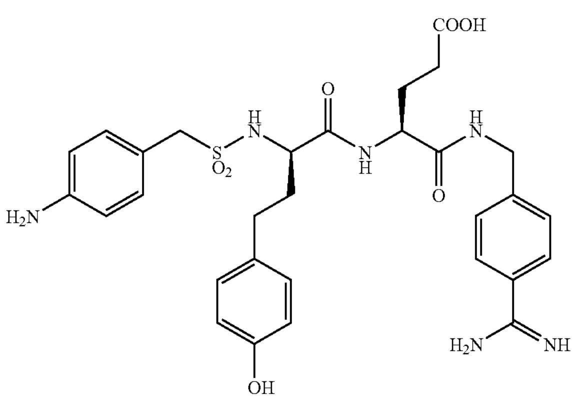 [SMILES: N=C(N)c1ccc(CNC(=O)[C@H](CCC(=O)O)NC(=O)[C@@H](CCc2ccc(O)cc2)NS(=O)(=O)Cc2ccc(N)cc2)cc1]          | 0.0034 | 78   | 22940 |

TABLE 1-continued

Determination of the inhibitory constants for factor Ca and thrombin. Also indicated is the selectivity ratio SR (SR = $K_{i\,thrombin}/K_{i\,factor\,Xa}$).

| No. | Structure | $K_i$ (μM) Factor Xa | Thrombin | SR |
|---|---|---|---|---|
| 31 | | 0.0035 | 1.9 | 543 |
| 32 | | 0.0036 | 0.38 | 105 |
| 33 | | 0.0036 | 100 | 27778 |
| 34 | | 0.0037 | 19 | 5135 |

TABLE 1-continued
Determination of the inhibitory constants for factor Ca and thrombin. Also indicated is the selectivity ratio SR (SR = $K_{i\ thrombin}/K_{i\ factor\ Xa}$).
| No. | Structure | $K_i$ (μM) Factor Xa | $K_i$ (μM) Thrombin | SR |
|---|---|---|---|---|
| 35 | 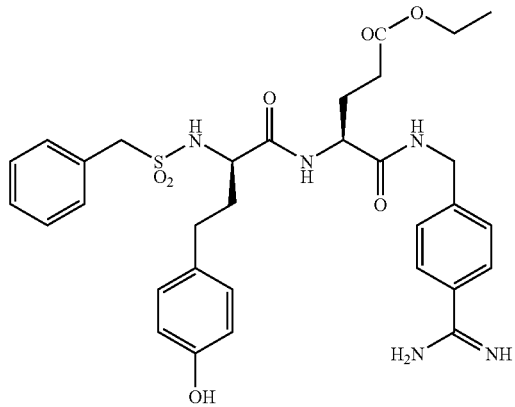 | 0.005 | 1 | 200 |
| 36 | 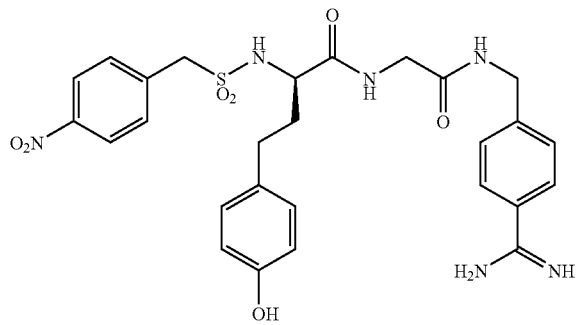 | 0.0052 | 0.86 | 165 |
| 37 | 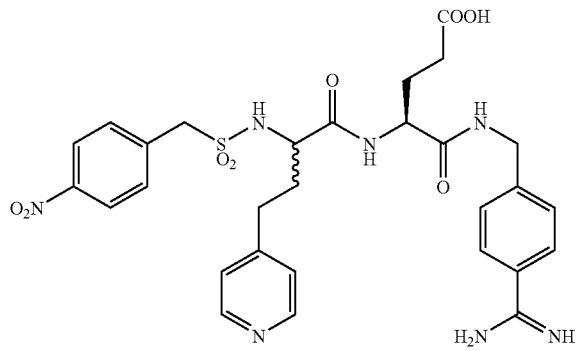 [SMILES: N=C(N)c1ccc(CNC(=O)[C@H](CCC(=O)O)NC(=O)C(CCc2ccncc2)NS(=O)(=O)Cc2ccc([N+](=O)[O-])cc2)cc1] | 0.0056 | 35 | 6250 |

TABLE 1-continued

Determination of the inhibitory constants for factor Ca and thrombin. Also indicated is the selectivity ratio SR (SR = $K_{i\ thrombin}/K_{i\ factor\ Xa}$).

| No. | Structure | $K_i$ (µM) Factor Xa | Thrombin | SR |
|---|---|---|---|---|
| 38 | 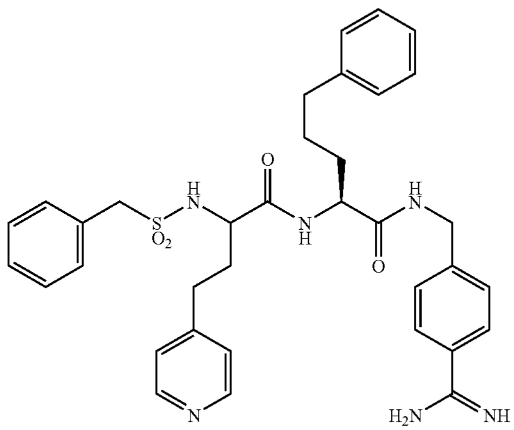 [SMILES: N=C(N)c1ccc(CNC(=O)[C@H](CCCc2ccccc2)NC(=O)C(CCc2ccncc2)NS(=O)(=O)Cc2ccccc2)cc1] | 0.006 | 0.18 | 30 |
| 39 | 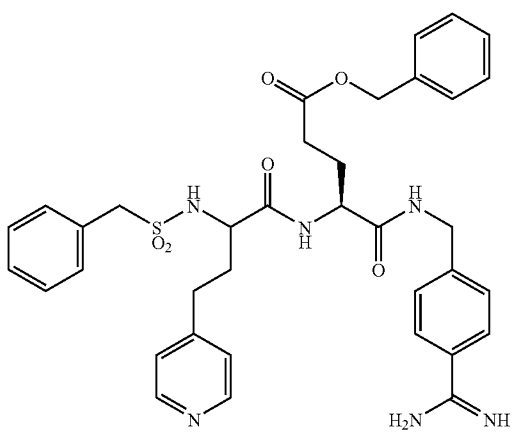 [SMILES: N=C(N)c1ccc(CNC(=O)[C@H](CCC(=O)OCc2ccccc2)NC(=O)C(CCc2ccncc2)NS(=O)(=O)Cc2ccccc2)cc1] | 0.0064 | 0.17 | 26 |
| 40 | 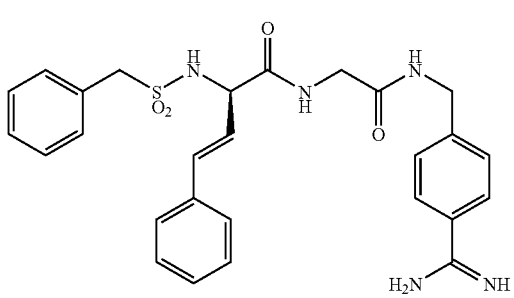 [SMILES: N=C(N)c1ccc(CNC(=O)CNC(=O)[C@@H](/C=C/c2ccccc2)NS(=O)(=O)Cc2ccccc2)cc1] | 0.0065 | 1.1 | 170 |

TABLE 1-continued

*Determination of the inhibitory constants for factor Ca and thrombin. Also indicated is the selectivity ratio SR (SR = $K_{i\ thrombin}/K_{i\ factor\ Xa}$).*

| No. | Structure | $K_i$ (μM) Factor Xa | Thrombin | SR |
|---|---|---|---|---|
| 41 | 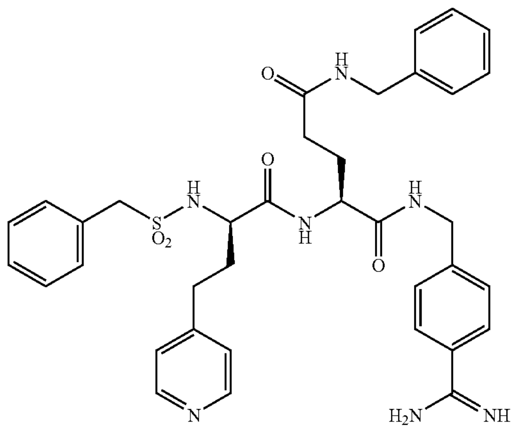 [SMILES: N=C(N)c1ccc(CNC(=O)[C@H](CCC(=O)NCc2ccccc2)NC(=O)[C@@H](CCc2ccncc2)NS(=O)(=O)Cc2ccccc2)cc1] | 0.0068 | 1.7 | 250 |
| 42 | 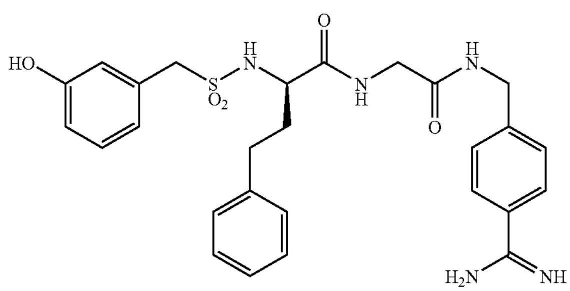 [SMILES: N=C(N)c1ccc(CNC(=O)CNC(=O)[C@@H](CCc2ccccc2)NS(=O)(=O)Cc2cccc(O)c2)cc1] | 0.0072 | 1.5 | 288 |
| 43 | 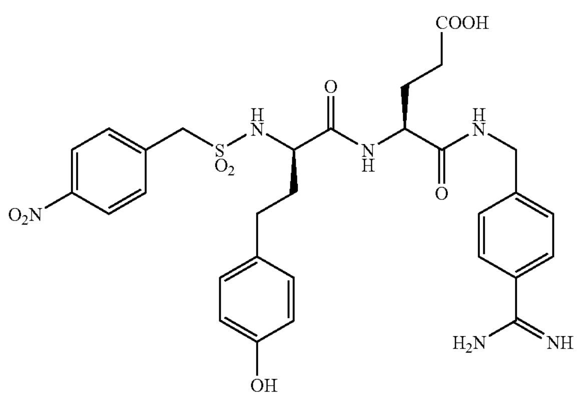 | 0.0075 | 15 | 2000 |
| 44 | 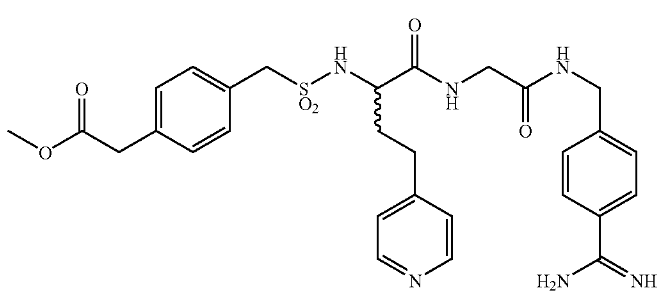 [SMILES: COC(=O)Cc1ccc(CS(=O)(=O)NC(CCc2ccncc2)C(=O)NCC(=O)NCc2ccc(C(=N)N)cc2)cc1] | 0.0082 | 3.8 | 463 |

TABLE 1-continued

Determination of the inhibitory constants for factor Ca and thrombin. Also indicated is the selectivity ratio SR (SR = $K_{i\ thrombin}/K_{i\ factor\ Xa}$).

| No. | Structure | $K_i$ (μM) Factor Xa | Thrombin | SR |
|---|---|---|---|---|
| 45 | 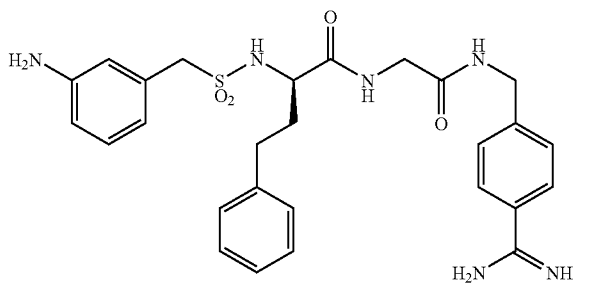 [SMILES: N=C(N)c1ccc(CNC(=O)CNC(=O)[C@@H](CCc2ccccc2)NS(=O)(=O)Cc2cccc(N)c2)cc1] | 0.0093 | 1.4 | 150 |
| 46 | 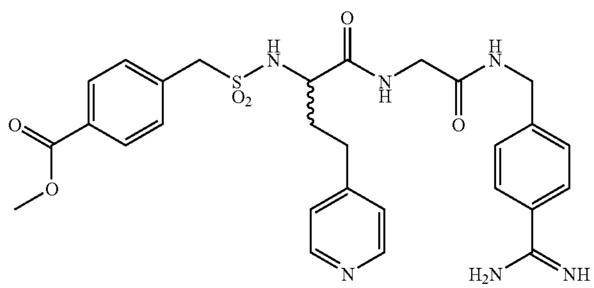 [SMILES: COC(=O)c1ccc(CS(=O)(=O)NC(CCc2ccncc2)C(=O)NCC(=O)NCc2ccc(C(=N)N)cc2)cc1] | 0.0098 | 7.6 | 775 |
| 47 | 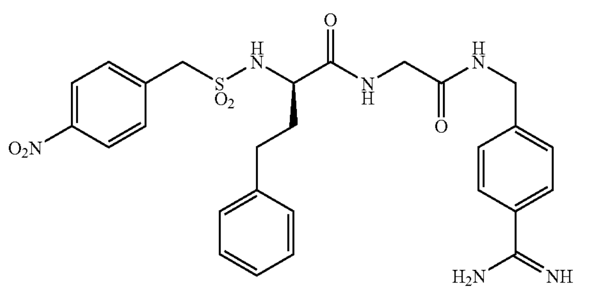 [SMILES: N=C(N)c1ccc(CNC(=O)CNC(=O)[C@@H](CCc2ccccc2)NS(=O)(=O)Cc2ccc([N+](=O)[O-])cc2)cc1] | 0.001 | 0.71 | 71 |
| 48 | 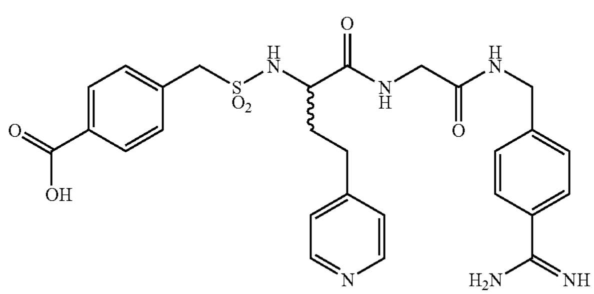 [SMILES: N=C(N)c1ccc(CNC(=O)CNC(=O)C(CCc2ccncc2)NS(=O)(=O)Cc2ccc(C(=O)O)cc2)cc1] | 0.01 | n.b.* | — |
| 49 | 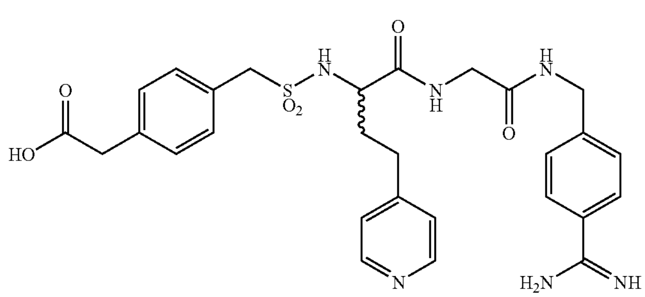 [SMILES: N=C(N)c1ccc(CNC(=O)CNC(=O)C(CCc2ccncc2)NS(=O)(=O)Cc2ccc(CC(=O)O)cc2)cc1] | 0.013 | 38 | 2923 |

TABLE 1-continued

Determination of the inhibitory constants for factor Ca and thrombin. Also indicated is the selectivity ratio SR (SR = $K_{i\ thrombin}/K_{i\ factor\ Xa}$).

| No. | Structure | $K_i$ (μM) Factor Xa | Thrombin | SR |
|---|---|---|---|---|
| 50 | 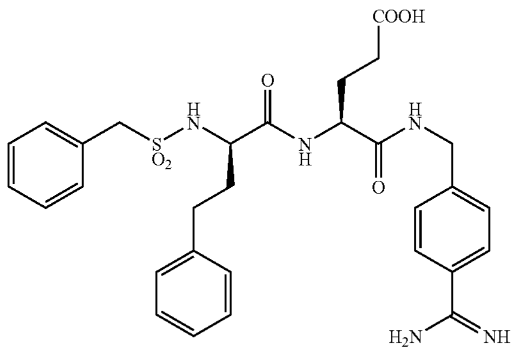 [SMILES: N=C(N)c1ccc(CNC(=O)[C@H](CCC(=O)O)NC(=O)[C@@H](CCc2ccccc2)NS(=O)(=O)Cc2ccccc2)cc1] | 0.013 | 15 | 1153 |
| 51 | 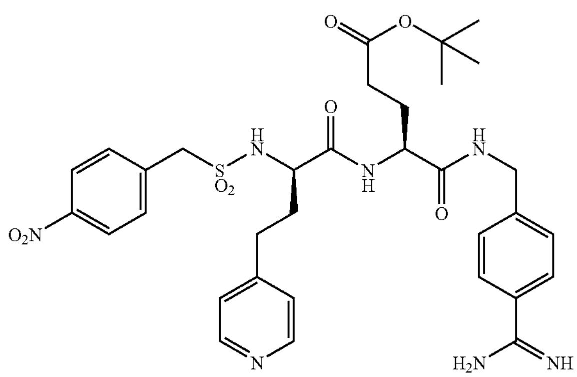 [SMILES: CC(C)(C)OC(=O)CC[C@H](NC(=O)[C@@H](CCc1ccncc1)NS(=O)(=O)Cc1ccc([N+](=O)[O-])cc1)C(=O)NCc1ccc(C(=N)N)cc1] | 0.016 | 1.4 | 87 |
| 52 | 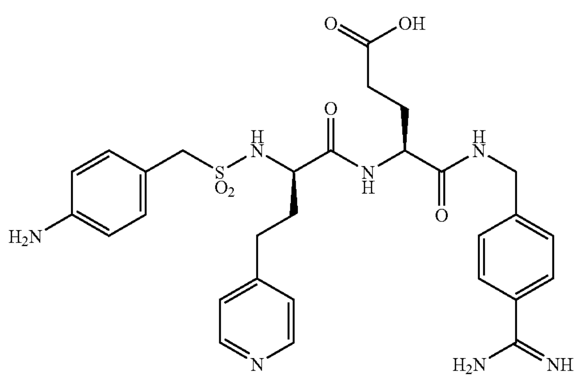 [SMILES: N=C(N)c1ccc(CNC(=O)[C@H](CCC(=O)O)NC(=O)[C@@H](CCc2ccncc2)NS(=O)(=O)Cc2ccc(N)cc2)cc1] | 0.016 | 84 | 5250 |
| 53 | 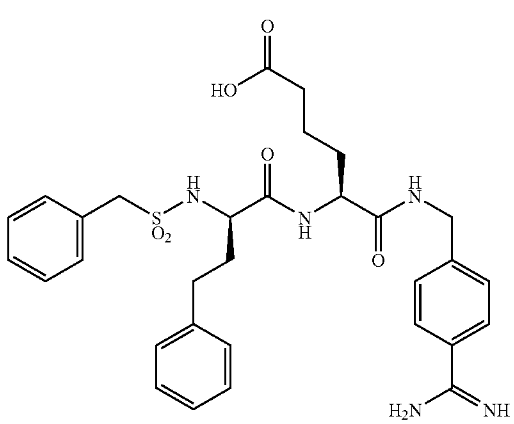 [SMILES: N=C(N)c1ccc(CNC(=O)[C@H](CCCC(=O)O)NC(=O)[C@@H](CCc2ccccc2)NS(=O)(=O)Cc2ccccc2)cc1] | 0.03 | 0.8 | 27 |

TABLE 1-continued

Determination of the inhibitory constants for factor Ca and thrombin. Also indicated is the selectivity ratio SR (SR = $K_{i\ thrombin}/K_{i\ factor\ Xa}$).

| No. | Structure | $K_i$ (μM) Factor Xa | Thrombin | SR |
|---|---|---|---|---|
| 54 | 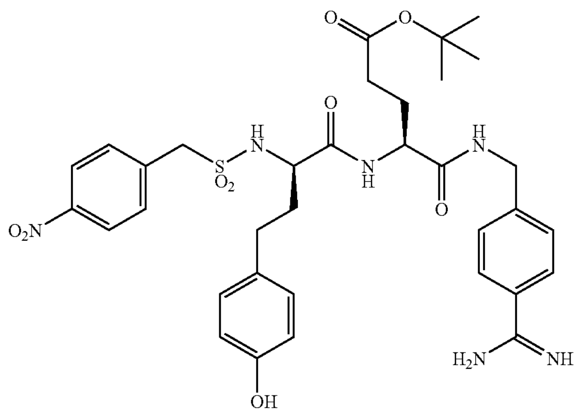 [SMILES: CC(C)(C)OC(=O)CC[C@H](NC(=O)[C@@H](CCc1ccc(O)cc1)NS(=O)(=O)Cc1ccc([N+](=O)[O-])cc1)C(=O)NCc1ccc(C(=N)N)cc1] | 0.039 | 0.69 | 18 |
| 55 | 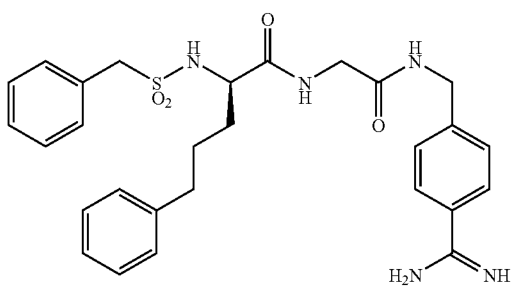 [SMILES: N=C(N)c1ccc(CNC(=O)CNC(=O)[C@@H](CCCc2ccccc2)NS(=O)(=O)Cc2ccccc2)cc1] | 0.067 | 0.21 | 3 |
| 56 | 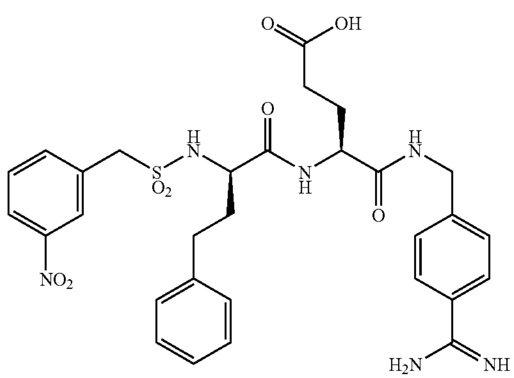 [SMILES: N=C(N)c1ccc(CNC(=O)[C@H](CCC(=O)O)NC(=O)[C@@H](CCc2ccccc2)NS(=O)(=O)Cc2cccc([N+](=O)[O-])c2)cc1] | 0.083 | 13 | 156 |
| 57 | 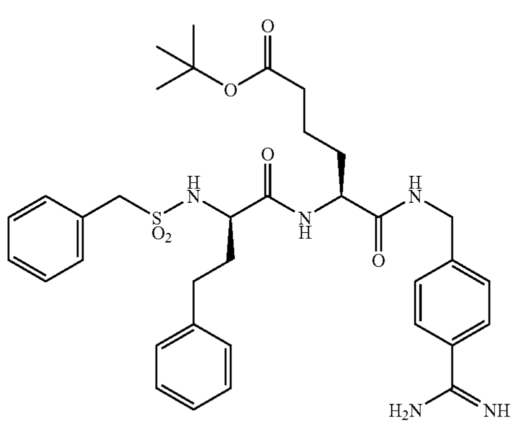 [SMILES: CC(C)(C)OC(=O)CCC[C@H](NC(=O)[C@@H](CCc1ccccc1)NS(=O)(=O)Cc1ccccc1)C(=O)NCc1ccc(C(=N)N)cc1] | 0.13 | 0.46 | 3.5 |

TABLE 1-continued

Determination of the inhibitory constants for factor Ca and thrombin. Also indicated is the selectivity ratio SR (SR = $K_{i\ thrombin}/K_{i\ factor\ Xa}$).

| No. | Structure | $K_i$ (μM) Factor Xa | Thrombin | SR |
|---|---|---|---|---|
| 58 | 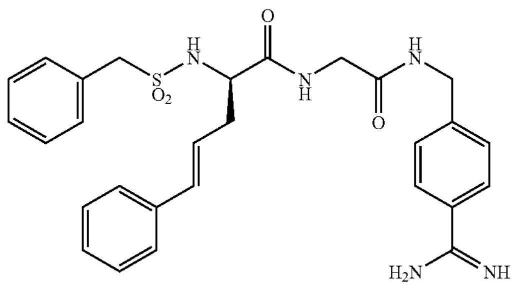 [SMILES: N=C(N)c1ccc(CNC(=O)CNC(=O)[C@@H](C/C=C/c2ccccc2)NS(=O)(=O)Cc2ccccc2)cc1] | 0.58 | 1.8 | 3.1 |
| 59 | 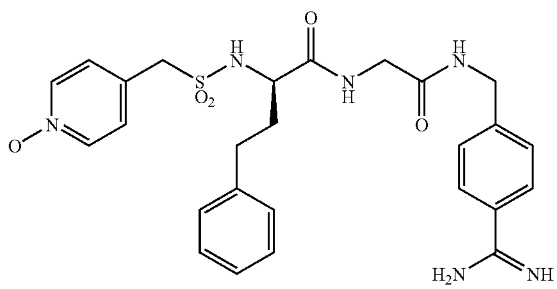 | 0.97 | 16 | 16 |
| 60 | 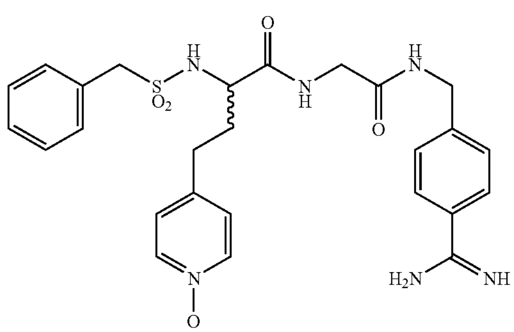 | 0.0048 | 3.5 | 730 |
| 61 | 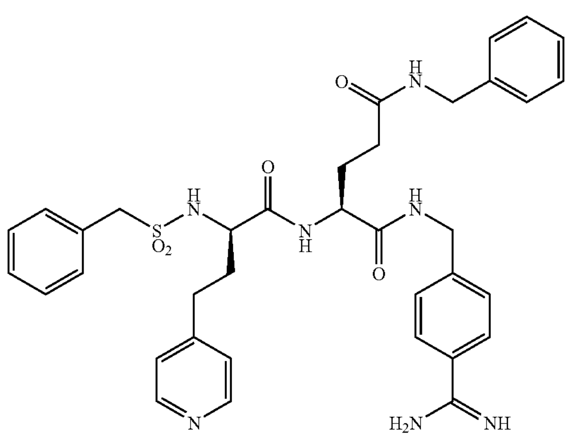 [SMILES: N=C(N)c1ccc(CNC(=O)[C@H](CCC(=O)NCc2ccccc2)NC(=O)[C@@H](CCc2ccncc2)NS(=O)(=O)Cc2ccccc2)cc1] | 0.0068 | 1.7 | 250 |

TABLE 1-continued

Determination of the inhibitory constants for factor Ca and thrombin. Also indicated is the selectivity ratio SR (SR = $K_{i\ thrombin}/K_{i\ factor\ Xa}$).

| No. | Structure | $K_i$ (μM) Factor Xa | Thrombin | SR |
|---|---|---|---|---|
| 62 | 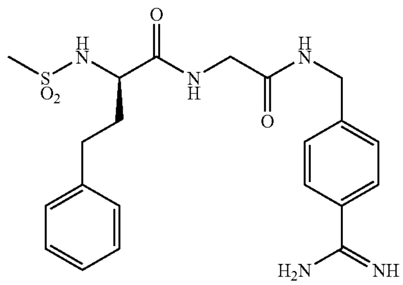 [SMILES: CS(=O)(=O)N[C@H](CCc1ccccc1)C(=O)NCC(=O)NCc1ccc(C(=N)N)cc1] | 1.06 | 1.3 | 1.2 |
| 63 | 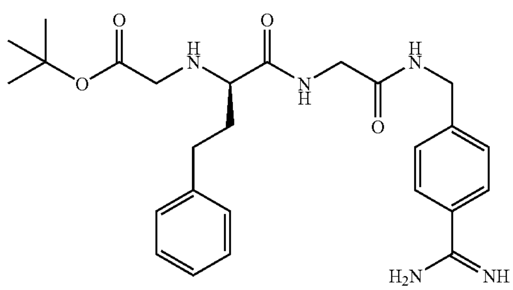 [SMILES: CC(C)(C)OC(=O)CN[C@H](CCc1ccccc1)C(=O)NCC(=O)NCc1ccc(C(=N)N)cc1] | 0.62 | 1.5 | 2.4 |
| 64 | 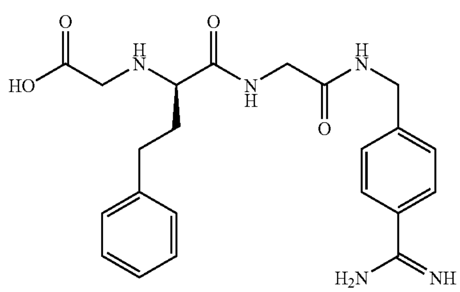 [SMILES: N=C(N)c1ccc(CNC(=O)CNC(=O)[C@@H](CCc2ccccc2)NCC(=O)O)cc1] | 0.87 | 28 | 32 |
| 65 | 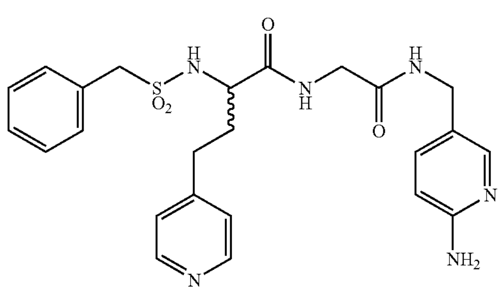 [SMILES: Nc1ccc(CNC(=O)CNC(=O)C(CCc2ccncc2)NS(=O)(=O)Cc2ccccc2)cn1] | 0.12 | 100 | 833 |

*n.b. = not determined

Determination of the inhibitory Effect

To determine the inhibitory effect, 200 μl of this buffer (0.05 M 0.154 M NaCl, 5% Ethanol, pH 8.0; contains the inhibitor), 25 μl of substrate (Moc-D-Nle-Gly-Arg-pNA in H₂O; Pentapharm Ltd., Basle, Switzerland) and 50 μl of factor Xa (bovine, Diagnostic Reagents Ltd, thame, GB) were incubated at 25° C. After 3 min, the reaction was stopped By adding 25 μl of acetic acid (50%), and the absorption at 405 nm was determined using a Microplate Reader (MR 5000, Dynatech, Denkendorf, Germany). The $K_i$ values were Founder by the Dixon method (boichem. J. 55, 170-171, 1953) by linear regression using a Computer program. The $K_i$ values are the average of at least three determinations. The Thrombin inhibitions was determined in analogy to a method described earlier (Stürzebecher et al., J. Med. Chem. 40, 3091-3099, 1997).

The invention claimed is:

1. A compound of the general formula I

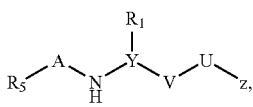

where
A is $P_2$-$P_1$ with

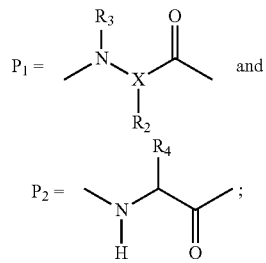

$R_1$ is H;
$R_2$ is —$CH_2$—$OR_7$ or —$CH_2$—$OCOOR_7$, where $R_7$ is H or a branched or unbranched alkyl radical having 1-5 C atoms, or $R_2$ is a —$CH_2$—$CH_2$—$COOR_{7*}$ or —$CH_2$—$CH_2$—$CH_2$—$COOR_{7*}$, where $R_{7*}$ is H or a branched or unbranched alkyl radical having 1-5 C atoms;
$R_3$ is H;
$R_4$ is —$(CH_2)_f$—$R_8$ with f=0 or 2 or —CH=CH—$R_8$, where $R_8$ is a mono- or polysubstituted or unsubstituted phenyl ring that is attached to —$(CH_2)_f$— or —CH=CH— at a carbon of said phenyl ring or a mono- or polysubstituted or unsubstituted pyridyl radical that is attached to —$(CH_2)_f$— or —CH=CH— at a carbon of the pyridyl ring, and where $P_2$ in the structure A of the general formula I is in the D or L configuration;
$R_5$ is —$SO_2R_{9*}$ or —$SO_2$—NH—$R_{9*}$, where $R_{9*}$ is a mono- or polysubstituted or unsubstituted aralkyl or heteroaralkyl radical, where the optional substituent is selected from —OH, —O—$COOR_7$, —$CH_2$—$OCOOR_7$, with $R_7$ as defined above, —$NH_2$, —$NO_2$, —$COOR_{10}$, —$CH_2$—$COOR_{10}$ group or a Cl, F or Br atom, and where $R_{10}$ is an H or an alkyl radical having 1 to 6 C atoms;
U is a phenyl or pyridyl radical;
V is $(CH_2)_n$ with n=0 or 1;
X is CH;
Y is CH; and z occurs in position 2, 3 or 4, and is an aminomethyl, a guanidino group or an amidino group

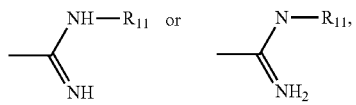

where $R_{11}$ is H, OH, $NH_2$, —$COR_{12}$ or —$COOR_{12}$, where $R_{12}$ is a branched or unbranched alkyl radical having 1 to 8 C atoms or a mono- or polysubstituted or unsubstituted aryl or heteroaryl, aralkyl or heteroaralkyl radical, where the alkyl radical has 1 to 16 C atoms and the aryl or heteroaryl radical has 4 to 14 C atoms;
or a compound of the general formula I in the form of its salt.

2. The compound as claimed in claim 1, characterized in that the structural element

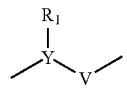

of the formula I is a —$CH_2$— or —NH— group.

3. The compound as claimed in claim 1, characterized in that $R_2$ is —$CH_2$—$CH_2$—COOH, —$CH_2$—$CH_2$—COOCH$_2$CH$_3$ or —$CH_2$OH;
$R_4$ is —$(CH_2)_2$—$R_8$;
$R_5$ is a benzylsulfonyl, aminobenzylsulfonyl, hydroxybenzylsulfonyl, chlorobenzylsulfonyl, fluorobenzylsulfonyl, carboxybenzylsulfonyl, ethyloxycarbonylbenzylsulfonyl, carboxymethylbenzyl-sulfonyl, ethyloxycarbonylmethylbenzylsulfonyl, pyridylmethylsulfonyl, or N-(oxide)-pyridylmethylsulfonyl radical;
U is a phenyl radical;
V is $(CH_2)_n$ with n=0; and
z is present in position 4 and is an amidino group

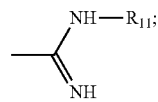

where $R_{11}$ is H, OH or —$COOR_{12}$ with $R_{12}$ a branched or unbranched alkyl radical having 2, 4, or 6 C atoms.

4. The compound as claimed in claim 1, characterized in that $R_4$ is a —$CH_2$—$CH_2$—$R_8$ radical, where $R_8$ is optionally substituted by one or more —$NH_2$ and/or —OH groups.

5. The compound as claimed in claim 1, characterized in that the substituent is —OH, —NH₂, —NO₂, —COOH, —COOCH₂CH₃, or a halogen.
6. A compound selected from the following structures:
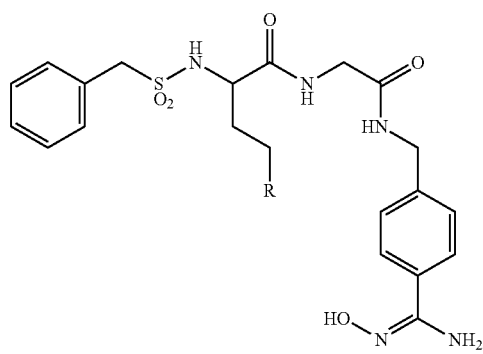
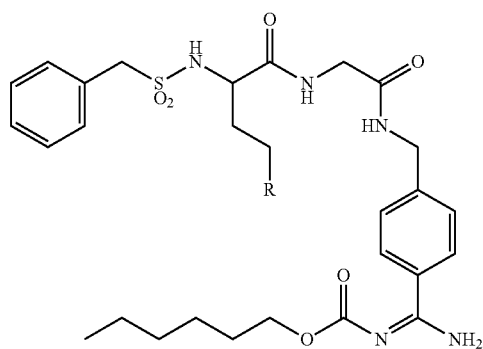
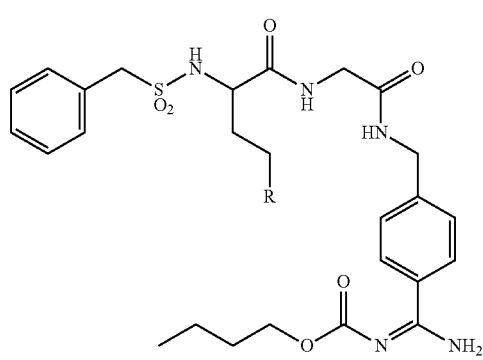
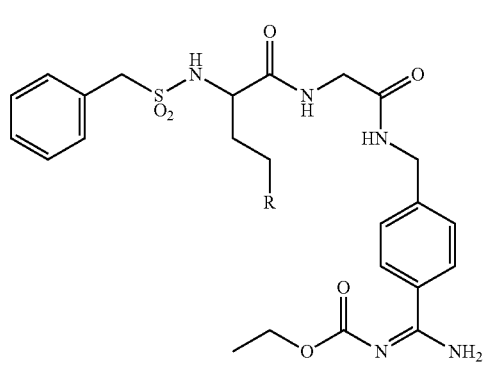
-continued
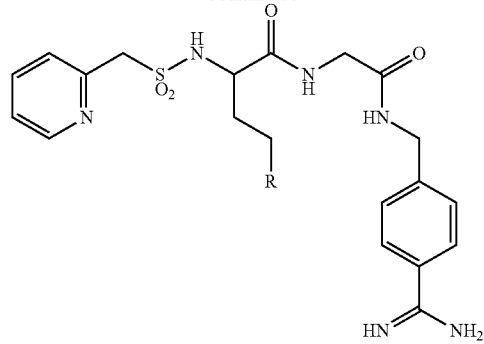
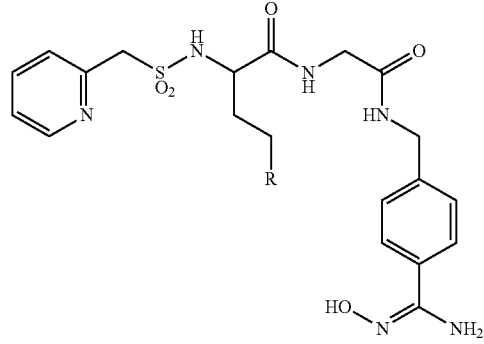
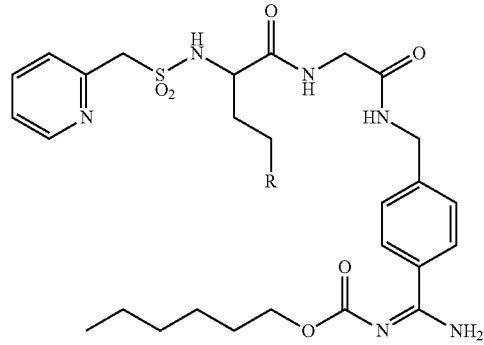
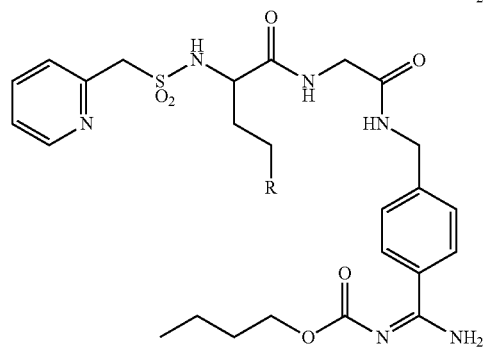
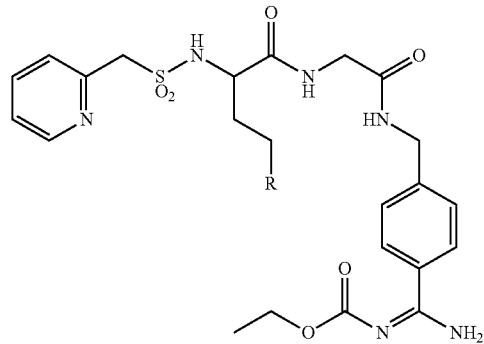

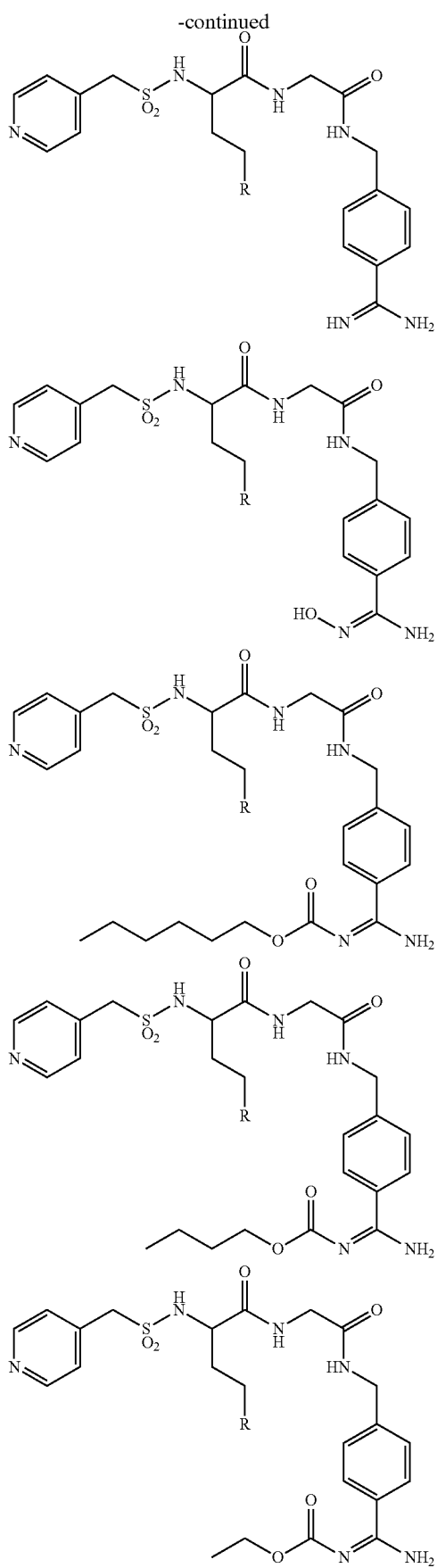
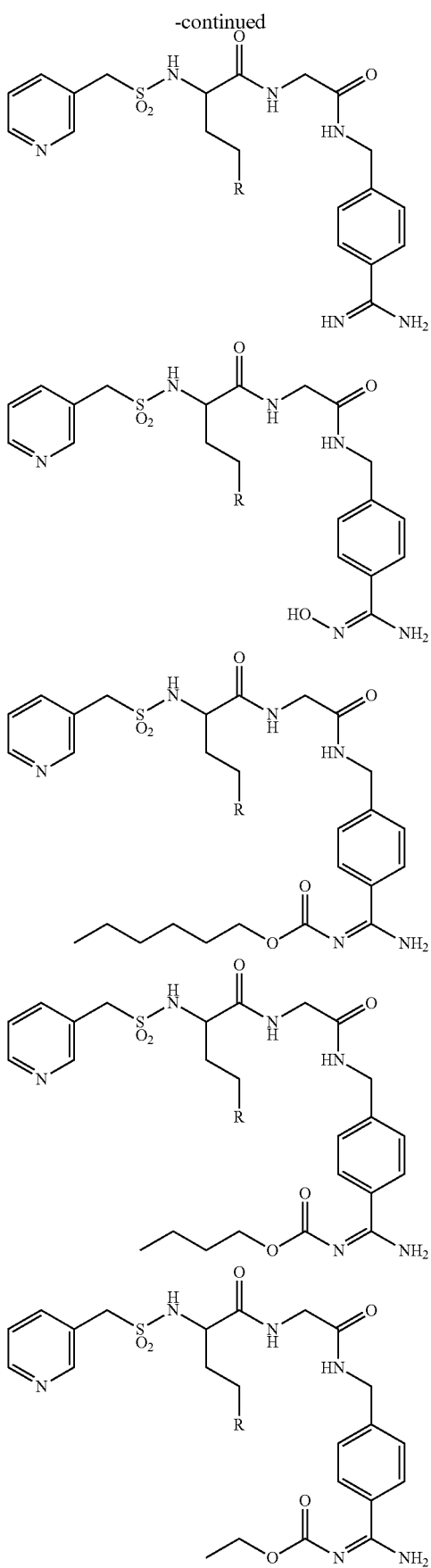

59
-continued
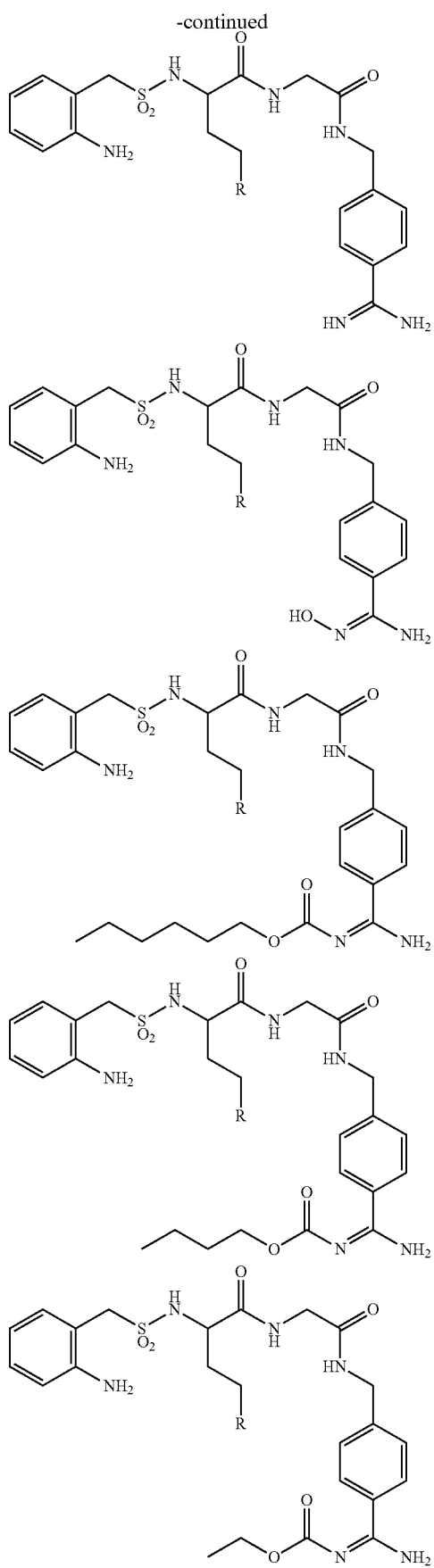
60
-continued
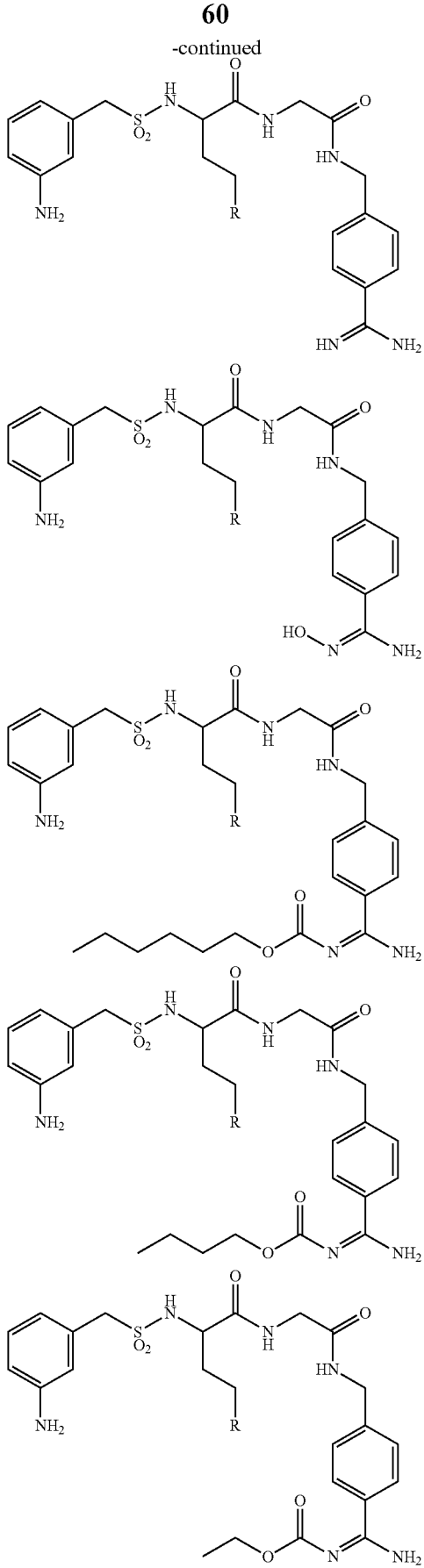

-continued
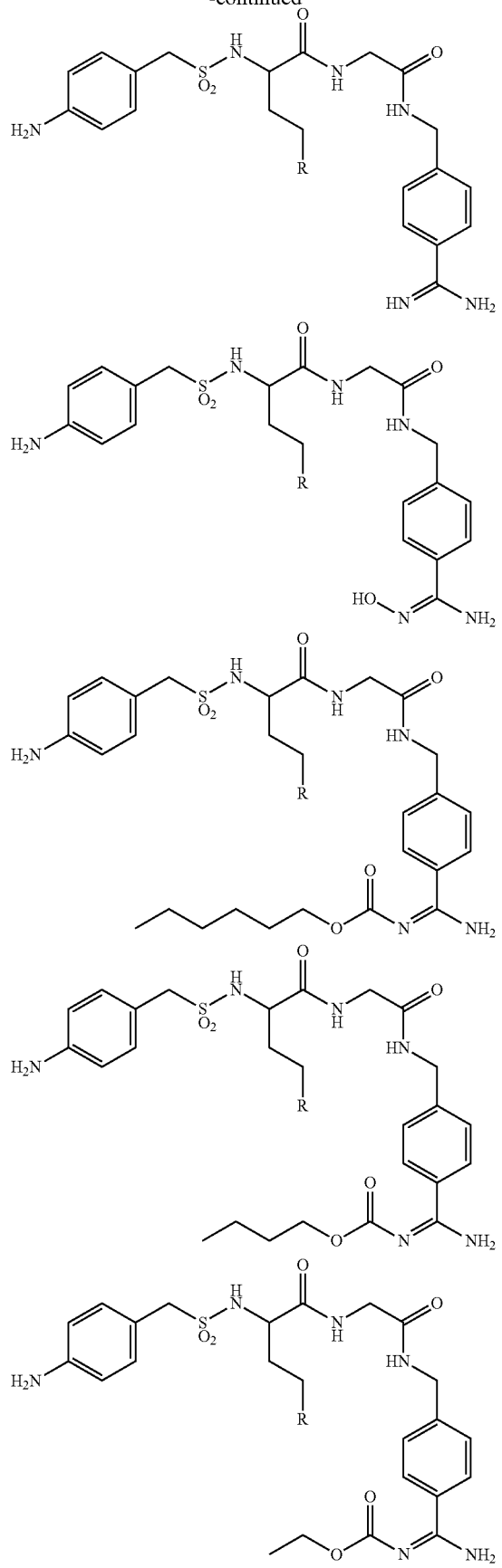
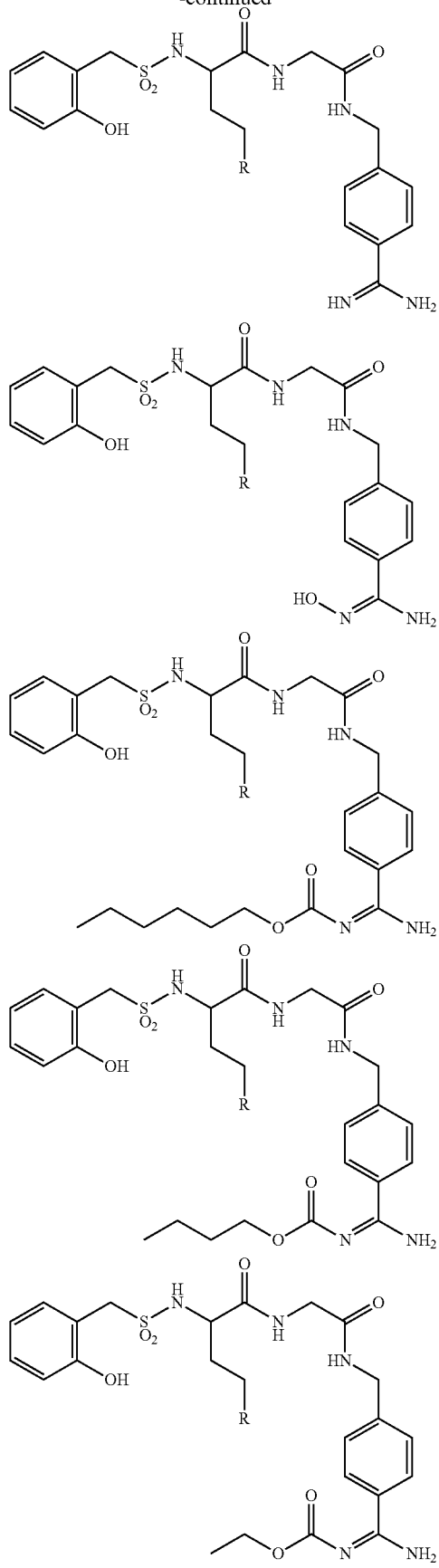

63
-continued
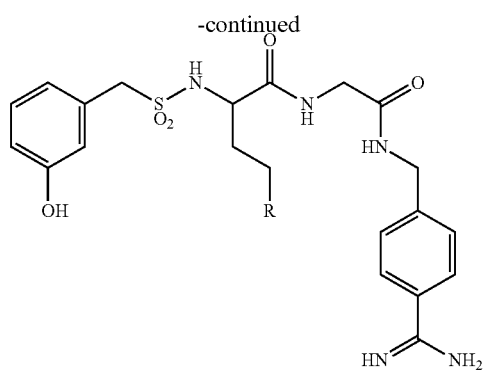
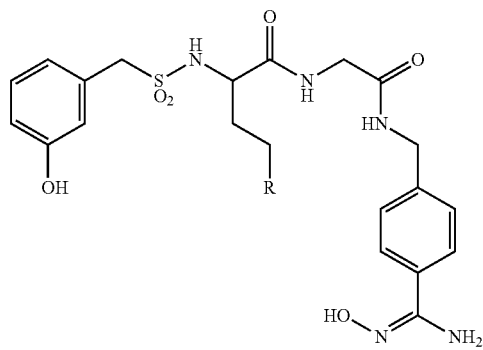
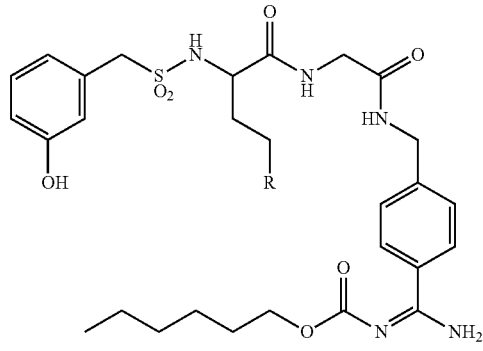
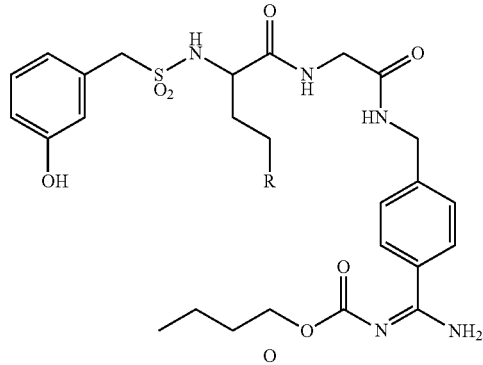
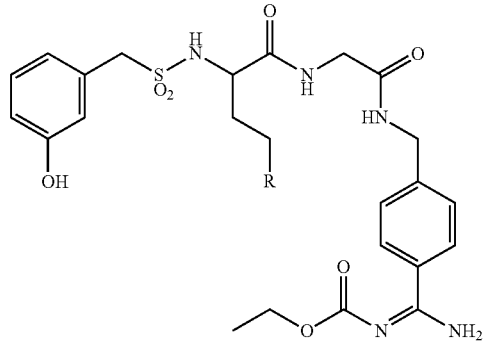
64
-continued
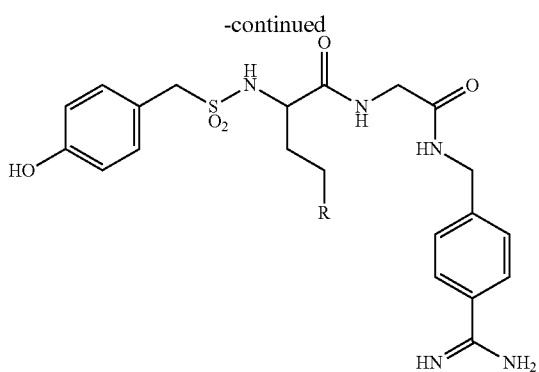
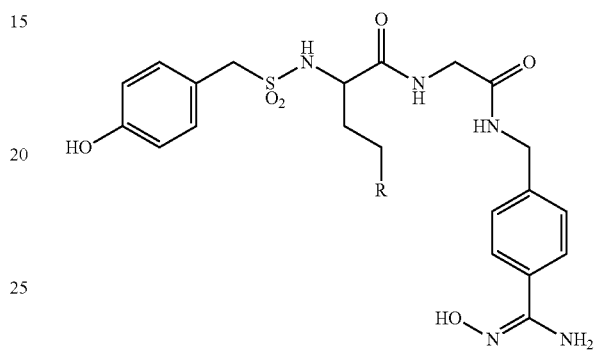
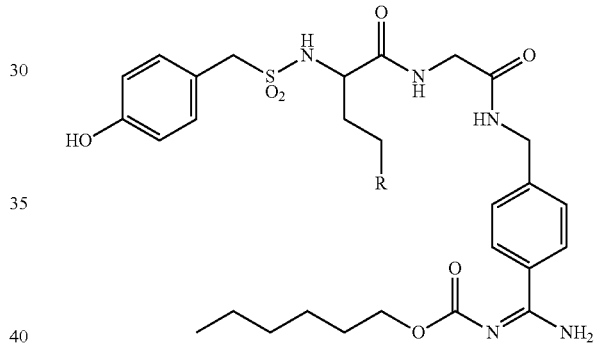
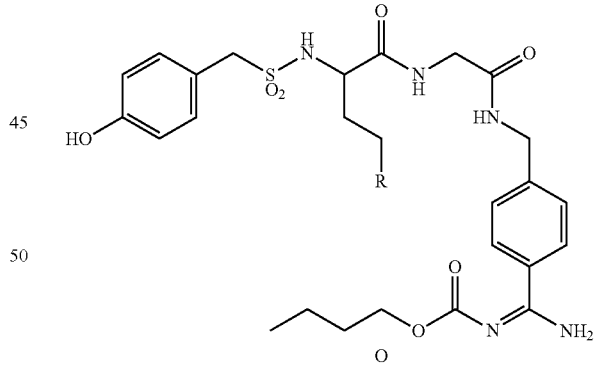
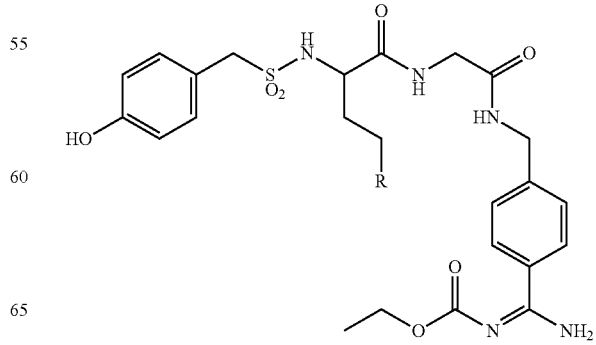

65
-continued
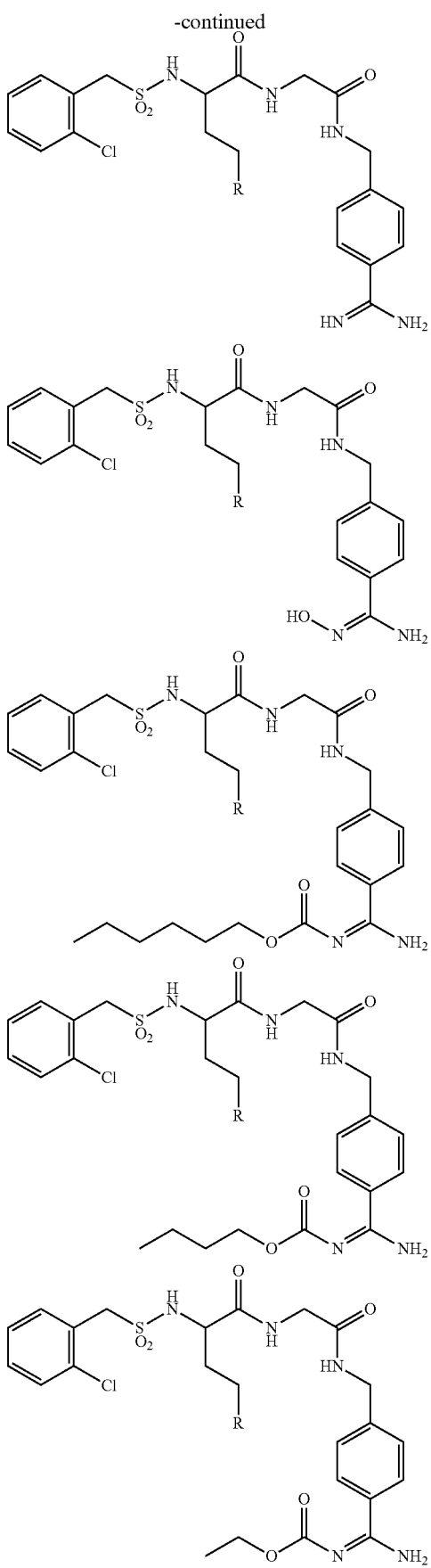
66
-continued
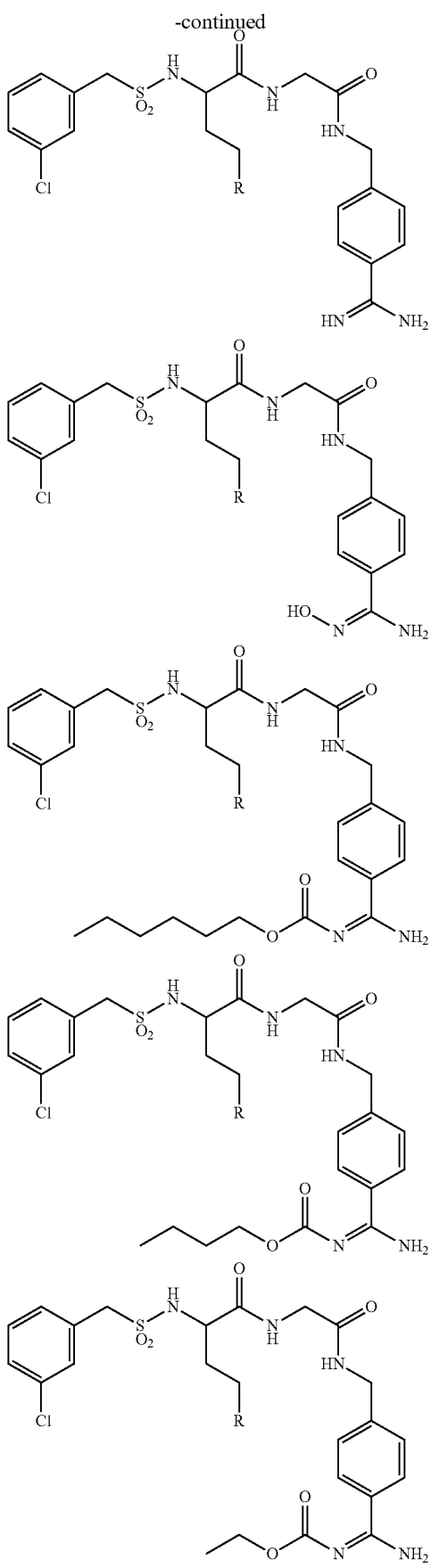

-continued
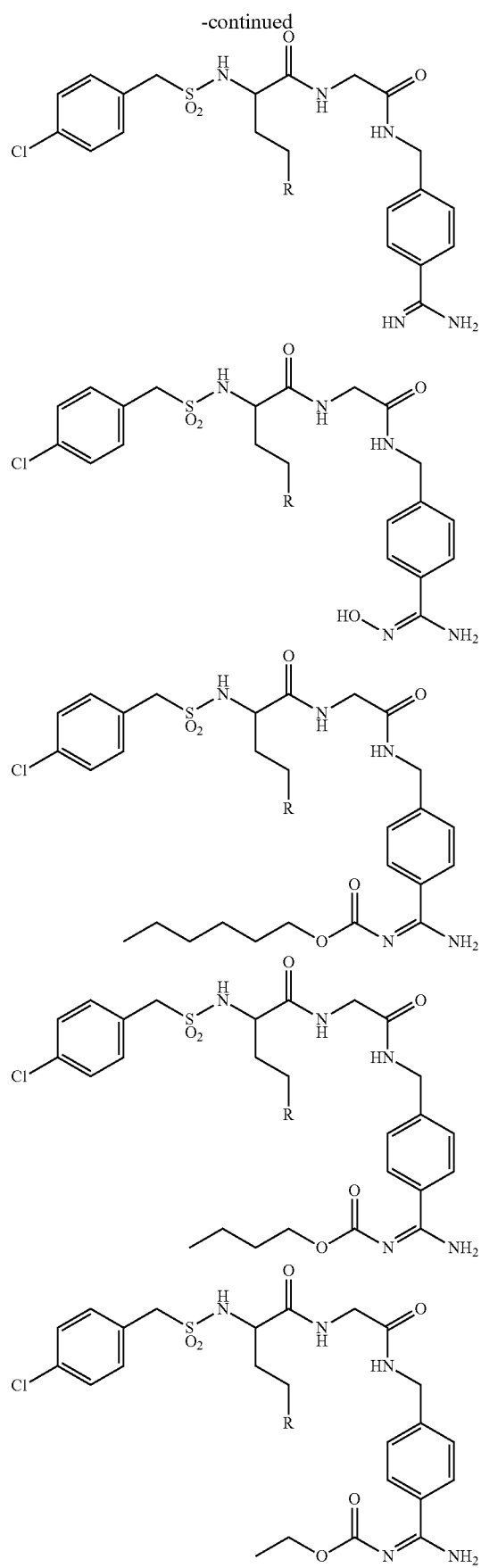
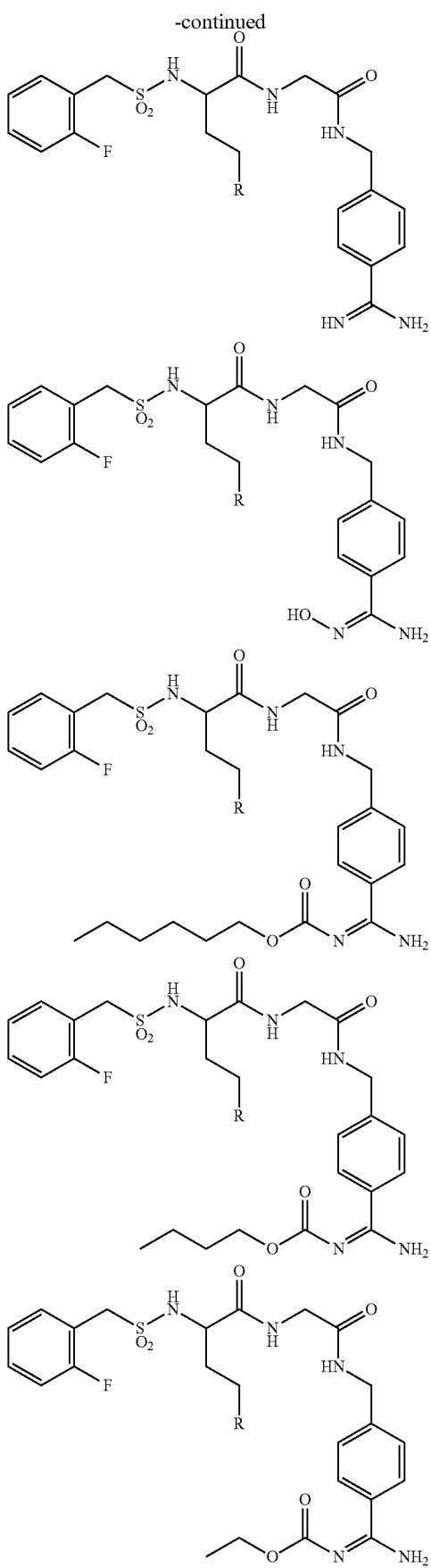

-continued
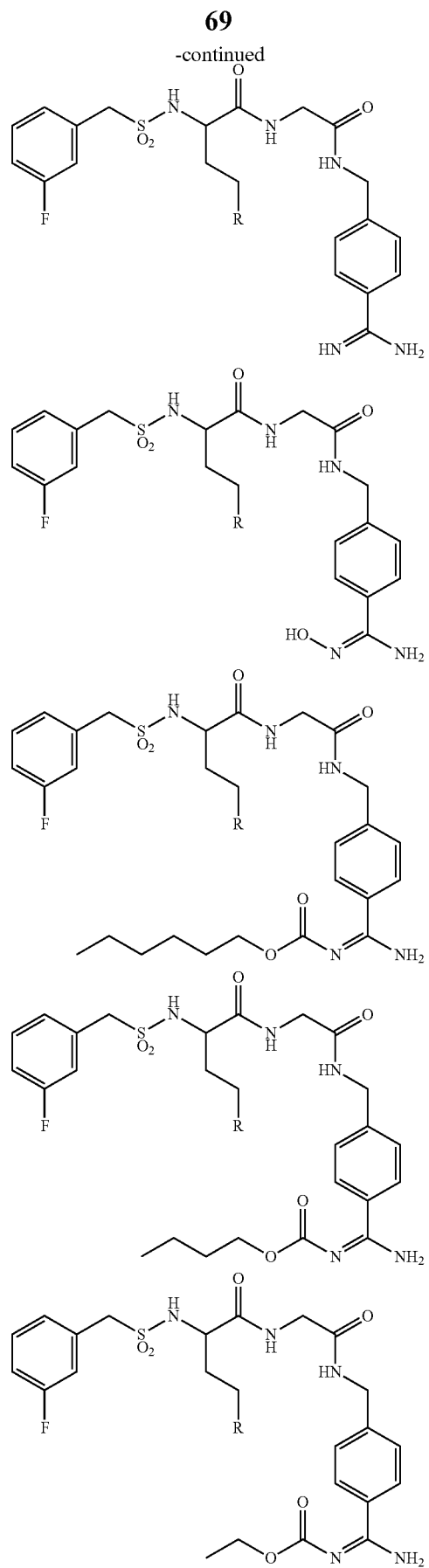
69
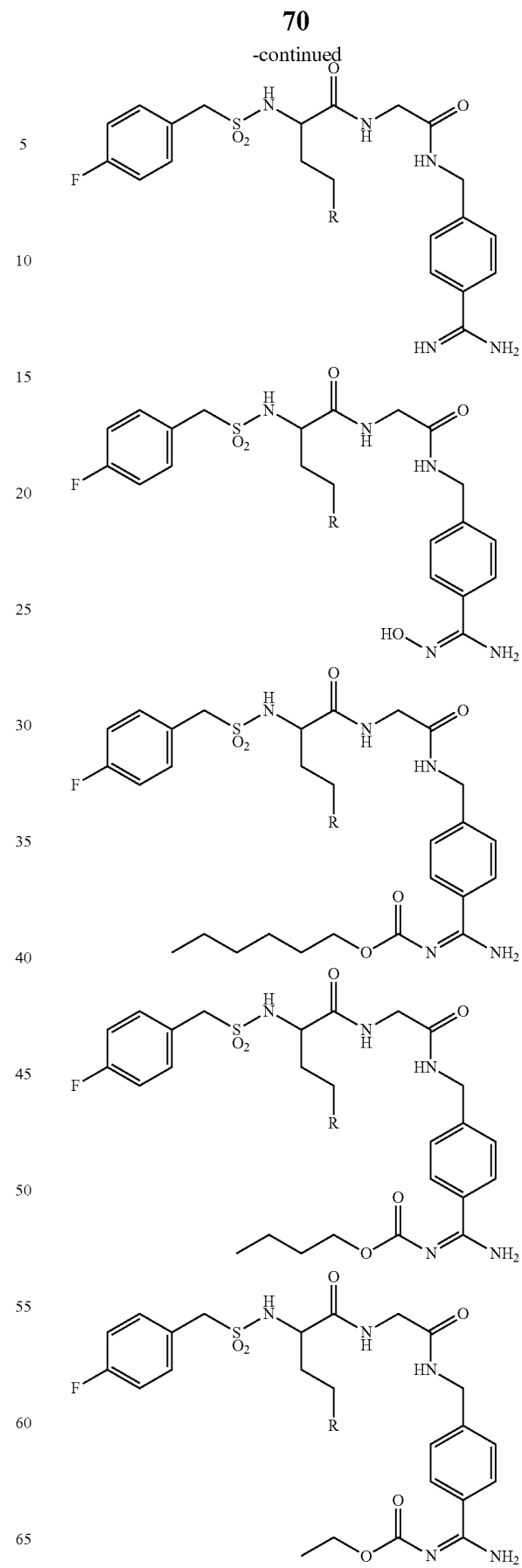
70

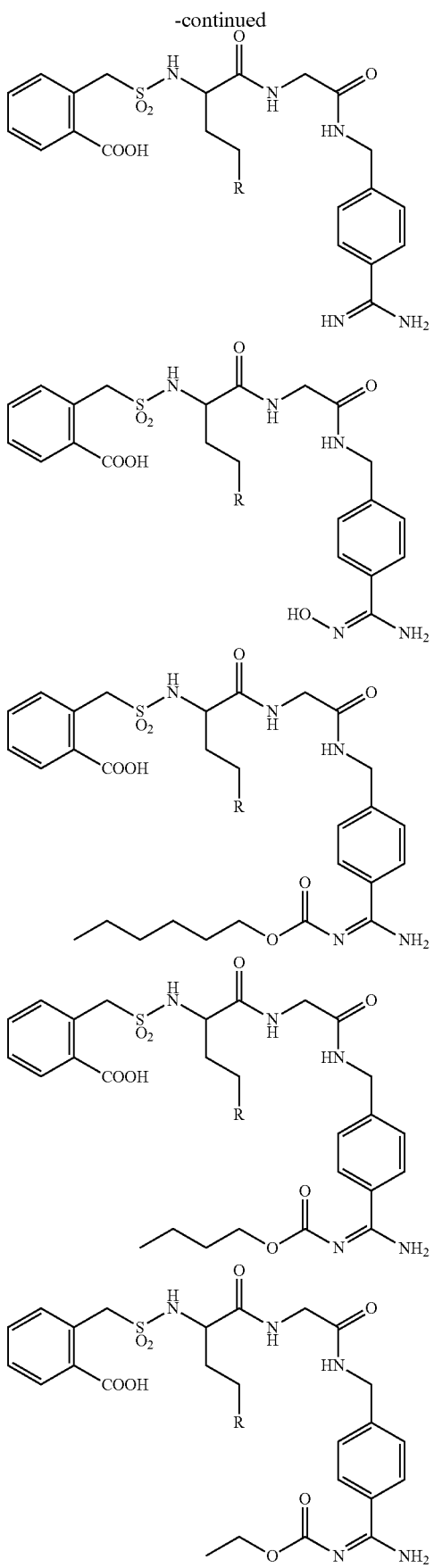

73
-continued
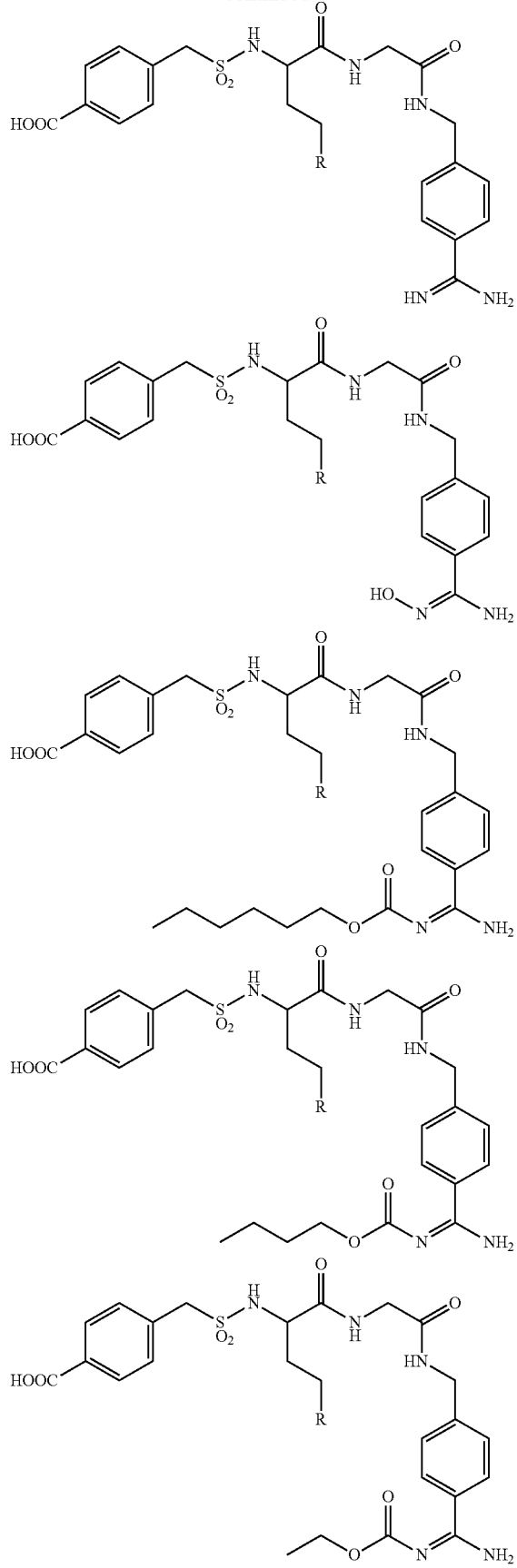
74
-continued
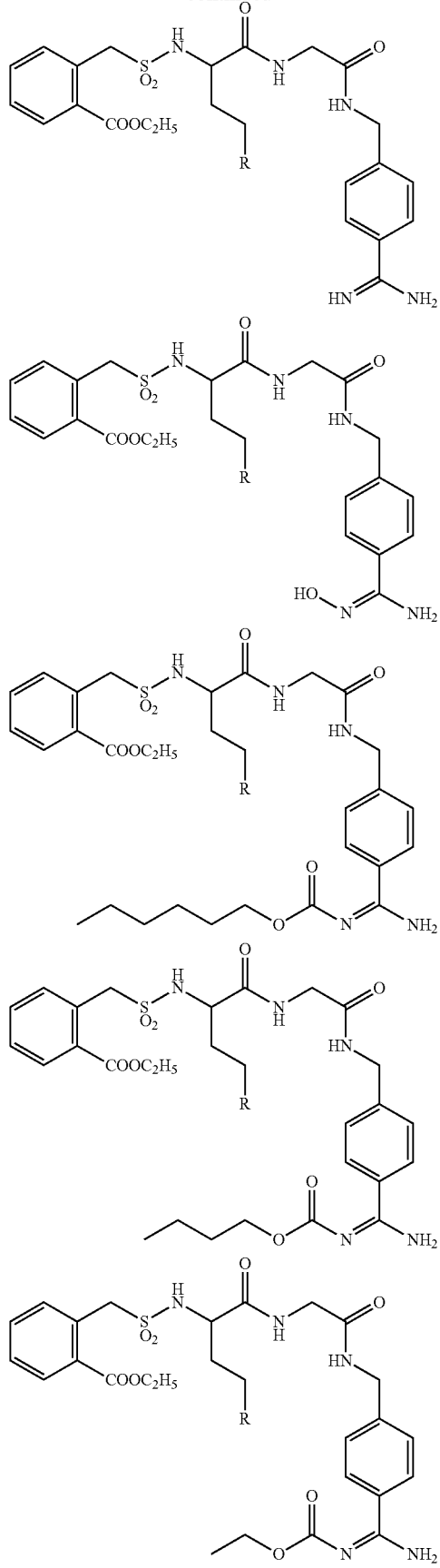

75
-continued
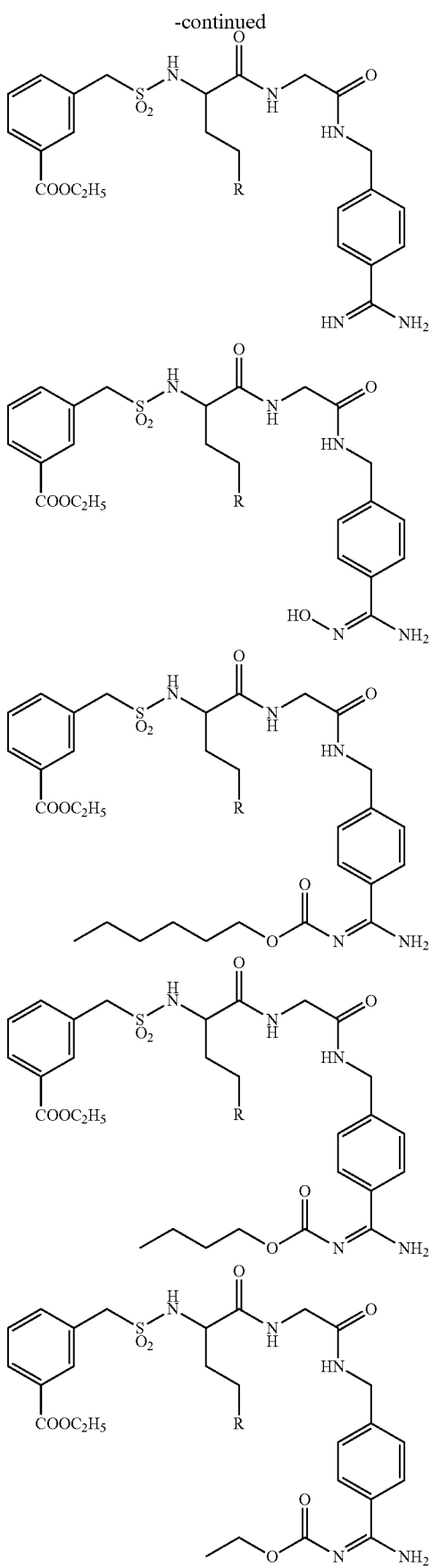
76
-continued
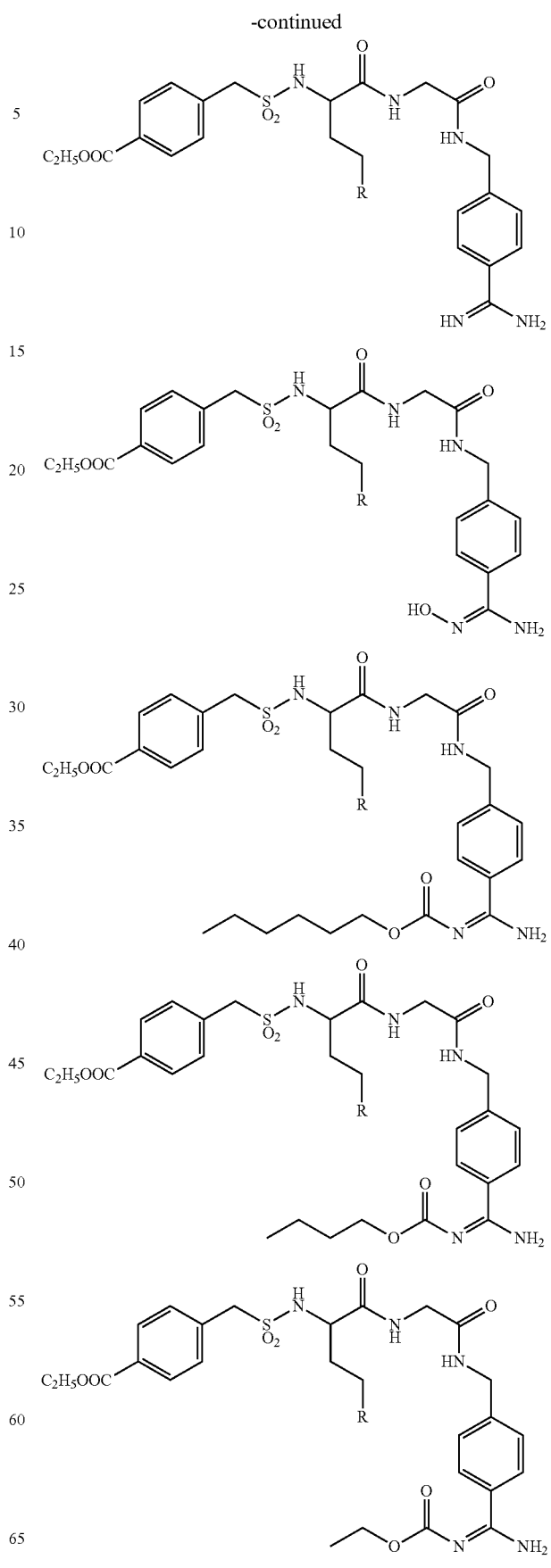

77
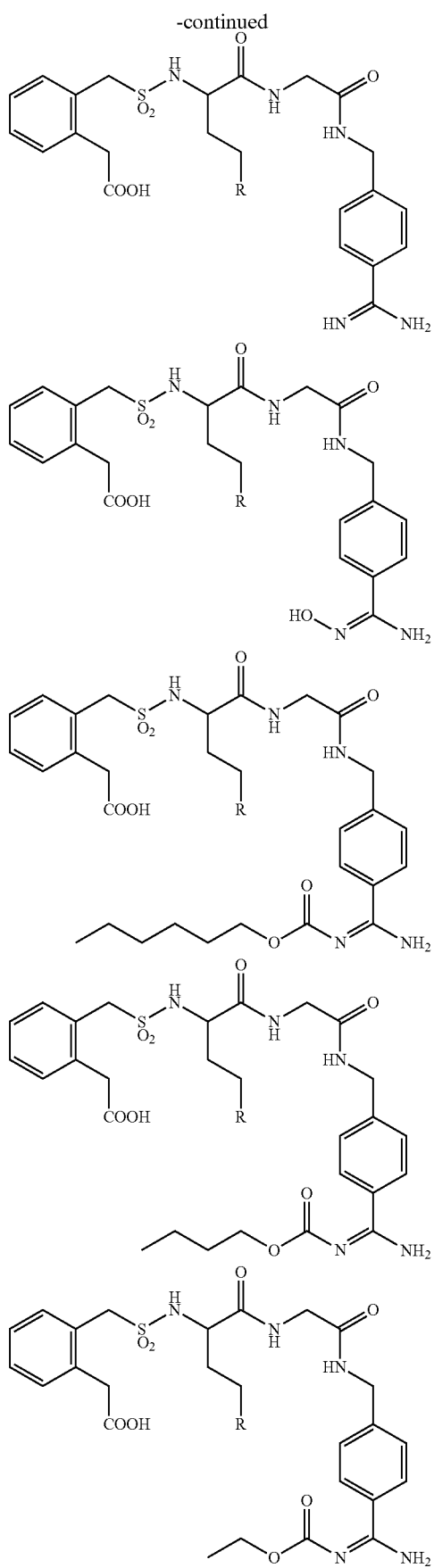
78
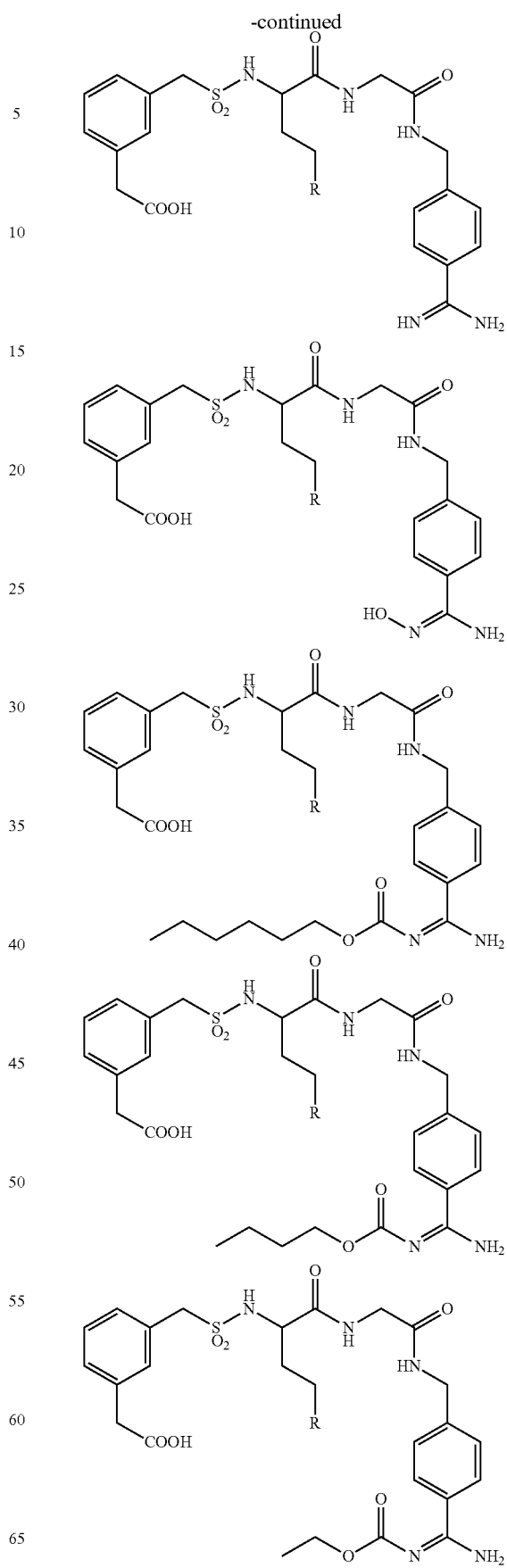

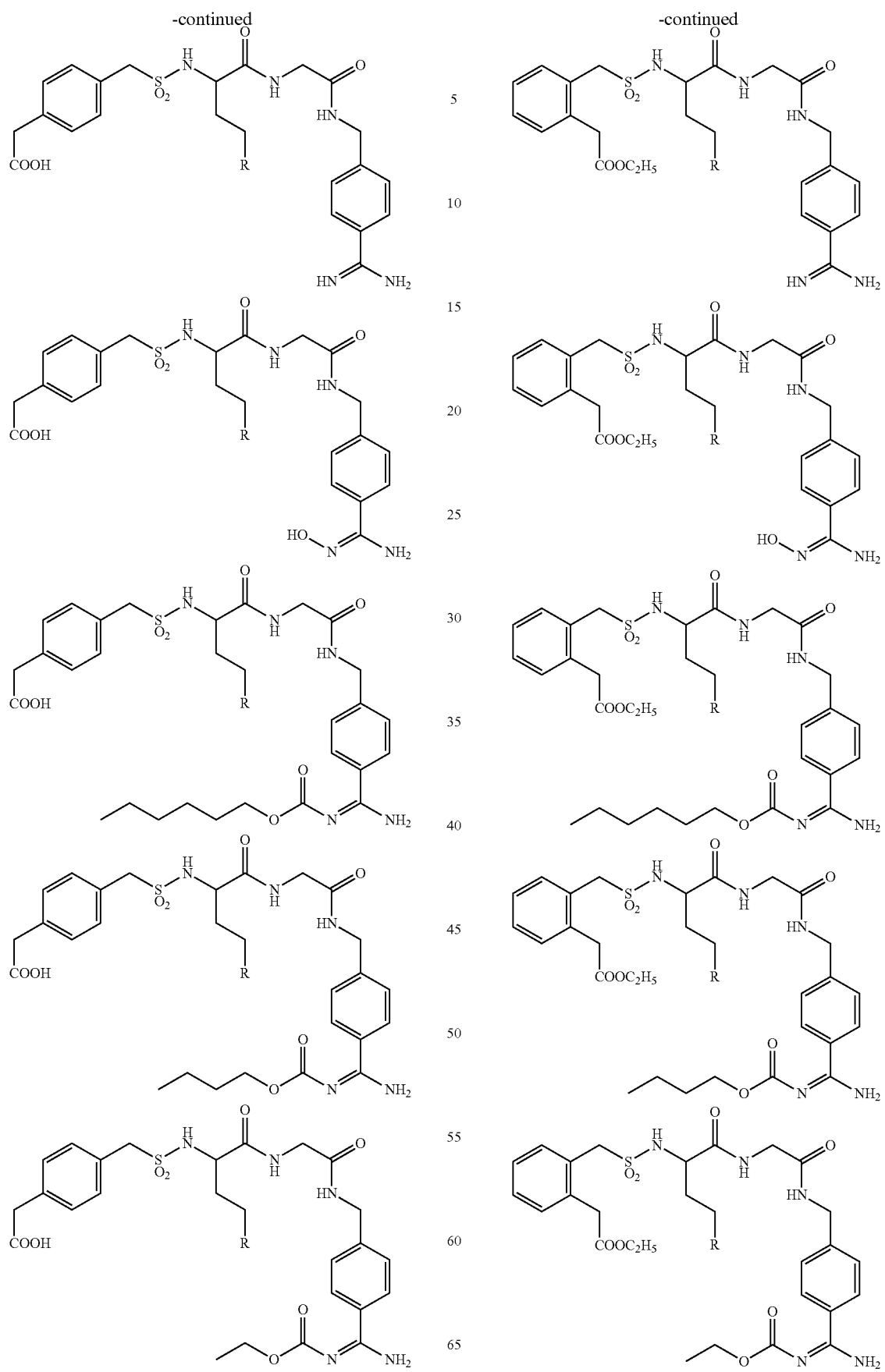

81  82
-continued  -continued
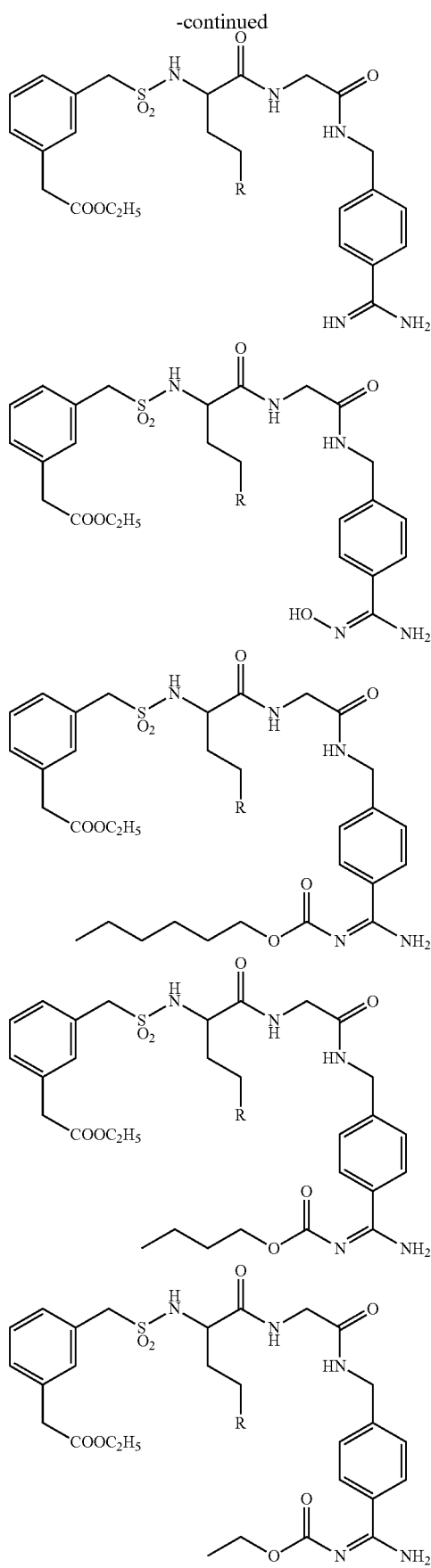
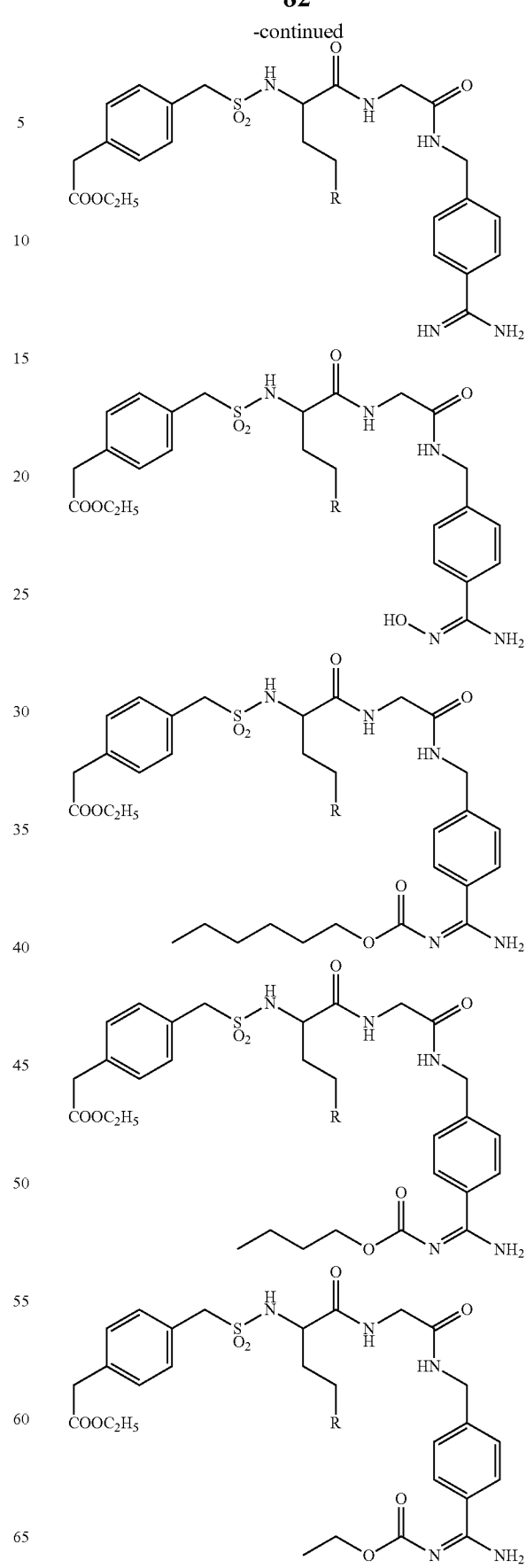

83
-continued
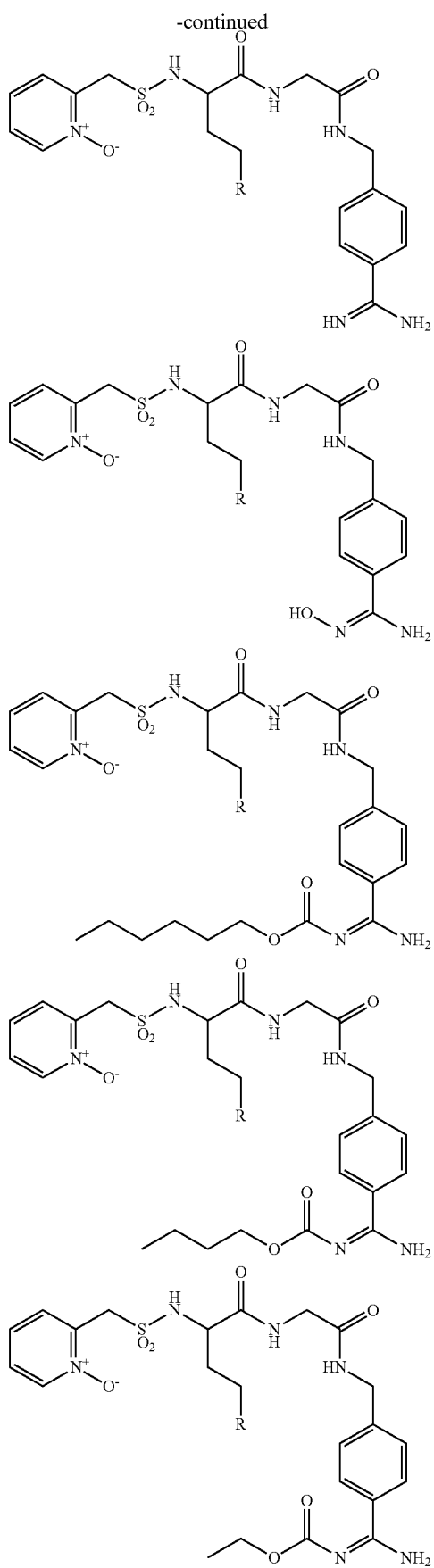
84
-continued
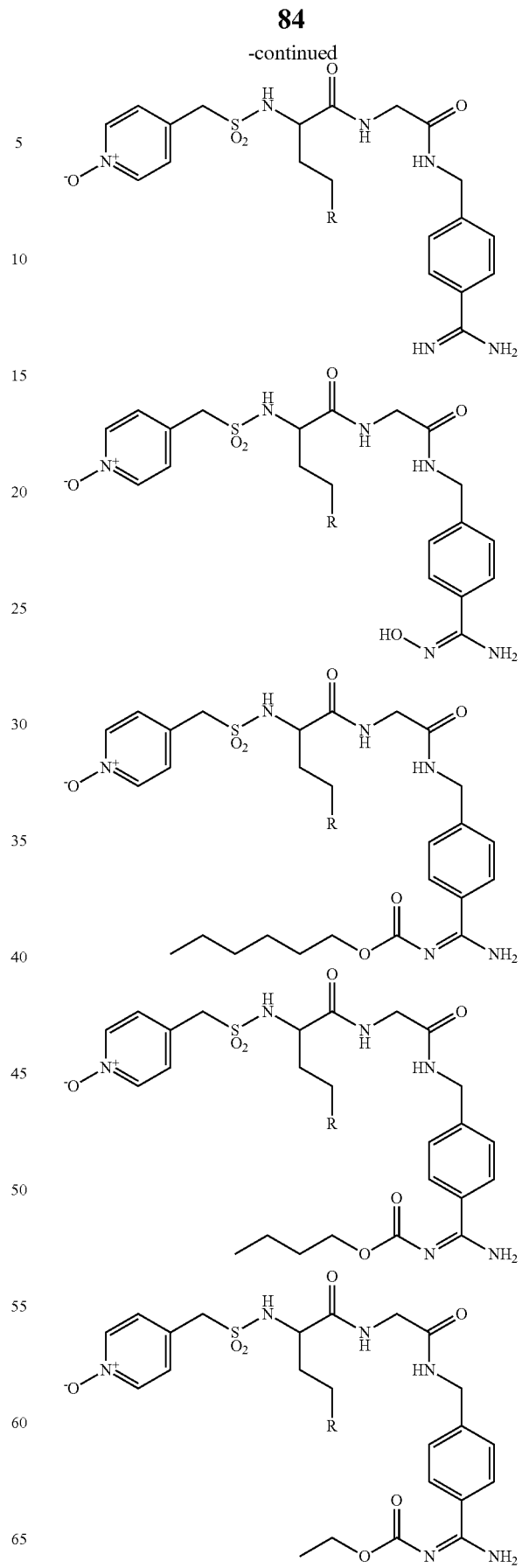

85
-continued
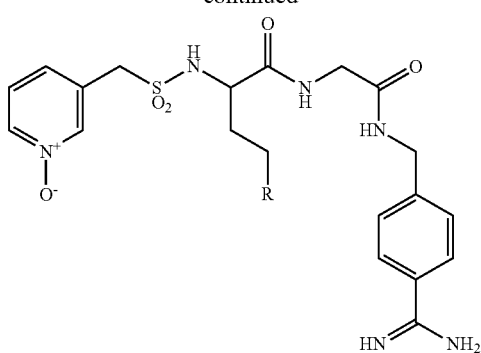
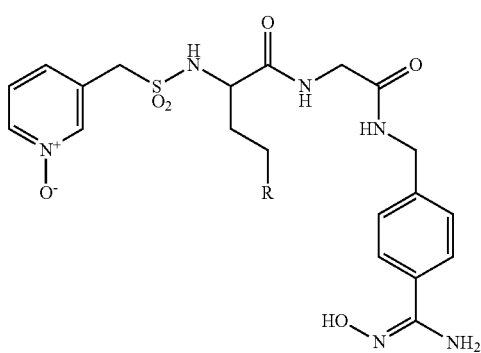
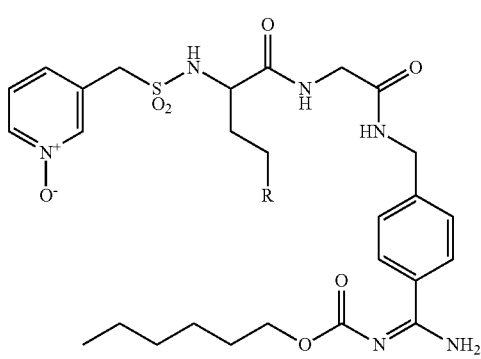
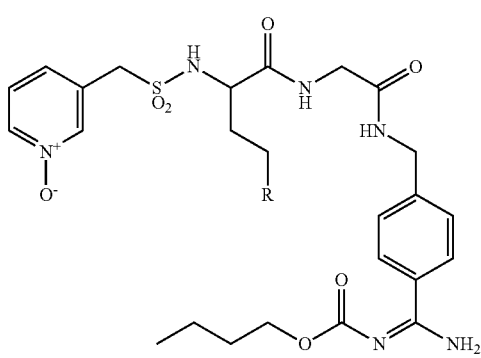
86
-continued
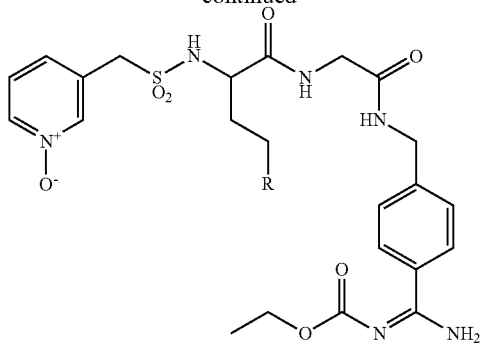
where the radical R is selected from the radicals
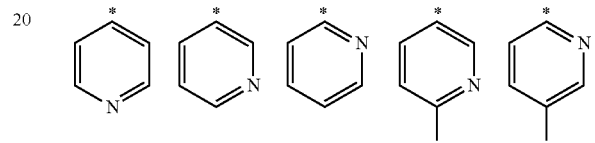
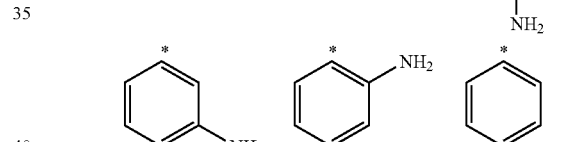
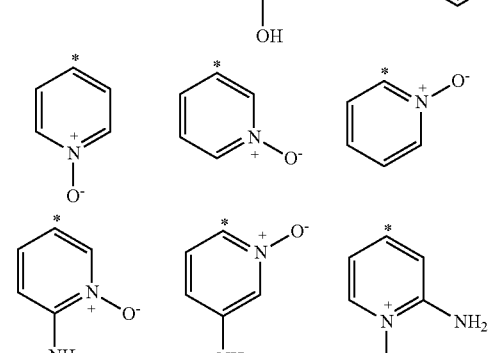

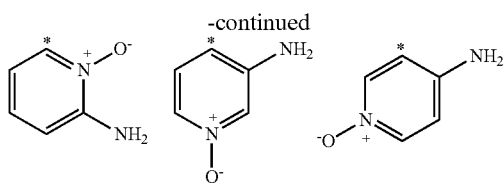

where the linkage of the group R to the Cγ carbon atom of the radical $P_2$ originates from the atom labeled with an asterisk, and the amino acid on which the radical R is located is optionally in the D or the L configuration.

7. The compound as claimed in claim 1, characterized in that the compound is selected from a structure as claimed in claim 9, where, in the structures mentioned, the glycine residue with the structural element

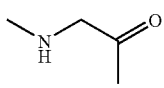

is in each case replaced by a serine residue with the structural element

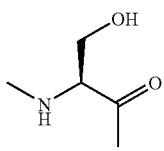

or by a glutamic acid residue with the structural element

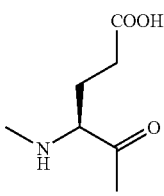

or by a glutamine γ-ethyl ester with the structural element

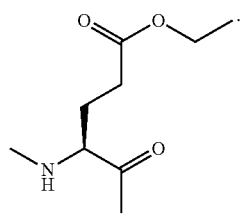

8. The compound as claimed in claim 1, characterized in that the compounds are in the form of salts.

9. A medicament comprising a compound as claimed in claim 1 and pharmaceutically suitable excipients and/or additives.

10. The medicament as claimed in claim 9, where the medicament is employed in the form of a tablet, of a coated tablet, of a capsule, of a pellet, suppository, of a solution, of eyedrops, nose and ear drops, of a syrup, of an emulsion or suspension, of a pessary, stick, aerosol, dusting powder, of a paste, cream or ointment.

11. The compound of claim 1, wherein $R_7$ is an H or a branched or unbranched alkyl radical having 1-3 C atoms; or $R_{7*}$ is ethyl; or f is 2; or $P_2$ is in the D configuration; or $R_{9*}$ is benzyl; or $R_{10}$ is an alkyl radical having 1 to 4 C atoms; or V is $(CH_2)_n$, and n=0; or z occurs in position 4; or $R_{12}$ is a branched or unbranched alkyl radical having 1 to 6 C atoms, or $R_{12}$ is a mono- or polysubstituted or unsubstituted aryl or heteroaryl, aralkyl or heteroaralkyl radical, where the alkyl radical has 1 to 8 C atoms, or the aryl or heteroaryl has 6 to 10 C atoms, or where the heteroaryl has 1-3 N as heteroatoms.

12. The compound of claim 11, wherein $R_{12}$ is a mono- or polysubstituted or unsubstituted aryl or heteroaryl, aralkyl or heteroaralkyl radical, where the alkyl radical has 1 to 4 C atoms or the aryl or heteroaryl has 6 C atoms.

13. The compound of claim 12, wherein $R_{12}$ is a mono- or polysubstituted or unsubstituted aryl or heteroaryl, aralkyl or heteroaralkyl radical, where the alkyl radical has 1 to 2 C atoms.

14. The compound of claim 2, wherein said structural element of the formula I is a —$CH_2$— group.

15. The compound of claim 3, wherein $R_8$ is phenyl, hydroxyphenyl, pyridyl, or aminopyridyl radical.

16. The compound of claim 4, wherein $R_8$ is pyridyl, or $P_2$ in the structure A of the general formula I is homophenylalanine, homotyrosine, indanylglycine or 4-pyridyl-homoalanine.

17. The compound of claim 16, wherein the P2 amino acid is in the D configuration.

18. The compound of claim 6, wherein the amino acid on which the radical R is located is in the D configuration.

19. The compound of claim 8, wherein said salts are with mineral acids or suitable organic acids.

20. The compound of claim 19, wherein said mineral acids or suitable organic acids are selected from the group consisting of hydrochloric acid, sulfuric acid, acetic acid, formic acid, methylsulfonic acid, succinic acid, malic acid, and trifluoroacetic acid.

21. The compound of claim 19, wherein said compounds are in the form of their hydrochlorides, sulfates, or acetates.

22. The medicament of claim 10, wherein said medicament is employed in the form of a solution for injection or infusion.

23. The compound of claim 1, wherein $R_{9*}$ comprises a mono- or polysubstituted or unsubstituted phenyl or pyridyl ring.

24. The compound of claim 6, wherein $R_{9*}$ is unsubstituted or comprises a substituent selected from —OH, —$NH_2$, —$NO_2$, —$COOR_{10}$, or a —$CH_2$—$COOR_{10}$ group, or a Cl, F or Br atom, and where $R_{10}$ is an H or an alkyl radical having 1 to 6 C atoms.

25. A compound selected from the group consisting of:
(8)
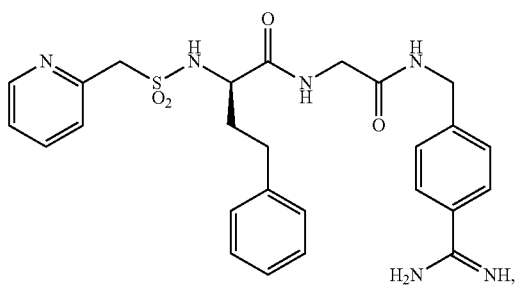
(9)
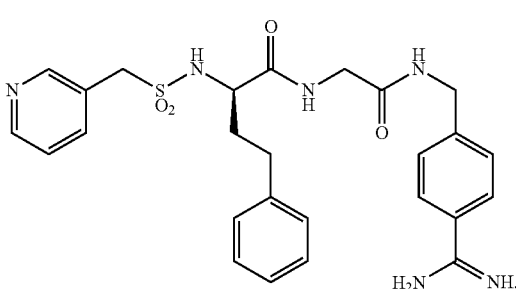
(17)
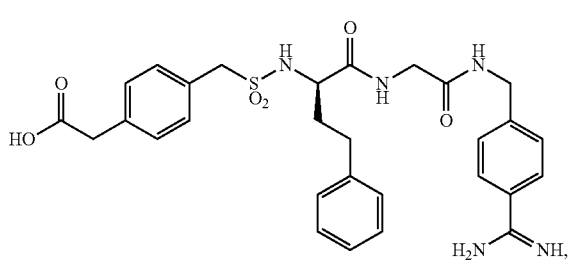
(19)
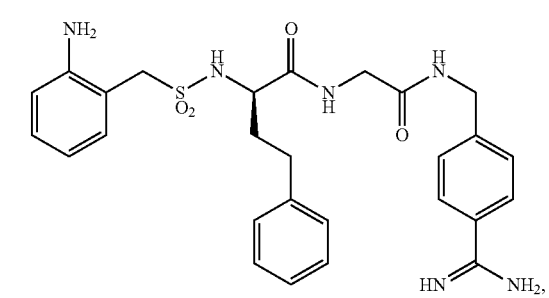
(5)
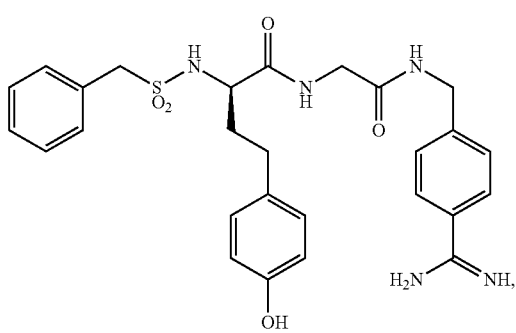
-continued
(1)
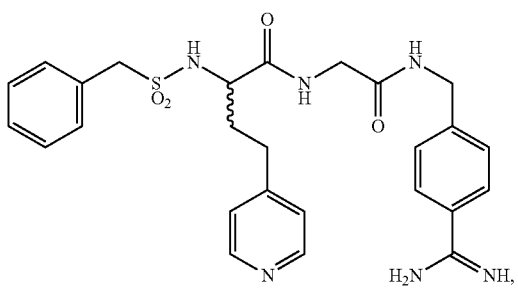
(2)
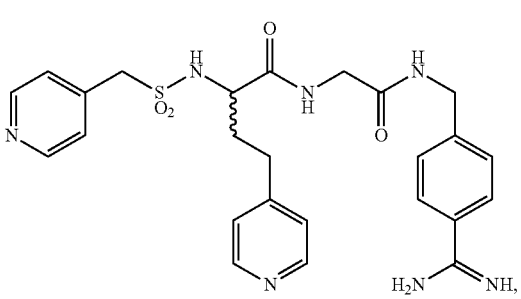
(3a)
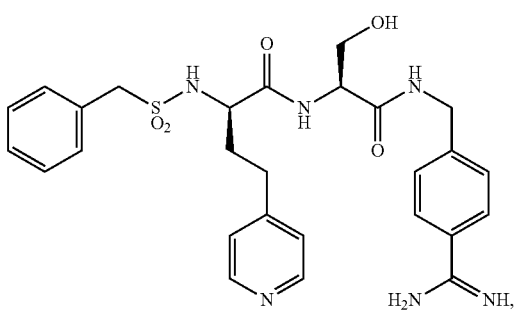
(25)
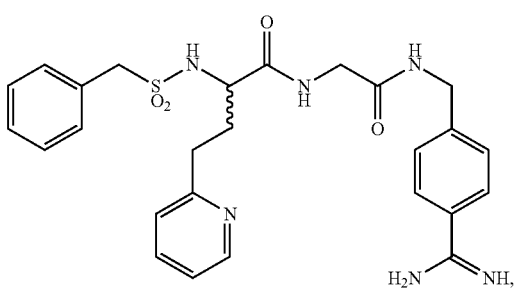
(26)
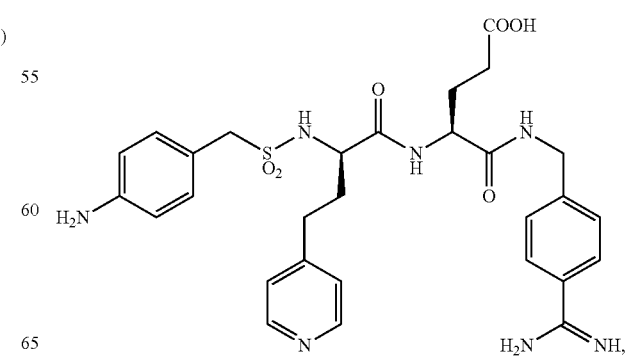

(27)
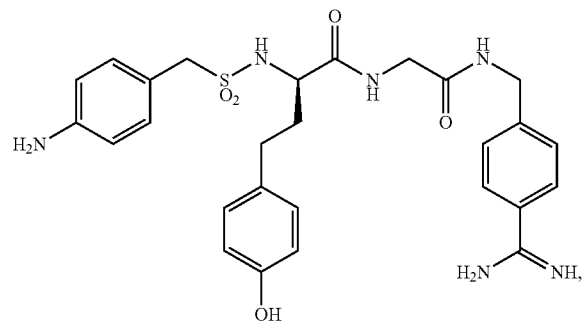
(31)
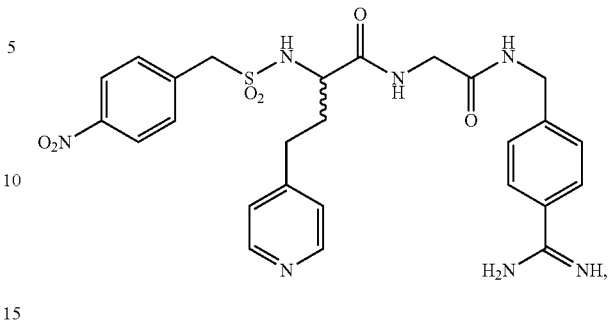
(28)
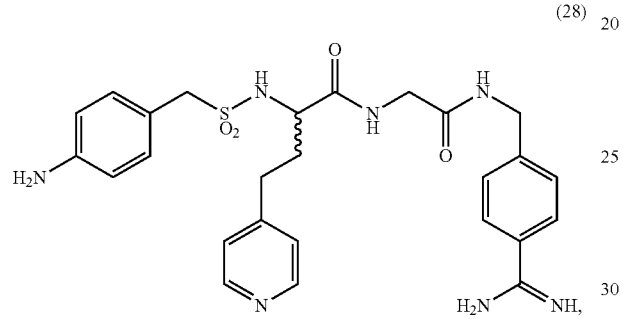
(32)
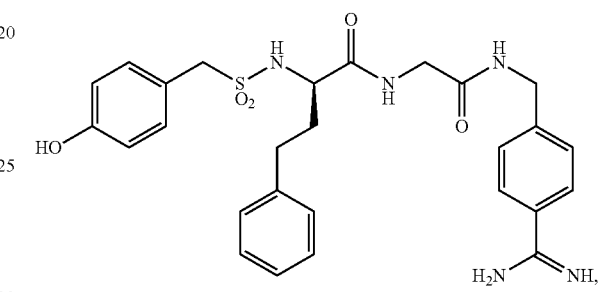
(29)
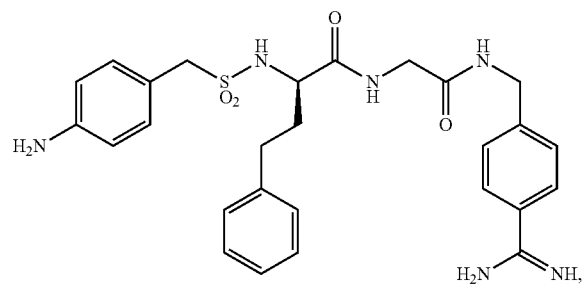
(33)
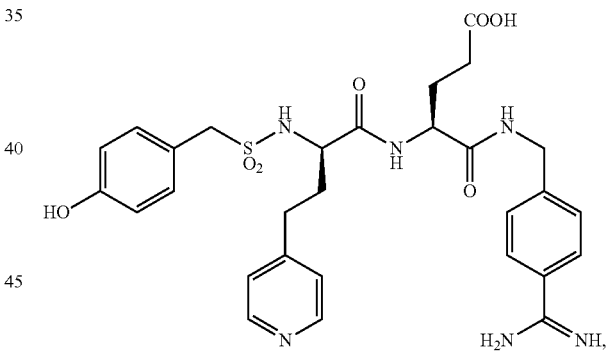
(30)
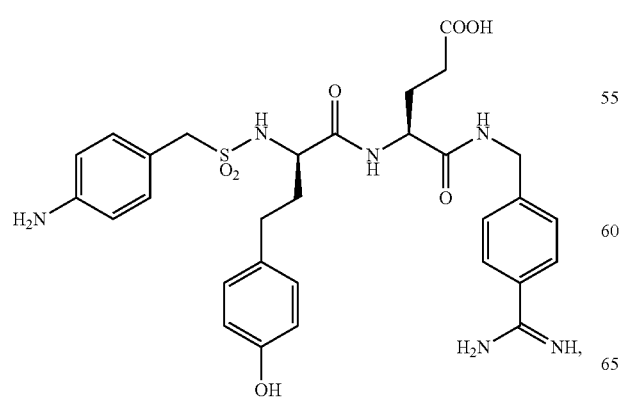
(34)
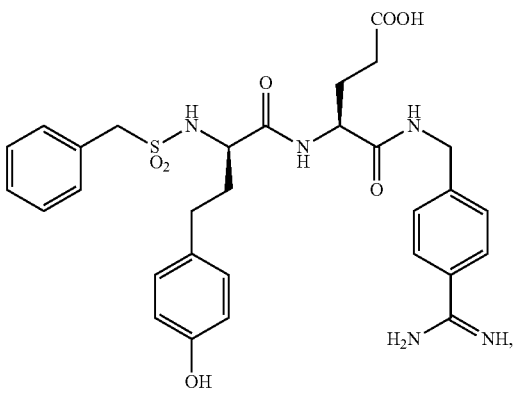

93 -continued
(35)
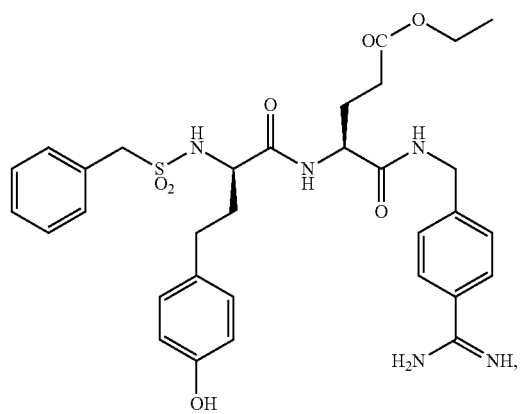
(36)
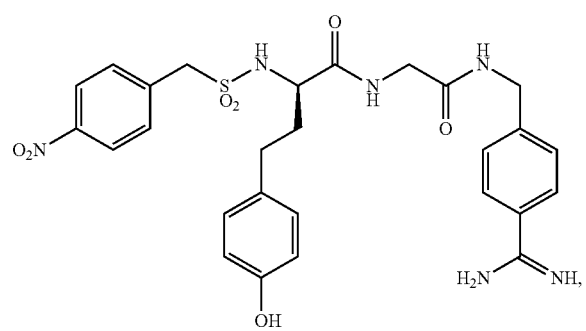
(37)
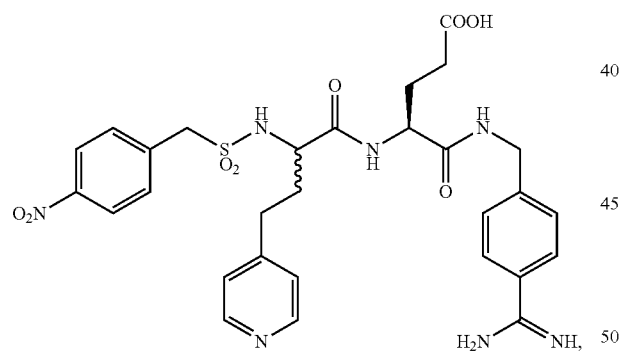
(40)
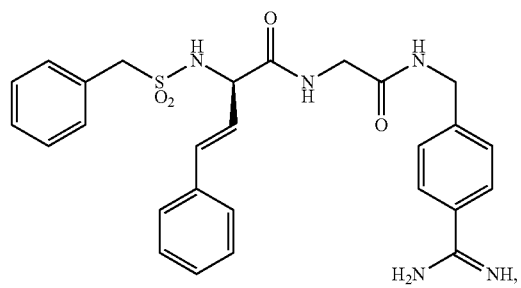
94 -continued
(41)
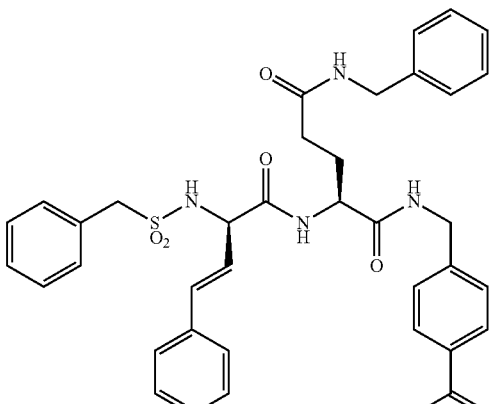
(42)
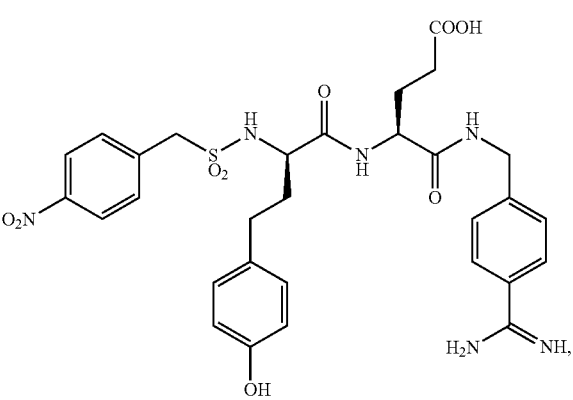
(43)
(44)
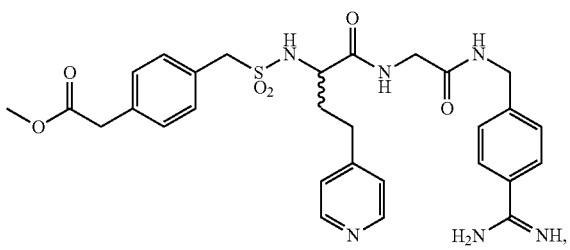

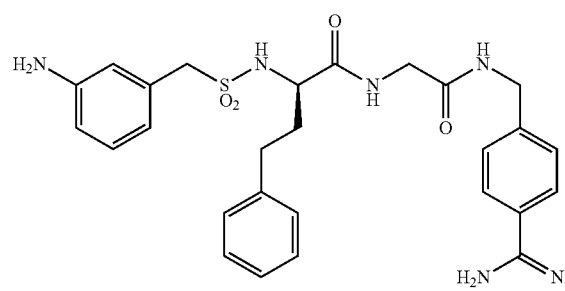
(45)
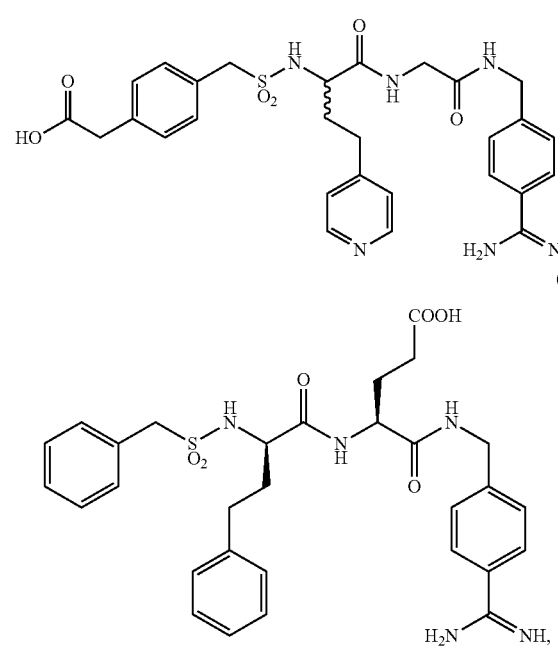
(46)
(49)
(50)
(51)
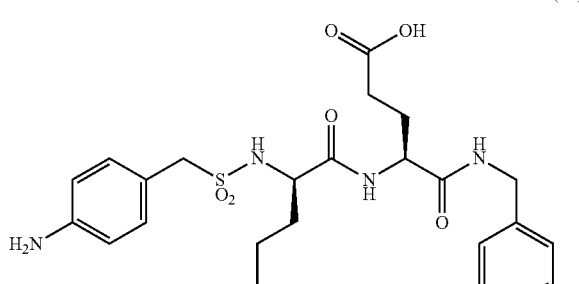
(52)
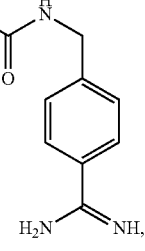
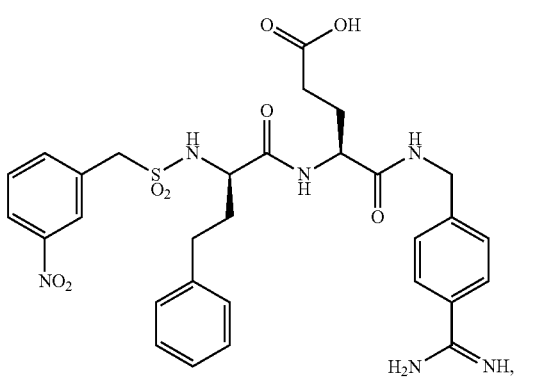
(56)
(60)
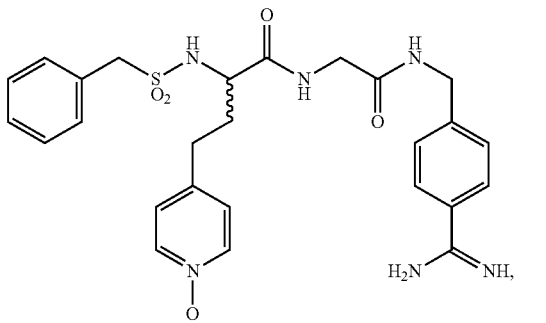
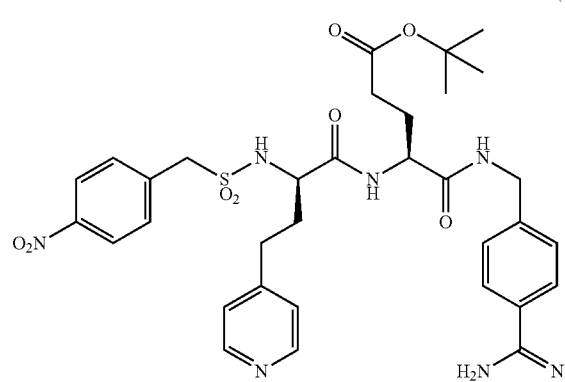
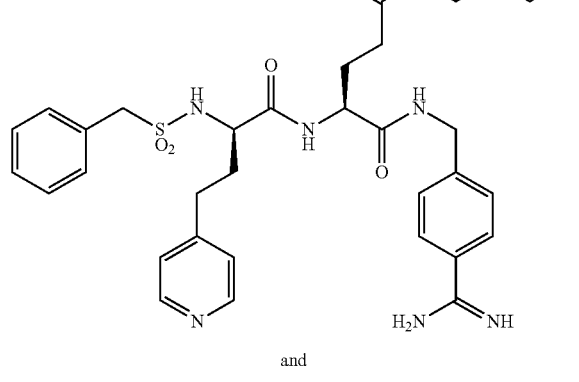
(61)
and -continued (65)

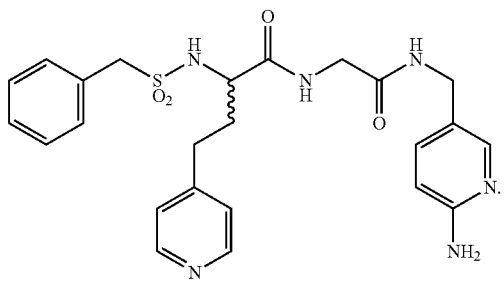

26. The compound of claim 1, wherein $R_2$ is —CH$_2$—CH$_2$—COOH, —CH$_2$—CH$_2$—COOCH$_2$CH$_3$ or —CH$_2$OH;

$R_4$ is —(CH$_2$)$_2$—R$_8$, where $R_8$ is a mono-substituted or unsubstituted phenyl or pyridyl attached to —(CH$_2$)$_2$— at a carbon of said phenyl or pyridyl ring $R_5$ is —SO$_2$R$_{9*}$, where R$_{9*}$ is a mono-substituted or unsubstituted benzyl or heteroaralkyl, where heteroaralkyl is aralkyl in which 1 ring C atom is replaced with N;

U is a phenyl radical;
V is (CH$_2$)$_n$ with n=0; and
z is present in position 4 and is an amidino group

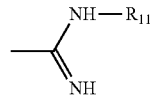

where $R_{11}$ is H; and
where each substituent is independently —OH, —NH$_2$, —NO$_2$, —COOH, —COOCH$_2$CH$_3$, or a halogen.

27. The compound of claim 26, wherein $R_2$ is —CH$_2$—CH$_2$—COOH or —CH$_2$—CH$_2$—COOCH$_2$CH$_3$.

28. The compound of claim 26, wherein R$_{9*}$ is benzylsulfonyl, aminobenzylsulfonyl, hydroxybenzylsulfonyl, chlorobenzylsulfonyl, fluorobenzylsulfonyl, carboxybenzylsulfonyl, ethyloxycarbonylbenzylsulfonyl, pyridylmethylsulfonyl, or N-(oxide)-pyridylmethylsulfonyl.

29. The compound of claim 28, wherein R$_{9*}$ is benzylsulfonyl, aminobenzylsulfonyl, hydroxybenzylsulfonyl, chlorobenzylsulfonyl, fluorobenzylsulfonyl, or pyridylmethylsulfonyl.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Homo Sapiens

<400> SEQUENCE: 1

Ile Glu Gly Arg
1
```